(12) United States Patent
Kang et al.

(10) Patent No.: US 7,031,186 B2
(45) Date of Patent: Apr. 18, 2006

(54) BIOSENSOR AND SENSING CELL ARRAY USING THE SAME

(75) Inventors: Hee Bok Kang, Daejeon (KR); Dong Yun Jeong, Cheongju-si (KR); Jae Hyoung Lim, Cheongju-si (KR); Young Jin Park, Sungnam-si (KR); Kye Nam Lee, Sungnam-si (KR); In Woo Jang, Seoul (KR); Seaung Suk Lee, Icheon-si (KR); Chang Shuk Kim, Icheon-si (KR)

(73) Assignee: Hynix Semiconductor Inc., Gyeonggi-do (KR)

( * ) Notice: Subject to any disclaimer, the term of this patent is extended or adjusted under 35 U.S.C. 154(b) by 210 days.

(21) Appl. No.: 10/651,027

(22) Filed: Aug. 29, 2003

(65) Prior Publication Data

US 2004/0120185 A1    Jun. 24, 2004

(30) Foreign Application Priority Data

| Dec. 21, 2002 | (KR) | ...................... | 10-2002-0082035 |
| Dec. 21, 2002 | (KR) | ...................... | 10-2002-0082036 |
| Dec. 21, 2002 | (KR) | ...................... | 10-2002-0082037 |
| Dec. 21, 2002 | (KR) | ...................... | 10-2002-0082038 |
| Dec. 21, 2002 | (KR) | ...................... | 10-2002-0082039 |

(51) Int. Cl.
*G11C 11/15* (2006.01)

(52) U.S. Cl. ...................... 365/173; 365/171; 365/158; 365/66; 365/97

(58) Field of Classification Search ................ 365/173, 365/171, 158, 66, 97
See application file for complete search history.

(56) References Cited

U.S. PATENT DOCUMENTS

| 3,798,623 | A | 3/1974 | Kaske et al. |
| 4,024,489 | A | 5/1977 | Bajorek et al. |
| 5,448,515 | A | 9/1995 | Fukami et al. |
| 5,640,343 | A | 6/1997 | Gallagher et al. |
| 5,650,958 | A | 7/1997 | Gallagher et al. |
| 5,745,406 | A | 4/1998 | Yamane et al. |
| 5,764,567 | A | 6/1998 | Parkin |
| 5,793,697 | A | 8/1998 | Scheuerlein |
| 5,801,984 | A | 9/1998 | Parkin |
| 5,841,692 | A | 11/1998 | Gallagher et al. |
| 5,966,323 | A | 10/1999 | Chen et al. |
| 6,023,395 | A | 2/2000 | Dill et al. |

(Continued)

FOREIGN PATENT DOCUMENTS

JP          10-162326          6/1998

(Continued)

*Primary Examiner*—Viet Q. Nguyen
(74) *Attorney, Agent, or Firm*—Heller Ehrman LLP

(57) ABSTRACT

A biosensor and a sensing cell array using a biosensor are disclosed. Adjacent materials containing a plurality of different ingredients are analyzed to determine the ingredients based on their magnetic susceptibility or dielectric constant. A sensing cell array includes such as a magnetization pair detection sensor including a MTJ (Magnetic Tunnel Junction) or GMR (Giant Magnetoresistive) device, a magnetoresistive sensor including a MTJ device and a magnetic material (current line), a dielectric constant sensor including a sensing capacitor and a switching device, a magnetization hole detection sensor including a MTJ or GMR device, a current line, a free ferromagnetic layer and a switching device, and a giant magnetoresistive sensor including a GMR device, a switching device and a magnetic material (or forcing wordline). Ingredients of adjacent materials are separated based on electrical characteristics of ingredients by sensing magnetic susceptibility and dielectric constant depending on the sizes of the ingredients.

14 Claims, 69 Drawing Sheets

U.S. PATENT DOCUMENTS

| | | |
|---|---|---|
| 6,114,719 A | 9/2000 | Dill et al. |
| 6,127,045 A | 10/2000 | Gill |
| 6,128,239 A | 10/2000 | Perner |
| 6,219,212 B1 | 4/2001 | Gill et al. |
| 6,447,723 B1 | 9/2002 | Schermer et al. |
| 6,447,887 B1 | 9/2002 | Claus et al. |
| 6,447,991 B1 | 9/2002 | Daitch et al. |
| 6,448,043 B1 | 9/2002 | Choi et al. |
| 6,448,238 B1 | 9/2002 | Shoichet et al. |
| 6,449,406 B1 | 9/2002 | Fan et al. |
| 6,452,764 B1 | 9/2002 | Abraham et al. |
| 6,538,919 B1 | 3/2003 | Abraham et al. |
| 6,744,086 B1 * | 6/2004 | Daughton et al. ......... 257/295 |
| 6,777,730 B1 * | 8/2004 | Daughton et al. ......... 257/295 |
| 6,831,314 B1 * | 12/2004 | Higo et al. ................. 257/295 |
| 6,917,540 B1 * | 7/2005 | Ooishi ....................... 365/173 |
| 2001/0040778 A1 | 11/2001 | Abraham et al. |
| 2002/0117694 A1 | 8/2002 | Migliorato et al. |
| 2002/0191451 A1 * | 12/2002 | Kishi et al. ................ 365/200 |

FOREIGN PATENT DOCUMENTS

| | | |
|---|---|---|
| JP | 10-190090 | 7/1998 |
| JP | 410261287 A * | 9/1998 |
| JP | 11-161919 | 6/1999 |
| JP | 2000-188435 | 7/2000 |
| JP | 2000-213908 | 8/2000 |
| JP | 2002-148132 | 5/2002 |

* cited by examiner

| KIND SIZE | INGREDIENT_1 | INGREDIENT_2 | $\cdots$ | INGREDIENT_n |
|---|---|---|---|---|
| SIZE_1 | $\mu_{11}$ | $\mu_{12}$ | | $\mu_{1n}$ |
| SIZE_2 | $\mu_{21}$ | $\mu_{22}$ | | $\mu_{2n}$ |
| $\vdots$ | | | | |
| SIZE_m | $\mu_{m1}$ | $\mu_{m2}$ | | $\mu_{mn}$ |

Fig.2
(Prior Art)

| SIZE \ KIND | INGREDIENT_1 | INGREDIENT_2 | ... | INGREDIENT_n |
|---|---|---|---|---|
| SIZE_1 | $\varepsilon_{11}$ | $\varepsilon_{12}$ | | $\varepsilon_{1n}$ |
| SIZE_2 | $\varepsilon_{21}$ | $\varepsilon_{22}$ | | $\varepsilon_{2n}$ |
| ⋮ | | | | |
| SIZE_m | $\varepsilon_{m1}$ | $\varepsilon_{m2}$ | | $\varepsilon_{mn}$ |

Fig.5
(Prior Art)

BIOSENSOR AND SENSING CELL ARRAY USING THE SAME

BACKGROUND OF THE INVENTION

1. Field of the Invention

The present invention relates to a biosensor and a sensing cell array, and more specifically, to a technology to analyze ingredients of adjacent materials depending on electrical characteristics by using a dielectric constant sensor and magnetization characteristics of a magnetization pair detection sensor.

2. Description of the Prior Art

Most semiconductor memory manufacturers have recently developed MTJ (Magnetic Tunnel Junction) and GMR (Giant Magneto Resistive) devices using ferromagnetic materials.

The MTJ device, that comprises two magnetic layers separated by an insulating layer, utilizes spin magnetic permeation phenomenon. In the MTJ device, current better permeates the insulating layer when spin directions are parallel than when anti-parallel in the two magnetic layers. The GMR device, that comprises two magnetic layers separated by a non-magnetic layer, utilizes a giant magnetoresistive phenomenon. In the GMR device, resistance is more differentiated when spin directions are anti-parallel than when parallel in the two magnetic layers.

FIGS. 1a and 1b are diagrams illustrating the operation principle of a conventional MTJ device.

The conventional MTJ device comprises a free ferromagnetic layer 1, a tunnel junction layer 2 and a fixed ferromagnetic layer 3.

When magnetic field lines in the fixed ferromagnetic layer 3 are transmitted into the free ferromagnetic layer 1 through adjacent materials, magnetoresistance varies according to magnetic susceptibilities of the adjacent materials. The magnetic flux density is represented by $B=\mu H$ (here, $\mu$=magnetic susceptibility, H=magnetic flux). The value of magnetic flux density B varies according to the magnetic susceptibility $\mu$.

As shown in FIG. 1a, if materials having high magnetic susceptibility $\mu$ exist between the fixed ferromagnetic layer 3 and the free ferromagnetic layer 1, the magnetic flux density B of the free ferromagnetic layer 1 increases. On the other hand, as shown in FIG. 1b, if materials having low magnetic susceptibility $\mu$ exist between the fixed ferromagnetic layer 3 and the free ferromagnetic layer 1, the magnetic flux density B of the free ferromagnetic layer 1 decreases. As a result, the value of magnetoresistance depends on the magnetic susceptibility $\mu$ of the adjacent materials between the fixed ferromagnetic layer 3 and the free ferromagnetic layer 1.

FIG. 2 is an analysis table illustrating magnetic susceptibility depending on ingredients of materials adjacent to a MTJ device.

The magnetization constant $\mu$ varies depending on kinds and size of ingredients of the adjacent materials.

FIG. 3 is a diagram illustrating capacitance of a general capacitor.

The capacitor comprises a first electrode 4 and a second electrode 5. The capacitor has a different dielectric constant $\in$ depending on the distance d between the first electrode 4 and the second electrode 5 and on the area S of the capacitor. That is, the capacitance is $C=\in S/d$ (here, S=the area of the capacitor, and d=the distance between the two electrodes). The capacitance C is proportional to the dielectric constant $\in$ and the area S of the capacitor, and inversely proportional to the distance d.

FIG. 4 is a diagram illustrating a voltage transmission characteristic of the general capacitor.

Two capacitors connected between a driving plate line PL and a ground voltage terminal have capacitances C1 and C2. A node voltage between the two capacitors is Vs. A driving voltage supplied to the plateline PL by the two capacitors is a driving plate voltage V_PL. Here, the node voltage $Vs=\{C1/(C1+C2)\} \times V\_PL$. The node voltage Vs is proportional to the capacitance C1, and is inverse proportional to the capacitance C2.

FIG. 5 shows that dielectric constant $\in$ is differentiated depending on the kinds and sizes of adjacent materials.

Due to improvement of living environments, people have become more interested in health and life prolongation. After diseases threatening human life occur, people have emphasized preventing the expected diseases rather than simply curing them. Also, they have struggled to control environmental pollution.

As a result, systems to detect various disease causing factors, pollution and toxic substance have been required. To meet this trend, analysis methods of adjacent materials place more weight on biosensors with other physical and chemical sensors.

In order to examine for human diseases using these adjacent material detecting systems, sensing methods are needed for analyzing ingredients of blood, for analyzing ingredients of compounds or for recognizing the skin. However, conventional sensing methods depend on physical or chemical methods for analyzing material ingredients. As a result, large equipment and cost for are required for such testing. Since it takes a long time for such tests, it is difficult to analyze ingredients of various adjacent materials.

SUMMARY OF THE INVENTION

In order to quickly analyze ingredients of various materials quantitative analysis methods are required to analyze the ingredients of materials surrounding, beside or proximate to sensors (herein referred to as "adjacent material") using the above-described magnetoresistive sensor or the giant magnetoresistive sensor. Also, the quantitative analysis method using the different dielectric constant of the above-described capacitor depending on kinds and sizes of adjacent materials is useful.

Accordingly, it is an object of the present invention to identify ingredients of adjacent materials by differentiatiating magnetic susceptibility and electrical properties using a plurality of MTJ sensors and/or GMR sensors to analyze the ingredients quantitatively.

It is another object of the present invention to sense different values of dielectric constant depending on the kinds and sizes of ingredients of adjacent materials in order to analyze the ingredients of adjacent materials as electrical ingredients.

In an embodiment, a biosensor comprises a MTJ (Magnetic Tunnel Junction) device coupled to a switching device and a sense wordline. The MTJ device comprises a free ferromagnetic layer, a tunnel junction layer and a fixed ferromagnetic layer. The switching device, formed under the fixed ferromagnetic layer of the MTJ device, outputs current sensed in the MTJ device into a sense bitline. The sense wordline, formed on the free ferromagnetic layer, applies different bias voltages to the MTJ device. When a magnetic field line of the fixed ferromagnetic layer is transmitted into the free ferromagnetic layer, the current outputted from the switching device varies according to the magnetic flux density that depends on the adjacent materials.

In an embodiment, a biosensor comprises a GMR (Giant Magneto Resistance) device coupled to a switching device and a sense wordline. The GMR device comprises a free ferromagnetic layer, a conductive resistor and a fixed ferromagnetic layer. The switching device, formed under the fixed ferromagnetic layer of the GMR device, outputs current sensed in the GMR device into a sense bitline. The sense wordline, connected to an electrode of the conductive resistor, applies different bias voltages to the GMR device. When a magnetic field of the fixed ferromagnetic layer is transmitted into the free ferromagnetic layer, the current outputted from the switching device varies according to the magnetic flux density that depends on the adjacent materials.

In an embodiment, a sensing cell array using a biosensor comprises a plurality of sense wordlines, a plurality of sense bitlines, a plurality of magnetization pair detection sensors and a plurality of sense amplifiers. The plurality of sense wordlines are arranged parallel to a plurality of wordlines. The plurality of sense bitlines are arranged perpendicular to the plurality of sense wordlines and the plurality of wordlines. The plurality of magnetization pair detection sensors, connected to the plurality of sense wordlines, the plurality of wordlines and the plurality of sense bitlines, sense different values of magnetic flux density depending on adjacent materials. The plurality of sense amplifiers are connected to the plurality of sense bitlines.

In an embodiment, a biosensor comprises a MTJ device, a ferromagnetic material and a switching device. The MTJ device comprises a free ferromagnetic layer to receive a sense wordline voltage, a tunnel junction layer and a fixed ferromagnetic layer. The ferromagnetic material, formed on the free ferromagnetic layer, forms a magnetic field depending on the magnetic coupling with the free ferromagnetic layer. The switching device, formed under the fixed ferromagnetic layer of the MTJ device, outputs current sensed in the MTJ device into a sense bitline. Here, the current outputted from the switching device varies according to magnetoresistive values that depend on adjacent materials.

In an embodiment, a biosensor comprises a MTJ device coupled to a current line and a switching device. The MTJ device comprises a free ferromagnetic layer to receive a sense wordline voltage, a tunnel junction layer and a fixed ferromagnetic layer. The current line, formed on the free ferromagnetic layer, receives a forcing wordline voltage and forms a magnetic field depending on the magnetic coupling with the free ferromagnetic layer. The switching device, formed under the fixed ferromagnetic layer of the MTJ device, outputs current sensed in the MTJ device into a sense bitline. Here, the current outputted from the switching device varies according to magnetoresistive values depending on adjacent materials.

In an embodiment, a sensing cell array using a biosensor comprises a plurality of sense wordlines, a plurality of sense bitlines, a plurality of magnetoresistive sensors and a plurality of sense amplifiers. The plurality of sense wordlines are arranged parallel to a plurality of wordlines. The plurality of sense bitlines are arranged perpendicular to the plurality of sense wordlines and the plurality of wordlines. The plurality of magnetoresistive sensors are connected to the plurality of sense wordlines, the plurality of wordlines and the plurality of sense bitlines. The plurality of sense amplifiers are connected to the plurality of sense bitlines. Here, depending on ingredients of adjacent materials formed in a magnetic field induced by magnetic coupling with magnetic materials, each magnetoresistive sensor senses different magnetoresistive values according to magnetic fields generated from the magnetic materials.

In an embodiment, a sensing cell array using a biosensor, comprises a plurality of sense wordlines, a plurality of sense bitlines, a plurality of magnetoresistive sensors and a plurality of sense amplifiers. The plurality of sense wordlines are arranged parallel to a plurality of wordlines and a plurality of forcing wordlines. The plurality of sense bitlines are arranged perpendicular to the plurality of sense wordlines, the plurality of wordlines and the plurality of forcing wordlines. The plurality of magnetoresistive sensors, connected between the plurality of sense wordlines, the plurality of wordlines, the plurality of forcing wordlines and the plurality of sense bitlines, sense different magnetoresistive values according to a magnetic field generated by a current line where a forcing wordline voltage is applied. The plurality of sense amplifiers are connected to the plurality of sense bitlines.

In an embodiment, a biosensor comprises a transistor and a sensing capacitor. The transistor has a gate connected to a wordline and a drain connected to a sensing bitline. The sensing capacitor has a first electrode connected to a sensing plateline and a second electrode connected to a source of the transistor. Here, a sensing voltage outputted from the transistor varies according to dielectric constants of the sensing capacitor.

In an embodiment, a sensing cell array using a biosensor comprises a plurality of sensing platelines, a plurality of sensing bitlines, a plurality of dielectric constant sensors and a plurality of sense amplifiers. The plurality of sensing platelines are arranged parallel to a plurality of wordlines. The plurality of sensing bitlines are arranged perpendicular to the plurality of wordlines and the plurality of sensing platelines. The plurality of dielectric constant sensors, connected to the plurality of wordlines, the plurality of sensing platelines and the plurality of sensing bitlines, sense different dielectric constants of adjacent materials formed between two electrodes of a capacitor. The plurality of sense amplifiers are connected to the plurality of sensing bitlines.

In an embodiment, a biosensor comprises a MTJ device, a second free ferromagnetic layer, a current line and a switching device. The MTJ device comprises a first free ferromagnetic layer, a tunnel junction layer and a fixed ferromagnetic layer. The second free ferromagnetic layer has the same direction of magnetic flux as that of the first free ferromagnetic layer and has a predetermined interval with the first free ferromagnetic layer. The current line, formed under the first free ferromagnetic layer and the second free ferromagnetic layer, receives current to induce a magnetic field. The switching device, formed under the current line, outputs current sensed in the MTJ device into a sense bitline. Here, the current outputted from the switching device varies according to magnetic susceptibility of adjacent materials exposed on a sensing hole formed between the first free ferromagnetic layer and the second free ferromagnetic layer.

In an embodiment, a biosensor comprises a GMR device, a second free ferromagnetic layer, a current line and a switching device. The GMR device comprises a first free ferromagnetic layer, a sensing conductive layer and a fixed ferromagnetic layer. The second free ferromagnetic layer has the same direction of magnetic flux as that of the first free ferromagnetic layer and has a predetermined interval with the first free ferromagnetic layer. The current line, formed under the first free ferromagnetic layer and the second free ferromagnetic layer, receives current to induce a magnetic field. The switching device, formed under the current line, outputs current sensed in the GMR device into a sense bitline. Here, the current outputted from the switching device varies according to magnetic susceptibility of adjacent materials exposed on a sensing hole formed between the first free ferromagnetic layer and the second free ferromagnetic layer.

In an embodiment, a sensing cell array using a biosensor comprises a plurality of wordlines, a plurality of sense bitlines, a plurality of magnetization hole detection sensors and a plurality of sense amplifiers. The plurality of wordlines are arranged parallel to a plurality of forcing wordlines and a plurality of sense wordlines. The plurality of sense bitlines are arranged perpendicular to the plurality of forcing wordlines, the plurality of sense wordlines and the plurality of wordline. The plurality of magnetization hole detection sensors, connected to the plurality of forcing wordline, the plurality of sense wordlines, the plurality of wordlines and the plurality of sense bitlines, sense different magnetic susceptibility depending on adjacent materials exposed on a sensing hole formed between the two free ferromagnetic layers. The plurality of sense amplifiers are connected to the plurality of sense bitlines.

In an embodiment, a biosensor comprises a GMR device, a magnetic material, a sense wordline and a switching device. The GMR device comprises a free ferromagnetic layer, a conductive resistor and a fixed ferromagnetic layer. The magnetic material, formed on the free ferromagnetic layer, forms a magnetic field depending on magnetic coupling with the free ferromagnetic layer. The sense wordline, formed on a portion of the conductive resistor, receives a sense wordline voltage. The switching device, formed under the other portion of the conductive resistor, outputs current sensed in the GMR device into a sense bitline. Here, the current outputted from the switching device varies according to the affect on magnetoresistive values of adjacent materials formed on the magnetic field.

In an embodiment, a biosensor comprises a GMR device, a forcing wordline, a sense wordline and a switching device. The GMR device comprises a free ferromagnetic layer, a conductive resistor and a fixed ferromagnetic layer. The forcing wordline, formed on the free ferromagnetic layer, receives a forcing wordline voltage and forming a magnetic field depending on magnetic coupling with the free ferromagnetic layer. The sense wordline is formed on a portion of the conductive resistor. The switching device, formed under the other portion of the conductive resistor, outputs current sensed in the GMR device into a sense bitline. Here, the current outputted from the switching device varies according to magnetoresistive values of adjacent materials formed on the magnetic field.??

In an embodiment, a sensing cell array using a biosensor comprises a plurality of wordlines, a plurality of sense bitlines, a plurality of giant magnetoresistive sensors, a plurality of sense wordline drivers and a plurality of sense amplifiers. The plurality of wordlines are arranged parallel to a plurality of sense wordlines. The plurality of sense bitlines are arranged perpendicular to the plurality of sense wordlines and the plurality of wordlines. The plurality of giant magnetoresistive sensors, connected to the plurality of sense wordline, the plurality of wordlines and the plurality of sense bitlines, sense magnetoresistive values of adjacent materials formed on a magnetic field induced by magnetic coupling with magnetic materials. The plurality of sense wordline drivers apply different bias voltages to the plurality of sense wordlines. The plurality of sense amplifiers are connected to the plurality of sense bitlines.

In an embodiment, a sensing cell array using a biosensor comprises a plurality of forcing wordlines, a plurality of sense bitlines, a plurality of giant magnetoresistive sensors, a plurality of sense wordline drivers and a plurality of sense amplifiers. The plurality of forcing wordlines are arranged parallel to a plurality of sense wordlines and a plurality of wordlines. The plurality of sense bitlines are arranged perpendicular to the plurality of sense wordlines, the plurality of wordlines and the plurality of forcing wordlines. The plurality of giant magnetoresistive sensors, connected to the plurality of sense wordlines, the plurality of wordlines, the plurality of forcing wordlines and the plurality of sense bitlines, sense magnetoresistive values of adjacent materials formed in a magnetic field induced by magnetic coupling with the forcing wordlines. The plurality of sense wordline drivers apply different bias voltages to the plurality of sense wordlines. The plurality of sense amplifiers are connected to the plurality of sense bitlines.

BRIEF DESCRIPTION OF THE DRAWINGS

FIG. 2 is a table illustrating magnetic susceptibility depending on ingredients and sizes of adjacent materials.

FIG. 5 is a table illustrating dielectric constant depending on ingredients and sizes of adjacent materials.

DETAILED DESCRIPTION OF THE PREFERRED EMBODIMENTS

The present invention will be described in detail with reference to the attached drawings.

Figure 1A:
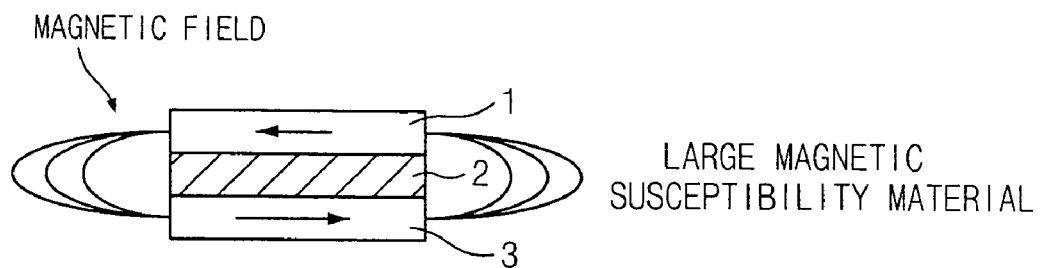
FIGS. 1a and 1b are diagrams illustrating the operation principle of a conventional MTJ device.
Figure 1B:
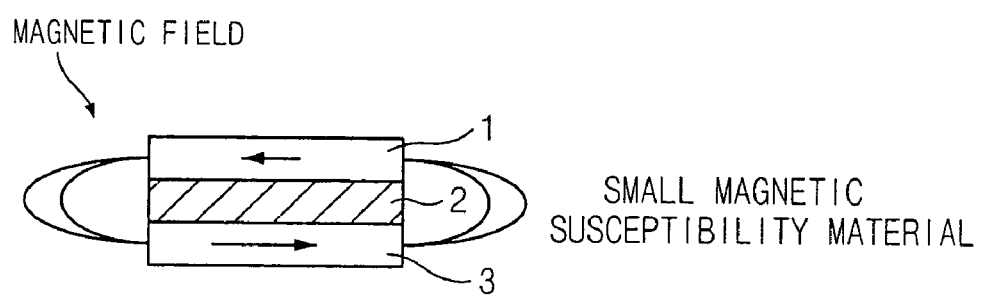
Figure 3:
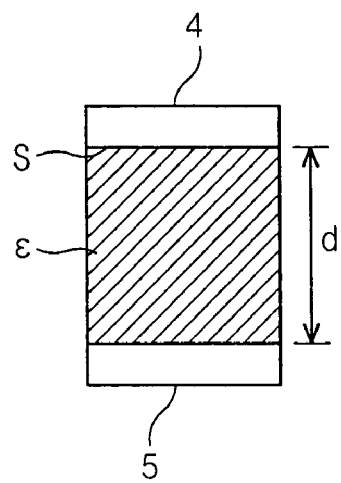
FIG. 3 is a diagram illustrating capacitance of a conventional capacitor.
Figure 4:
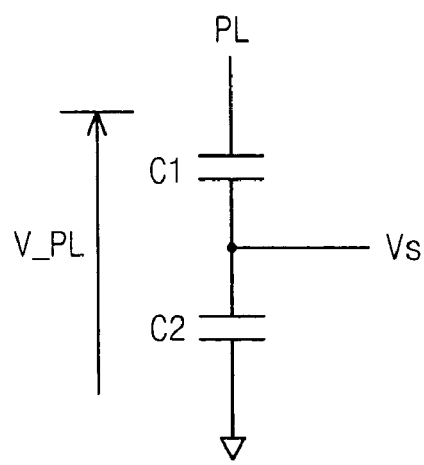
FIG. 4 is a diagram illustrating a voltage transmission characteristic of the common capacitor.
Figure 6:
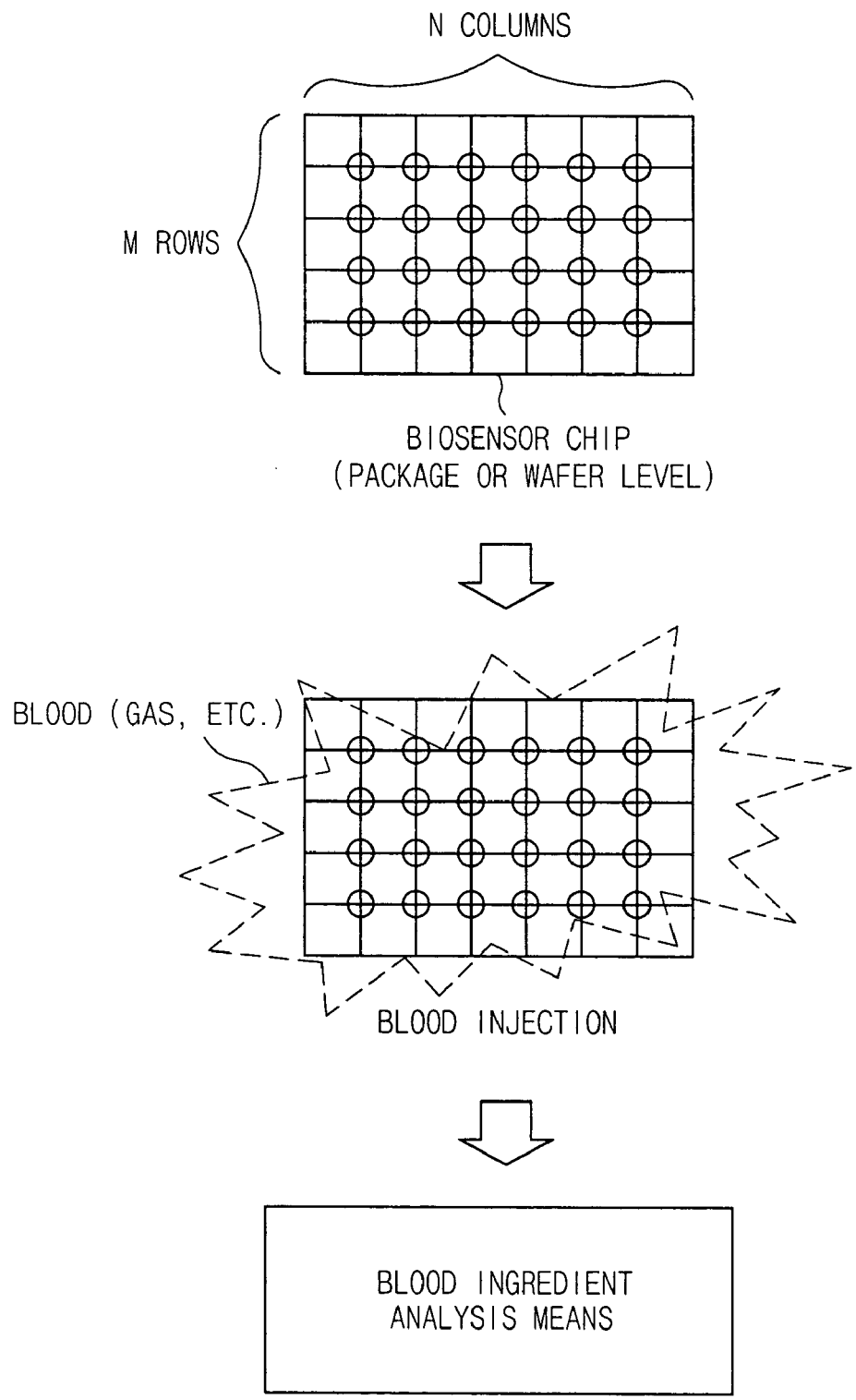
FIGS. 6 and 7 are conceptual diagrams illustrating a biosensor and a sensing cell array using the same according to an embodiment of the present invention.

FIG. 6 is a conceptual diagram illustrating a biosensor and a sensing cell array using the same according to an embodiment of the present invention.

A plurality of biosensors are arranged in a sensing array comprising N columns and M rows. A biosensor chip comprising a sensing cell array is prepared in a package or wafer level.

Ingredient measuring data comprising adjacent materials are exposed to each biosensor. Thereafter, ingredient measuring data are measured in each cell array of biosensors to electrically analyze the data using a blood ingredient analysis means.

For adjacent materials, blood, gas or other solution may be used. In an embodiment of the present invention, blood is used for the adjacent material.

Figure 7:
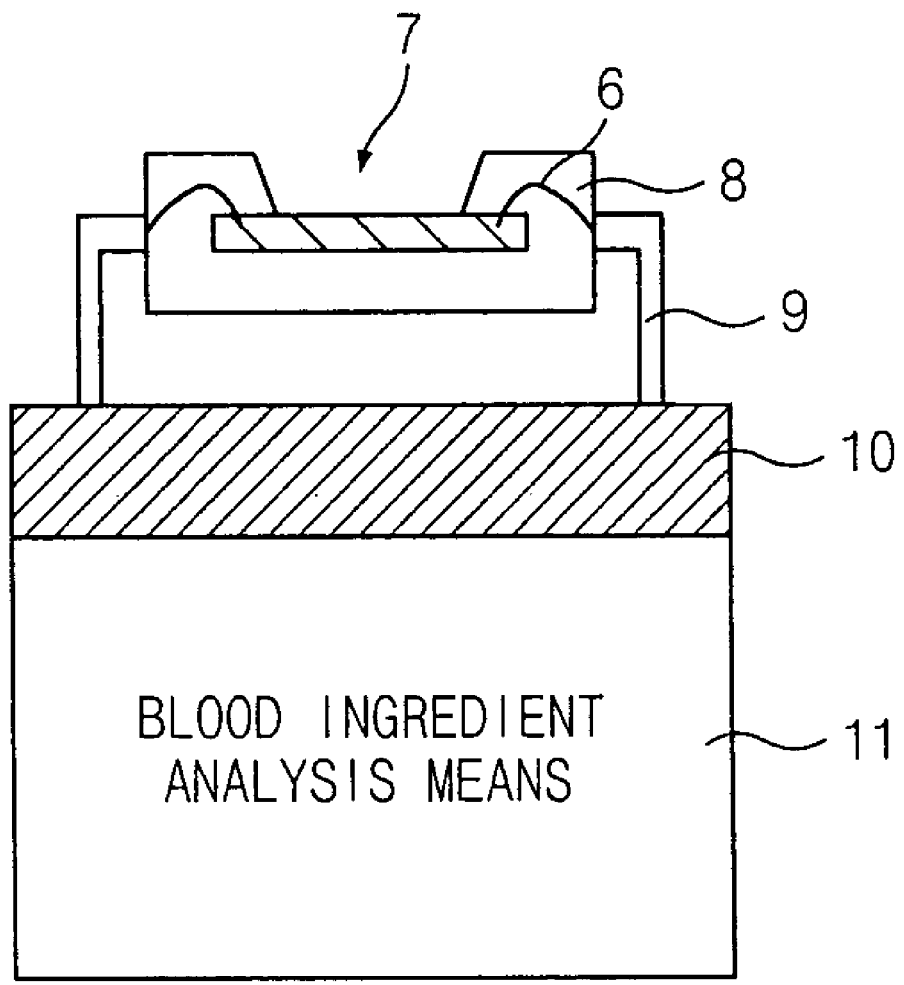

FIG. 7 is a diagram illustrating a package and a sensing system of a sensing cell array using a biosensor according to an embodiment of the present invention.

In an embodiment, the sensing system includes a blood ingredient analysis means 11 and a sensing package 8 mounting a biosensor 7 thereon. The sensing package 8 is disposed on a connection board 10 mounted on the blood ingredient analysis means 11 through a connection lead 9. The biosensor 7 in the sensing package 8 is connected to the connection lead 9 through a connection line 6.

Ingredient data of adjacent materials sensed from the biosensor 7 are outputted into the blood ingredient analysis means 11 through the connection lead 9 and the connection board 10. The blood ingredient analysis means 11 separates ingredient data of measured adjacent materials into electrical signals characteristic of the ingredients to analyze the ingredients of the adjacent materials quantitatively.

In an embodiment of the present invention, biosensors comprises a magnetization pair detection sensor, a magnetoresistive sensor, a giant magnetoresistive sensor, a magnetization hole detection sensor or a dielectric constant sensor. These five sensors are examples for the biosensors.

Referring to FIGS. 8 to 18, a magnetization pair detection sensor and a sensing cell array using the same according to a first embodiment of the present invention are described in detail.

Figure 8:
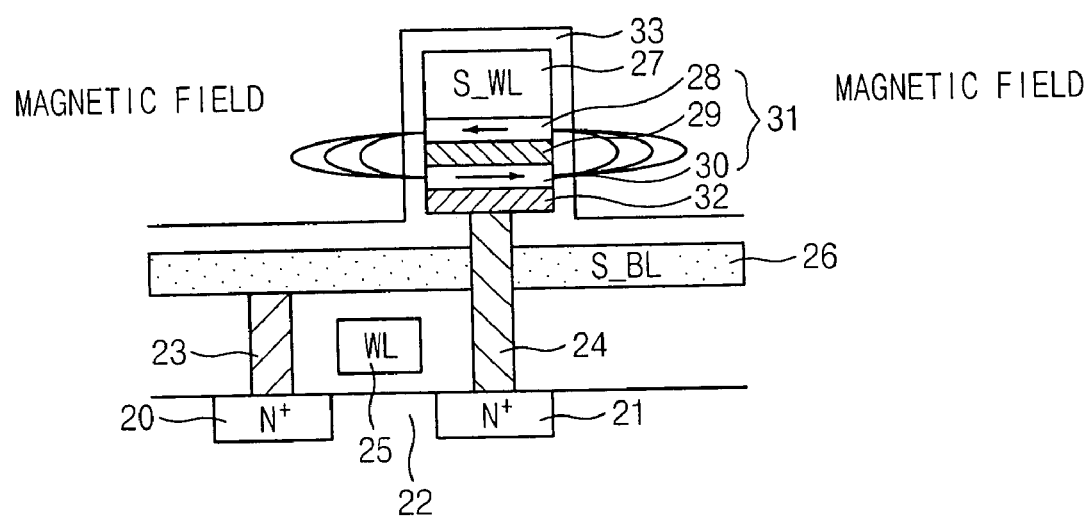
FIG. 8 is a structural diagram illustrating a magnetization pair detection sensor using a MTJ device according to an embodiment of the present invention.

FIG. 8 is a structural diagram illustrating a magnetization pair detection sensor using a MTJ device according to a first embodiment of the present invention.

In the first embodiment, the magnetization pair detection sensor comprises a switching device and a MTJ device 31.

The MTJ device 31 comprises a free ferromagnetic layer 28, a tunnel junction layer 29 and a fixed ferromagnetic layer 30.

The switching device comprises a NMOS transistor. The NMOS transistor has a drain 20 connected to a sense bitline 26 through a contact line 23, a gate 22 connected to a wordline 25, and a source 21 connected to a barrier conductive layer 32 formed under the MTJ device 31 through a contact line 24.

The free ferromagnetic layer 28 formed on the MTJ device 31 is connected to a sense wordline 27. The entire device is insulated by an oxide protective layer 33.

When portions of the magnetic field (illustrated in the figures as lines of magnetic flux and referred to herein as "magnetic field lines") of the fixed ferromagnetic layer 30 are transmitted into the free ferromagnetic layer 28, different values of magnetoresistance are measured by the strength of the magnetic field lines differentiated by ingredients of magnetic material.

Figure 9A:
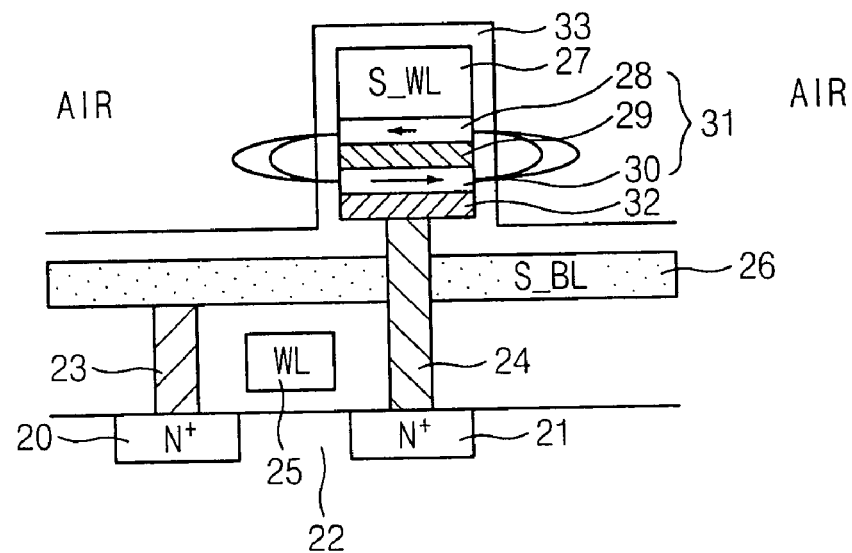
FIGS. 9a and 9b are diagrams illustrating operation characteristics of the magnetization pair detection sensor of FIG. 8.
Figure 9B:
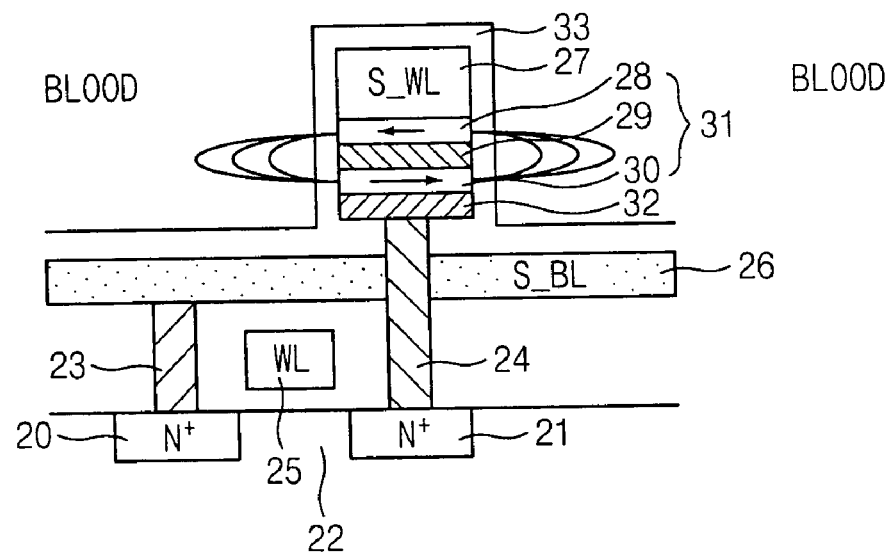

FIGS. 9a and 9b are diagrams illustrating operational characteristics of the magnetization pair detection sensor of FIG. 8 depending on adjacent magnetic materials.

As shown in FIG. 9a, when the adjacent magnetic material that is adjacent to the magnetization pair detection sensor is air, the free ferromagnetic layer 28 has a small magnetic density due to air having a small magnetic susceptibility. As a result, magnetoresistance is shown to be small. However, as shown in FIG. 9b, when the adjacent magnetic material of the magnetization pair detection sensor is blood, the free ferromagnetic layer 28 has a large magnetic density due to blood having a large magnetic susceptibility. As a result, magnetoresistance is shown to be large.

Figure 10A:
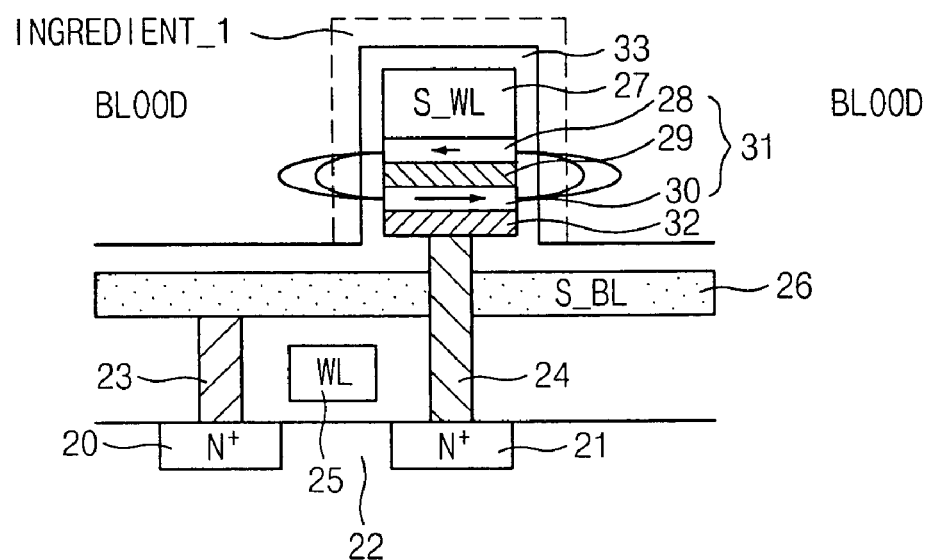
FIGS. 10a and 10b are diagrams illustrating ingredient separation depending on variations in a sense wordline voltage of the magnetization pair detection sensor of FIG. 8.
Figure 10B:
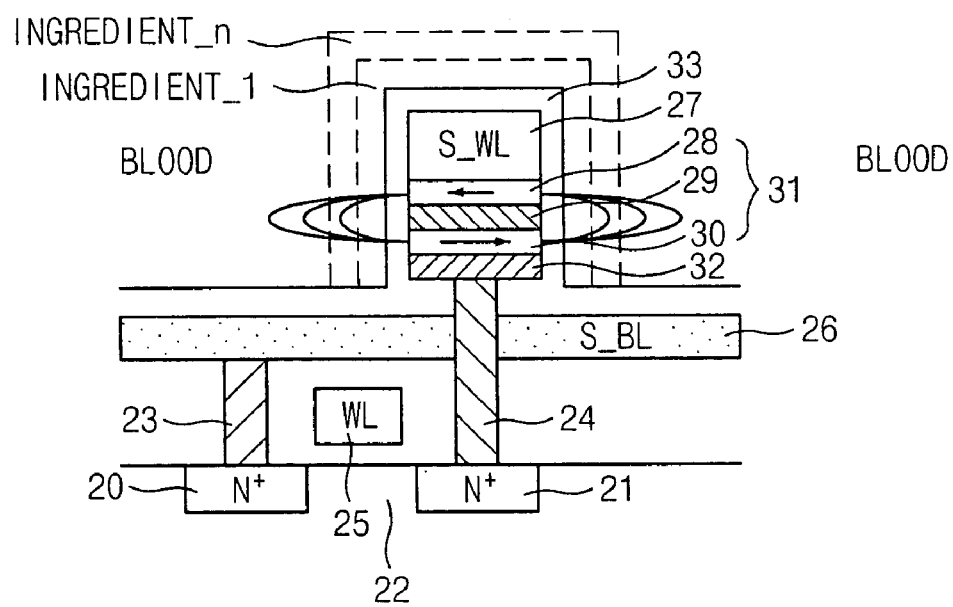

FIGS. 10a and 10b are diagrams illustrating ingredient separation depending on variation in a sense wordline S_WL voltage of the magnetization pair detection sensor of FIG. 8 using the MTJ device.

When a sensing voltage is applied to a sense wordline 27, blood ingredients start to be slowly separated from a low sense wordline 27 voltage by their polarization characteristics as shown in FIG. 10a. As shown in FIG. 10b, the blood ingredients are separated with larger spectrum in a higher sense wordline 27 voltage.

Since the magnetic density of adjacent magnetic materials of the fixed ferromagnetic layer 30 and the free ferromagnetic layer 28 is differentiated depending on voltage values of the sense wordline 27, different sensing resistance values are sensed. The blood ingredient analysis means measures different sensing resistance values in the magnetization pair detection sensor to analyze the blood ingredients quantitatively.

Figure 11A:
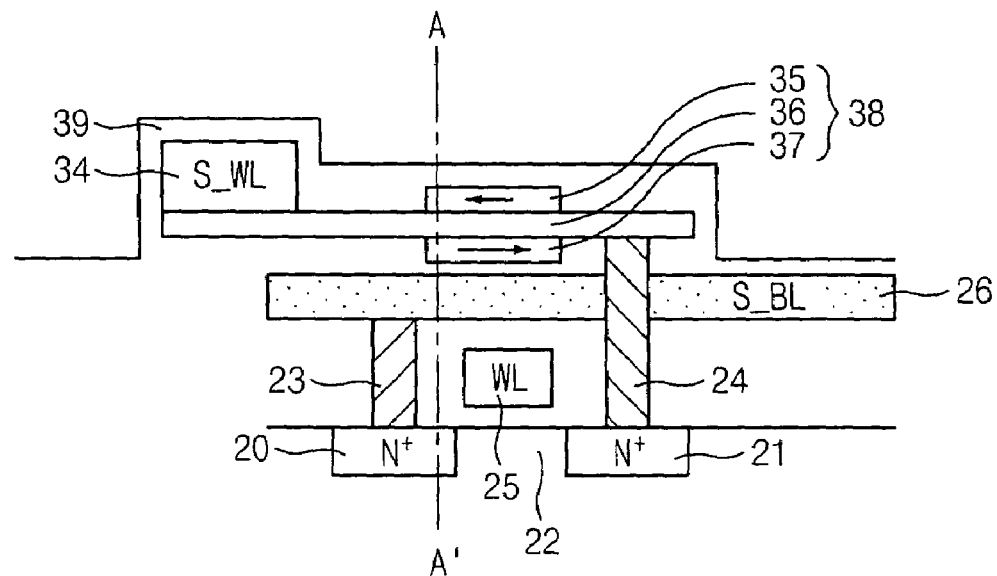
FIGS. 11a to 11c are structural diagrams illustrating a magnetization pair detection sensor using a GMR device according to an embodiment of the present invention.
Figure 11B:
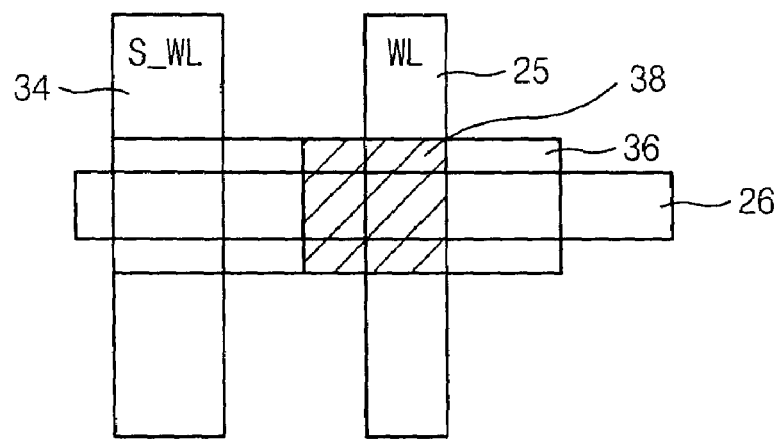

FIG. 11a is a structural diagram illustrating a magnetization pair detection sensor using a GMR device according to an embodiment of the present invention. FIG. 11b is a planar view diagram illustrating the magnetization pair detection sensor.

In an embodiment, the magnetization pair detection sensor comprises a switching device and a GMR device 38.

The GMR device 38 comprises a free ferromagnetic layer 35, a conductive resistor 36 and a fixed ferromagnetic layer 37.

The switching device comprises a NMOS transistor. The NMOS transistor comprises a drain 20 connected to a sense bitline 26 through a contact line 23, a gate 20 connected to a wordline 25 and a source 21 connected to an electrode of the conductive resistor 36 of the GMR device 38 through a contact line 24.

A sense wordline 34 is connected to the other electrode of the conductive resistor 36 of the GMR device 37. The whole device is insulated by an oxide protective layer 39.

Figure 11C:
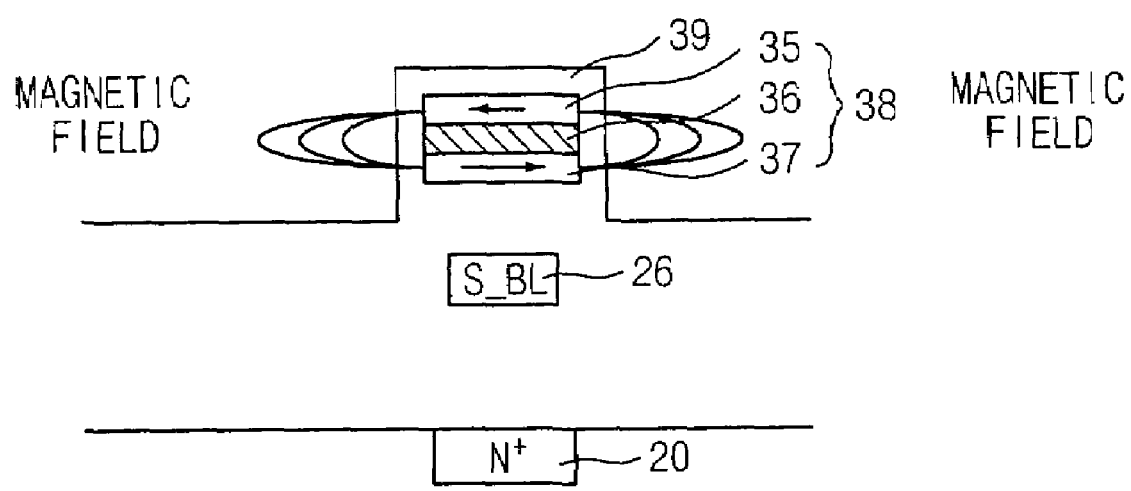

FIG. 11c is a cross-sectional diagram illustrating the magnetization pair detection sensor using the GMR device 38 when the magnetization pair detection sensor is cross-sected along line A–A'.

When magnetic field lines of the fixed ferromagnetic layer 37 are transmitted into the free ferromagnetic layer 35, resistance values of the conductive resistor 36 are determined by the strength of the magnetic field lines differentiated depending on magnetic materials.

Figure 12A:
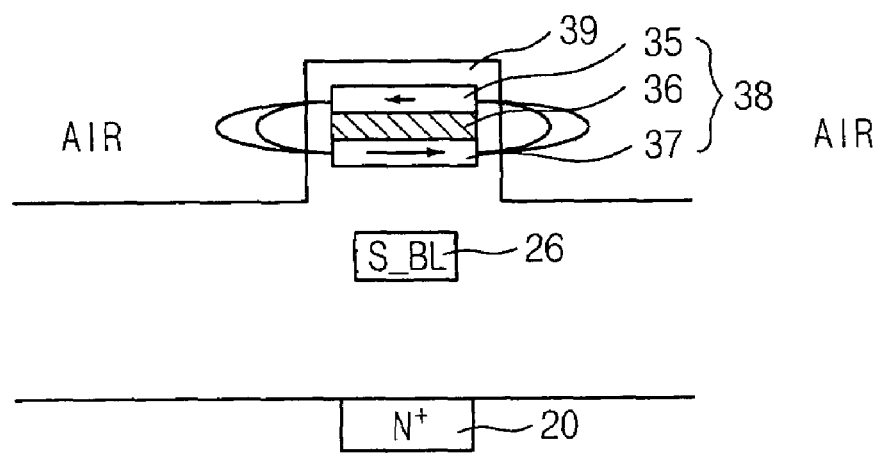
FIGS. 12a and 12b are diagrams illustrating the operational principle of the magnetization pair detection sensor of FIG. 11.
Figure 12B:
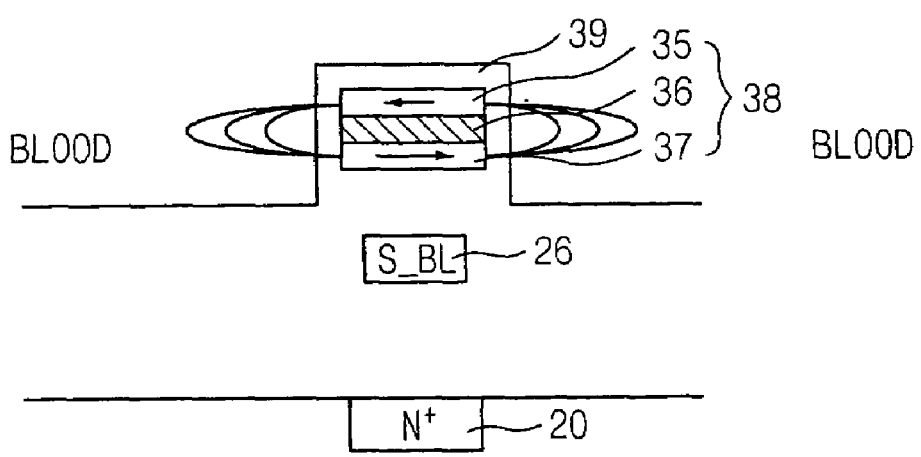

FIGS. 12a and 12b are diagrams illustrating the operation principle of the magnetization pair detection sensor of FIG. 11 using a GMR device.

As shown in FIG. 12a, when the adjacent magnetic material of the magnetization pair detection sensor is air, the free ferromagnetic layer 35 has a small magnetic density due to air having a small magnetic susceptibility. As a result, magnetoresistance is shown to be small. However, as shown in FIG. 12b, when the adjacent magnetic material of the magnetization pair detection sensor is blood, the free ferromagnetic layer 35 has a large magnetic density due to blood having a large magnetic susceptibility. As a result, magnetoresistance is shown to be large.

Figure 13A:
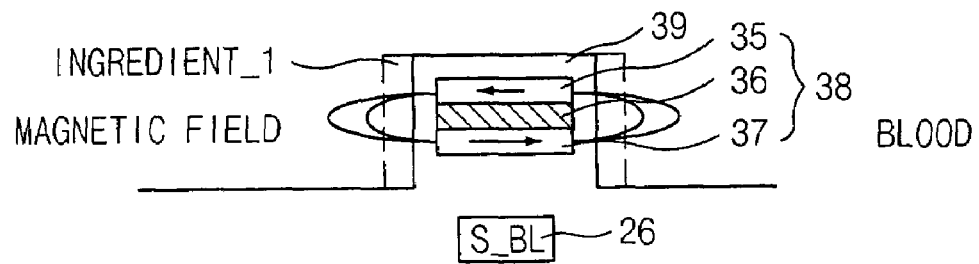
FIGS. 13a and 13b are diagrams illustrating ingredient separation depending on variations in a sense wordline voltage of the magnetization pair detection sensor of FIG. 11.
Figure 13B:
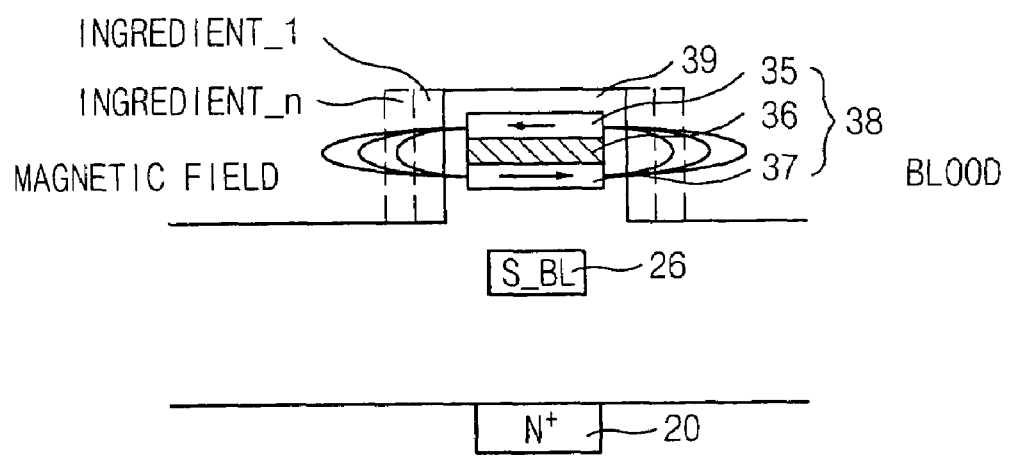

FIGS. 13a and 13b are diagrams illustrating ingredient separation depending on variations in the sense wordline voltage S_WL of the magnetization pair detection sensor of FIG. 11 using the GMR device.

When a sensing voltage is applied to the sense wordline 34, blood ingredients start to be slowly separated from a low sense wordline 34 voltage by their polarization characteristics as shown in FIG. 13a. As shown in FIG. 13b, the blood ingredients are separated with larger spectrum in a higher sense wordline 34 voltage.

Since the magnetic density of adjacent magnetic materials of the fixed ferromagnetic layer 37 and the free ferromagnetic layer 35 is differentiated depending on voltage values of the sense wordline 34, different sensing resistance values are sensed. The blood ingredient analysis means measures different sensing resistance values in the magnetization pair detection sensor to analyze the blood ingredients quantitatively.

Figure 14:
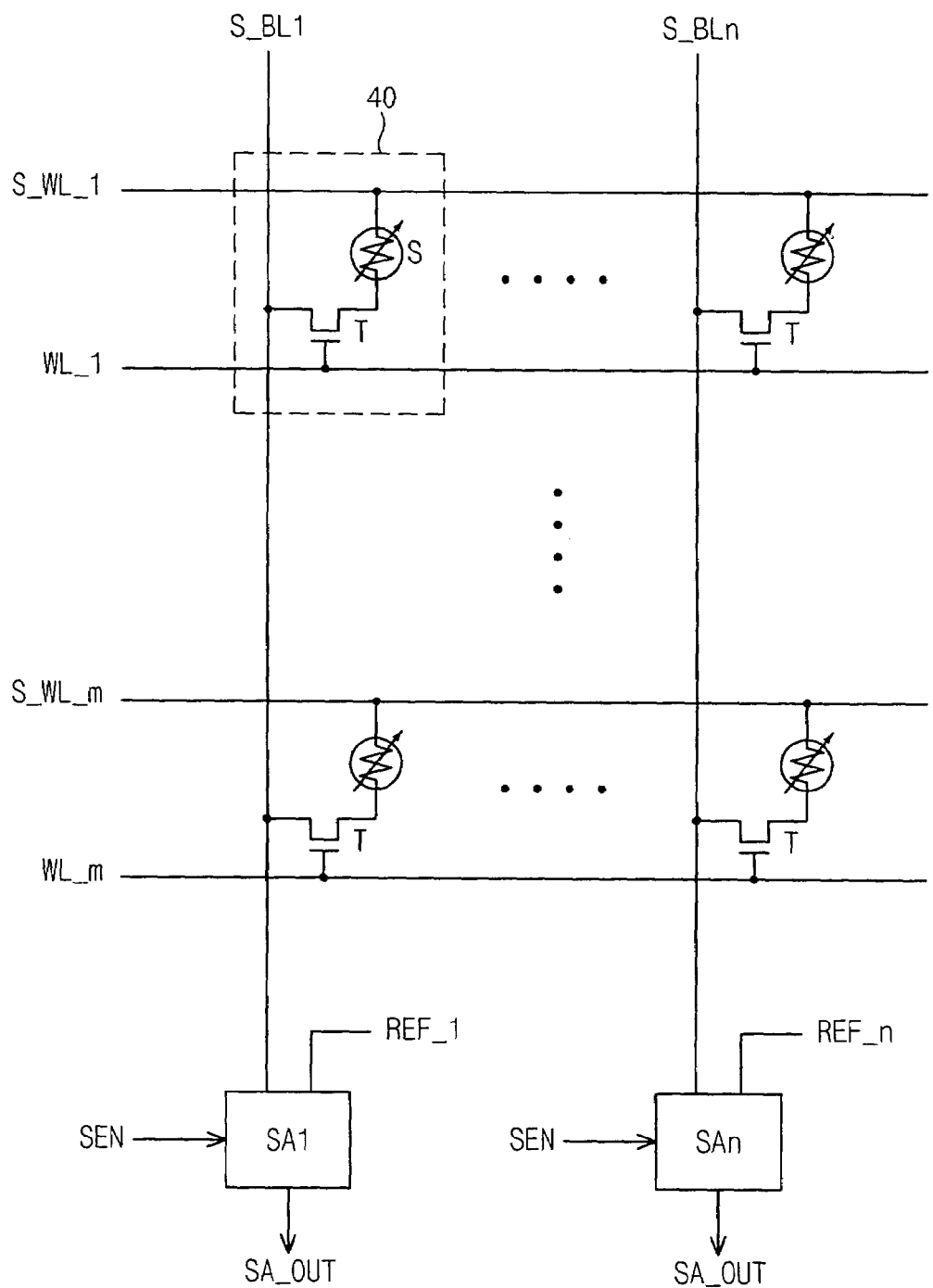
FIGS. 14 to 16 are diagrams illustrating a sensing cell array using a magnetization pair detection sensor according to an embodiment of the present invention.

FIG. 14 is a diagram illustrating a sensing cell array using a magnetization pair detection sensor according to an embodiment of the present invention.

In an embodiment, the sensing cell array using the magnetization pair detection sensor comprises a plurality of wordlines WL_1~WL_m arranged parallel to a plurality of sense wordlines S_WL_1~S_WL_m in a row direction, a plurality of sense bitlines S_BL1~S_BLn arranged perpendicular to the plurality of wordlines WL_1~WL_m and the plurality of sense wordlines S_WL_1~S_WL_m.

A plurality of magnetization pair detection sensors 40 are positionedbetween the plurality of sense wordlines S_WL_1~S_WL_m and the plurality of wordlines WL_1~WL_m intersecting the plurality of sense bitlines S_BL1~S_BLn.

The magnetization pair detection sensor 40 comprises a switching device T and a sensor S. Here, the sensor S may be a MTJ or GMR device.

The switching device T has a drain connected to the sense bitline S_BL, a source connected to a terminal of the sensor S, and a gate connected to the wordline WL. The other terminal of the sensor S is connected to the sense wordline S_WL.

The plurality of sense bitlines S_BL1~S_BLn are connected one by one to a plurality of sense amplifiers SA1~SAn. The plurality of sense amplifiers SA1~SAn receive a plurality of reference voltages REF_1~REF_n and a sense amplifier enable signal SEN, and outputs a sense amplifier output signal SA_OUT. Each of reference voltages REF_1~REF_n has different values of reference voltages.

Each column of the sensing cell array using the magnetization pair detection sensor allows blood ingredients to be separated and analyzed variously by the reference voltages REF_1~REF_n having different levels.

In this embodiment, different bias voltages are applied to the sensor S through the sense wordline S_WL. The sensor S senses values of magnetic flux density differentiatedly depending on the magnetic susceptibility of adjacent materials, and outputs different current amounts. If a gate of the switching device T receives a wordline WL voltage, the switching device T is turned on to output the different current sensed in the sensor S.

Each sense amplifier SA amplifies current applied from the sense bitline S_BL in response to a sense amplifier enable signal SEN, and outputs a sense amplifier output signal SA_OUT. The sense amplifiers SA output different sense amplifier output signals SA_OUT depending on different reference voltages REF. As a result, each row and each column of the sensing cell array using the magnetization pair detection sensor obtains characteristics of different ingredients.

Figure 15:
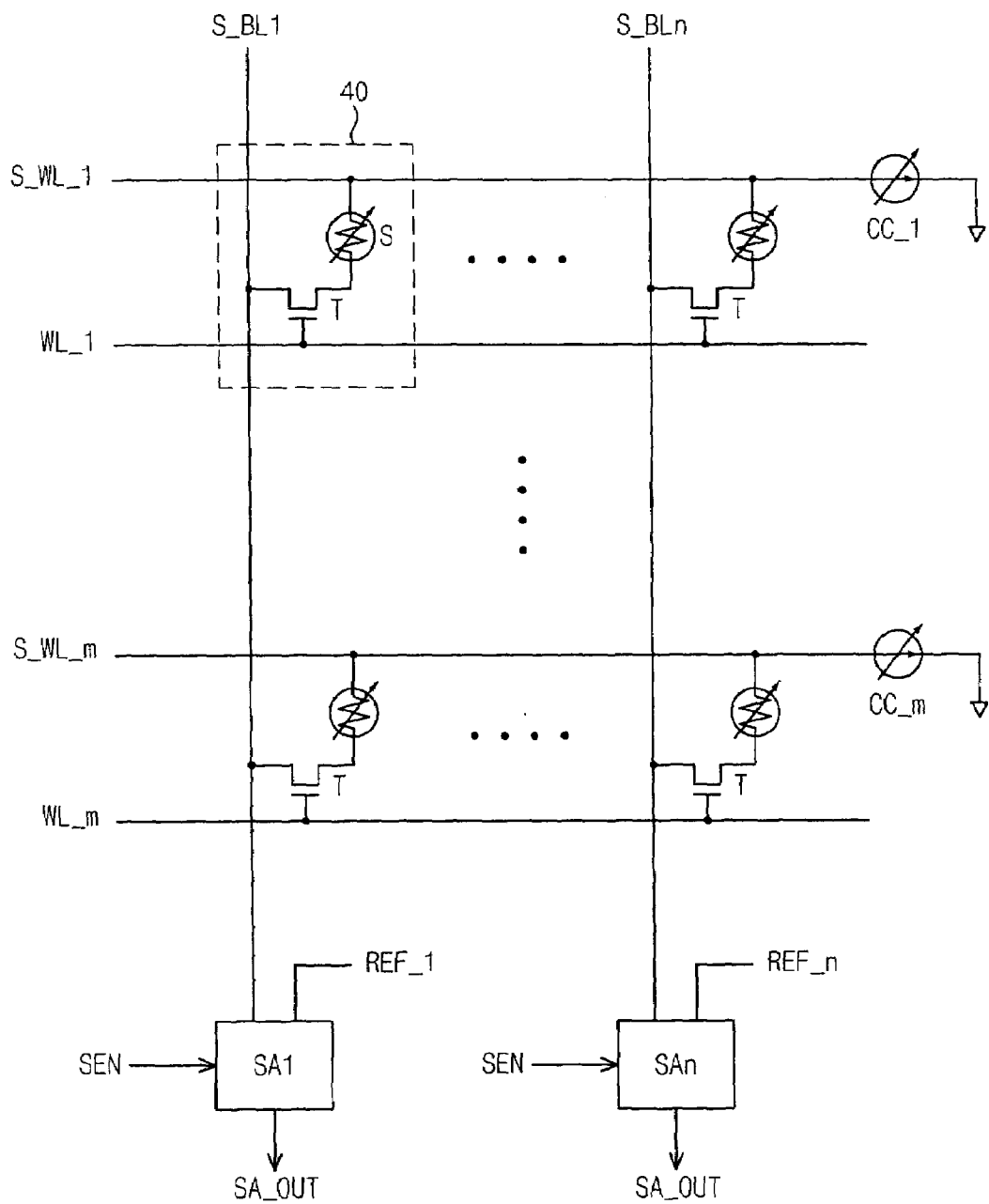

FIG. 15 is a diagram illustrating another example of a sensing cell array using the magnetization pair detection sensor.

The sensing cell array of FIG. 15 further comprises a plurality of current regulators CC_1~CC_m compared to that of FIG. 14. The current regulator CC connected between the sense wordline S_WL and a ground voltage terminal applies different currents to the ferromagnetic layers of the sensor S. As a result, the range of ingredient analysis in the sensor S is enlarged by microscopically regulating values of magnetoresistance depending on the regulation of the current applied to the sensor S as well as the voltage of the sense wordline S_WL.

Figure 16:
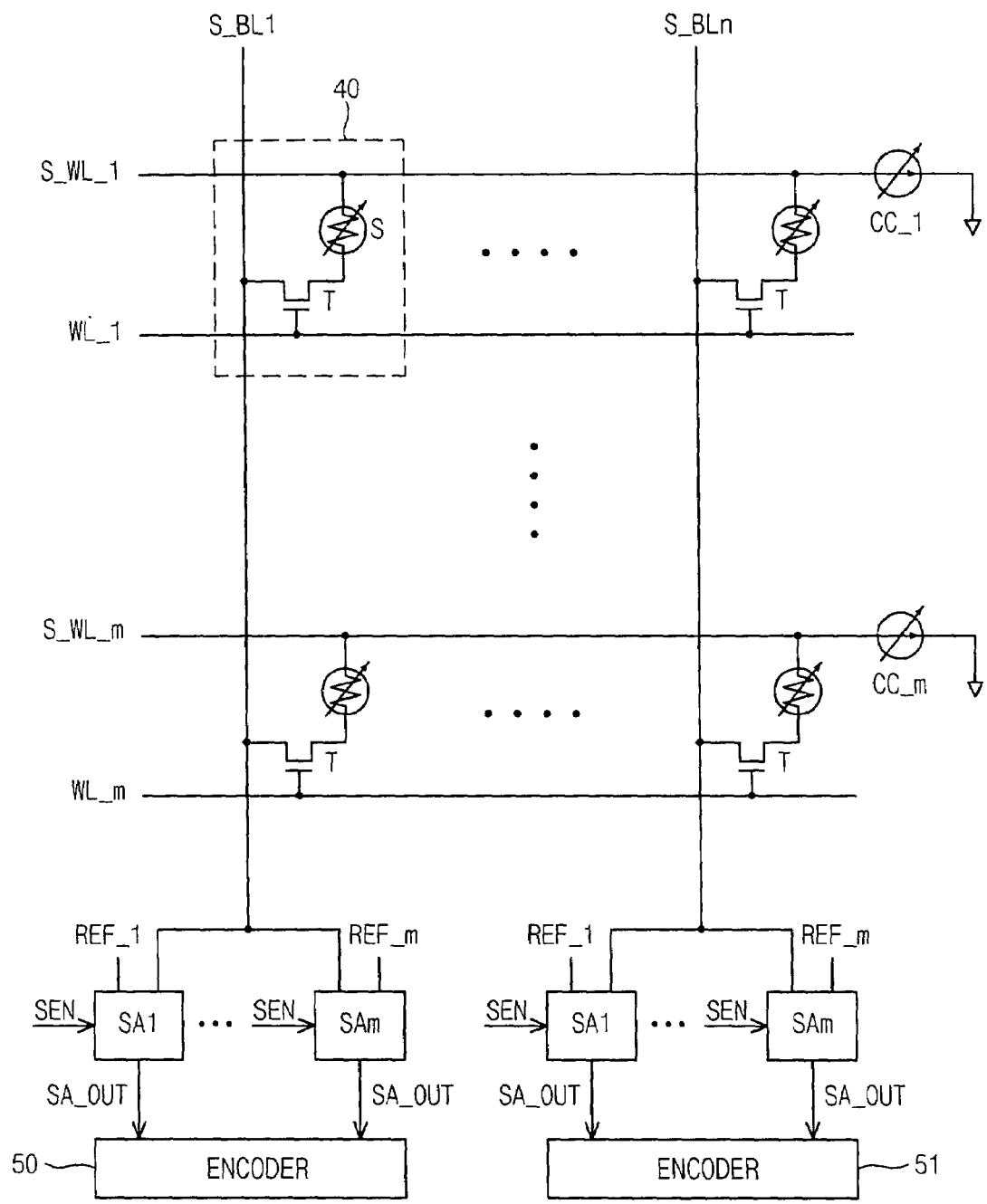

FIG. 16 is a diagram illustrating still another example of a sensing cell array using the magnetization pair detection sensor.

In the sensing cell array of FIG. 16, a sense bitline S_BL is connected to a plurality of sense amplifiers SA1~SAm. A plurality of different reference voltages REF_1~REF_m are inputted into the plurality of sense amplifiers SA1~SAm connected to the sense bitline S_BL.

A plurality of sense amplifier output signals SA_OUT from the plurality of sense amplifiers SA1~SAm are outputted into encoders 50 and 51, and encoded for analysis of ingredients of adjacent materials.

Figure 17:
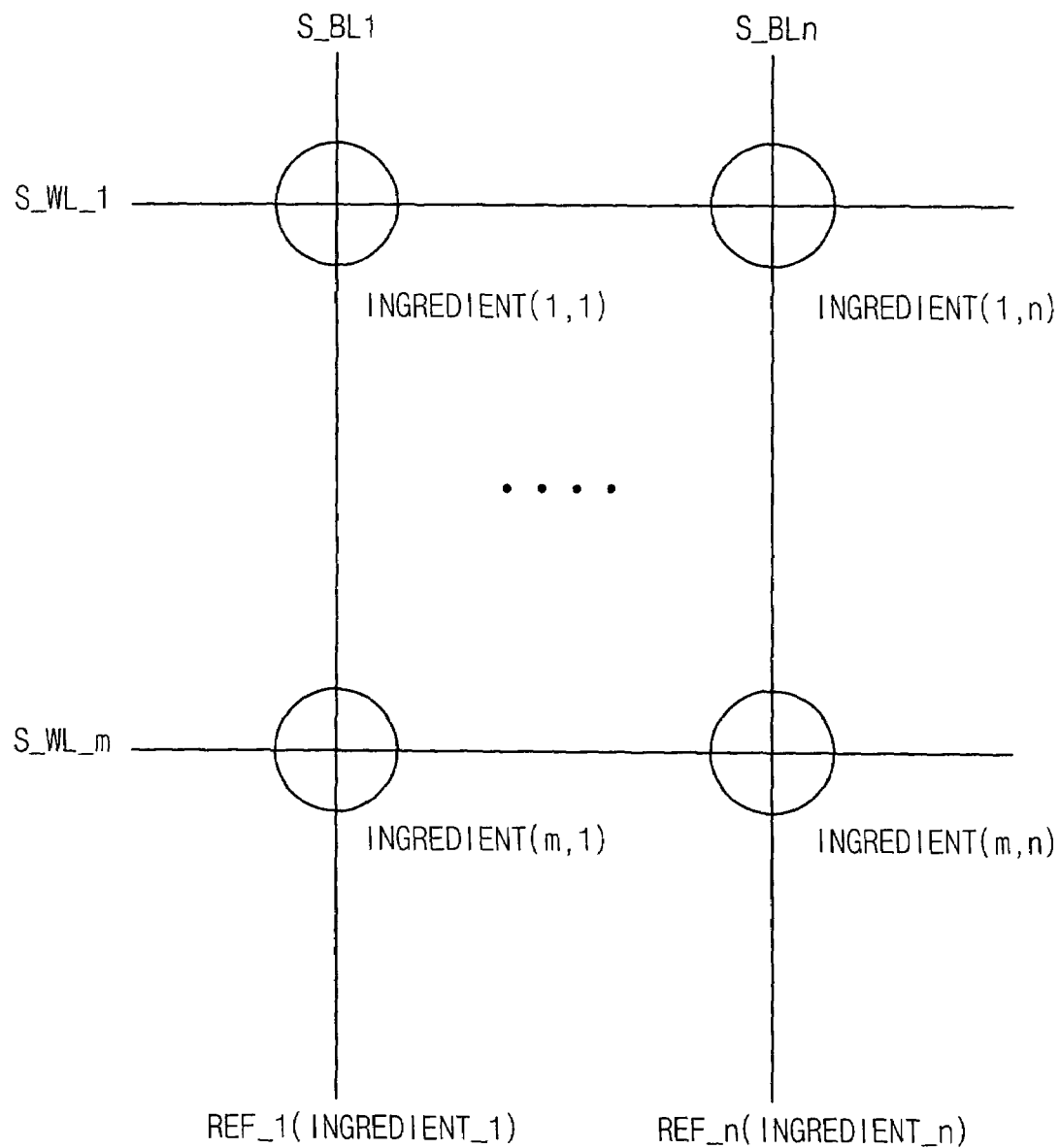
FIG. 17 is an ingredient analysis diagram illustrating a magnetization pair detection sensor according to an embodiment of the present invention.

FIG. 17 shows an ingredient analysis diagram of adjacent materials of the magnetization pair detection sensor depending on sensing output values of the sensing cell array. Ingredients of adjacent materials are separated depending on bias voltages of the plurality of sense wordlines S_WL_1~S_WL_m. Ingredients of adjacent materials in the plurality of sense bitlines S_BL1~S_BLn are separated by the plurality of different reference voltages REF_1~REF_n. As a result, the sensing cell arrays of the whole magnetization pair detection sensor separate and analyze different characteristics of adjacent materials.

Figure 18:
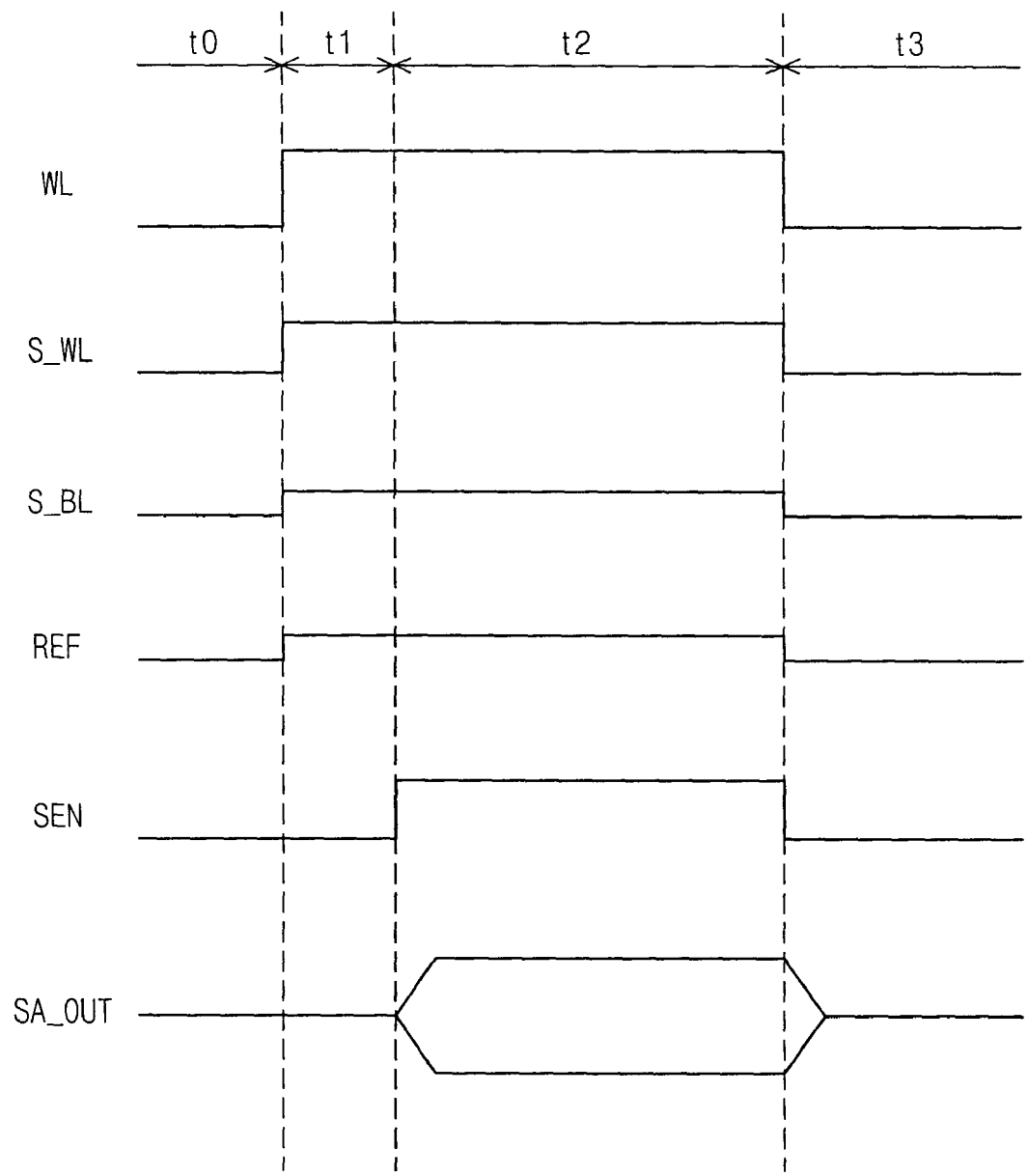
FIG. 18 is a timing diagram illustrating the operation of a sensing cell array using a magnetization pair detection sensor according to an embodiment of the present invention.

FIG. 18 is a timing diagram illustrating the operation of a sensing cell array using a magnetization pair detection sensor according to an embodiment of the present invention.

When an interval t1 starts, the wordline WL, the sense wordline S_WL, the sense bitline S_BL and the reference voltage REF are activated. As a result, the different values of magnetoresistance sensed in the sensor S are outputted to each sense amplifier SA through the sense bitline S_BL.

In an interval t2, if the sense amplifier enable signal SEN is activated, the sense amplifier SA amplifies different values of magnetoresistance to output a sense amplifier output signal SA_OUT.

As a result, the blood ingredient analysis means may analyze each sense amplifier output signal SA_OUT from the sensing cell array to analyze ingredients of adjacent materials.

When an interval t3 starts, the wordline WL, the sense wordline S_WL, the sense bitline S_BL and the reference voltage REF are inactivated. The sense amplifier enable signal SEN is disabled, and then the operation stops.

Referring to FIGS. 19a to 31, a magnetoresistive sensor and a sensing cell array using the same according to a second embodiment of the present invention are described in detail.

Figure 19A:
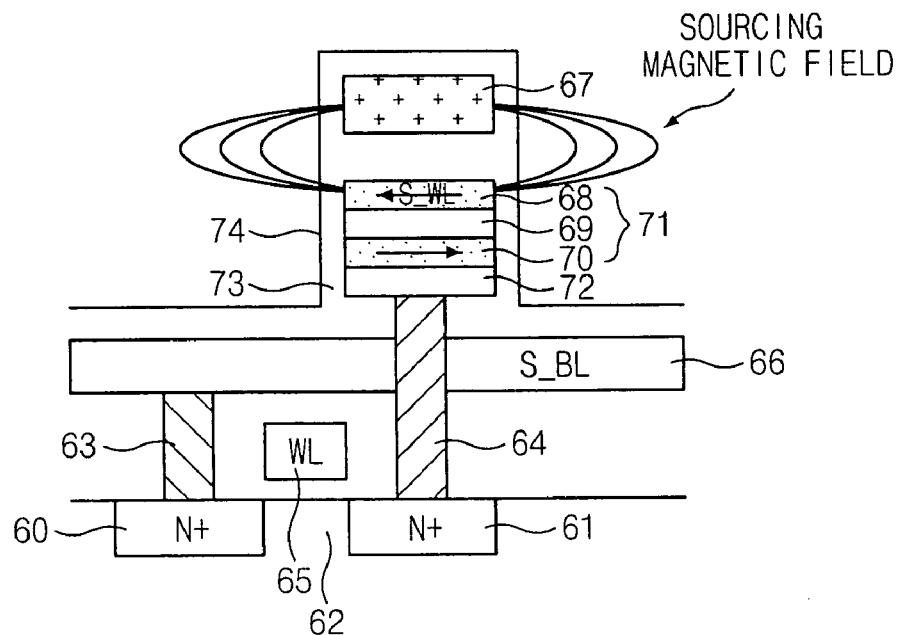
FIGS. 19a and 19b are structural diagrams illustrating a magnetoresistive sensor according to an embodiment of the present invention.
Figure 19B:
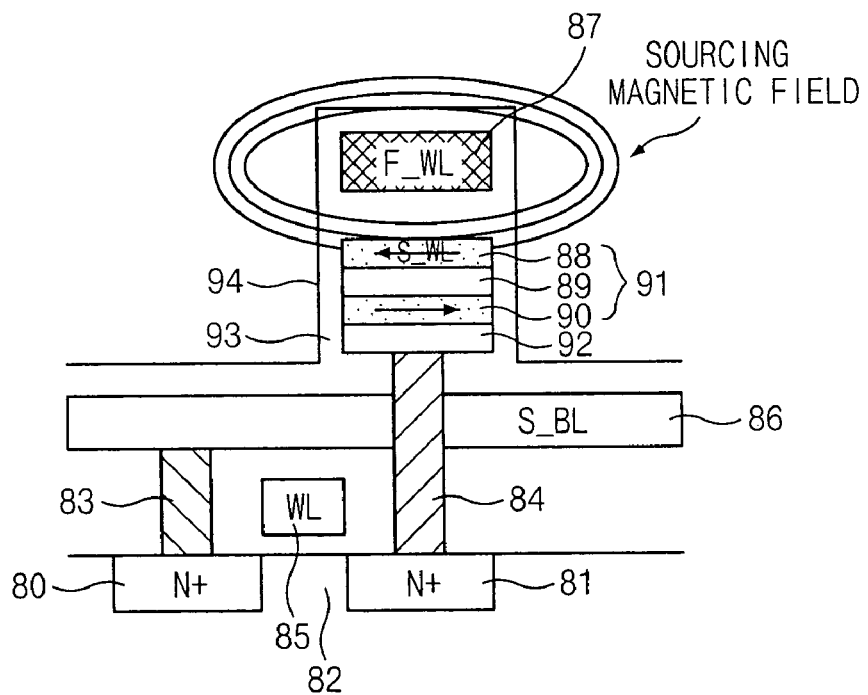

FIGS. 19a and 19b are structural diagrams illustrating a magnetoresistive sensor using a MTJ device according to an embodiment of the present invention.

FIG. 19a is a cross-sectional diagram illustrating a magnetoresistive sensor using magnetic materials.

In an embodiment, the magnetoresistive sensor comprises a switching device, a MTJ device 71 and a magnetic material 67.

The MTJ device 71 comprises a free ferromagnetic layer 68 used as a sense wordline S_WL, a tunnel junction layer 69 and a fixed ferromagnetic layer 70. The switching device comprises a NMOS transistor. A drain 60 of the NMOS transistor is connected to a sense bitline 66 through a contact line 63. A gate 62 of the NMOS transistor is connected to a wordline 65. A source 61 of the NMOS transistor is connected to a barrier conductive layer 72 formed under the MTJ device 71 through a contact line 64.

Insulating materials 73 such as oxide are isolated on the free ferromagnetic layer 68 of the MTJ device 71. The free ferromagnetic layer 68 is magnetically-coupled with the magnetic materials 67 to form a sourcing magnetic field. The whole device is isolated by an oxide protective layer 74. The magnitude of the magnetic field induced by variations of current flowing in the free ferromagnetic layer 68 used as the sense wordline S_WL is changed.

In the magnetoresistive sensor, the sourcing magnetic field between the magnetic materials 67 and the free ferromagnetic layer 68 is induced by characteristics of the magnetic materials 67 consisting of a permanent magnet even when a voltage is not applied externally. As a result, values of magnetoresistance differentiated depending on ingredients of magnetic materials formed on the magnetic field are measured.

FIG. 19b is a cross-sectional diagram illustrating a magnetoresistive sensor using a current line according to an embodiment of the present invention.

In an embodiment, the magnetoresistive sensor comprises a switching device, a MTJ device 91 and a current line 87.

The MTJ device 91 comprises a free ferromagnetic layer 88 used as a sense wordline S_WL, a tunnel junction layer 89 and a fixed ferromagnetic layer 90. The switching device comprises a NMOS transistor. The NMOS transistor has a drain 80 connected to a sense bitline 86 through a contact line 83, a gate 82 connected to a wordline 85, and a source 81 connected to a barrier conductive layer 92 formed under the MTJ device 91 through a contact line 84.

Insulating materials 93 such as oxide are isolated on the free ferromagnetic layer 88 of the MTJ device 91. The free ferromagnetic layer 88 is magnetically-coupled with the current line 87, which is used as a forcing wordline F_WL, to form a sourcing magnetic field. The whole device is isolated by an oxide protective layer 94.

The magnitude of themagnetic fields induced around the forcing wordline F_WL by the strength of current flowing therein and by the variation of current flowing in the free ferromagnetic layer 88 used as a sense wordline S_WL are changed.

In the mangetoresistive sensor, the sourcing magnetic field between the free ferromagnetic layer 88 and the current line 87 is induced only when the current line 87 has a current source. As a result, values of magnetoresistance are differentiated depending on ingredients of magnetic materials formed in the magnetic fields.

Figure 20A:
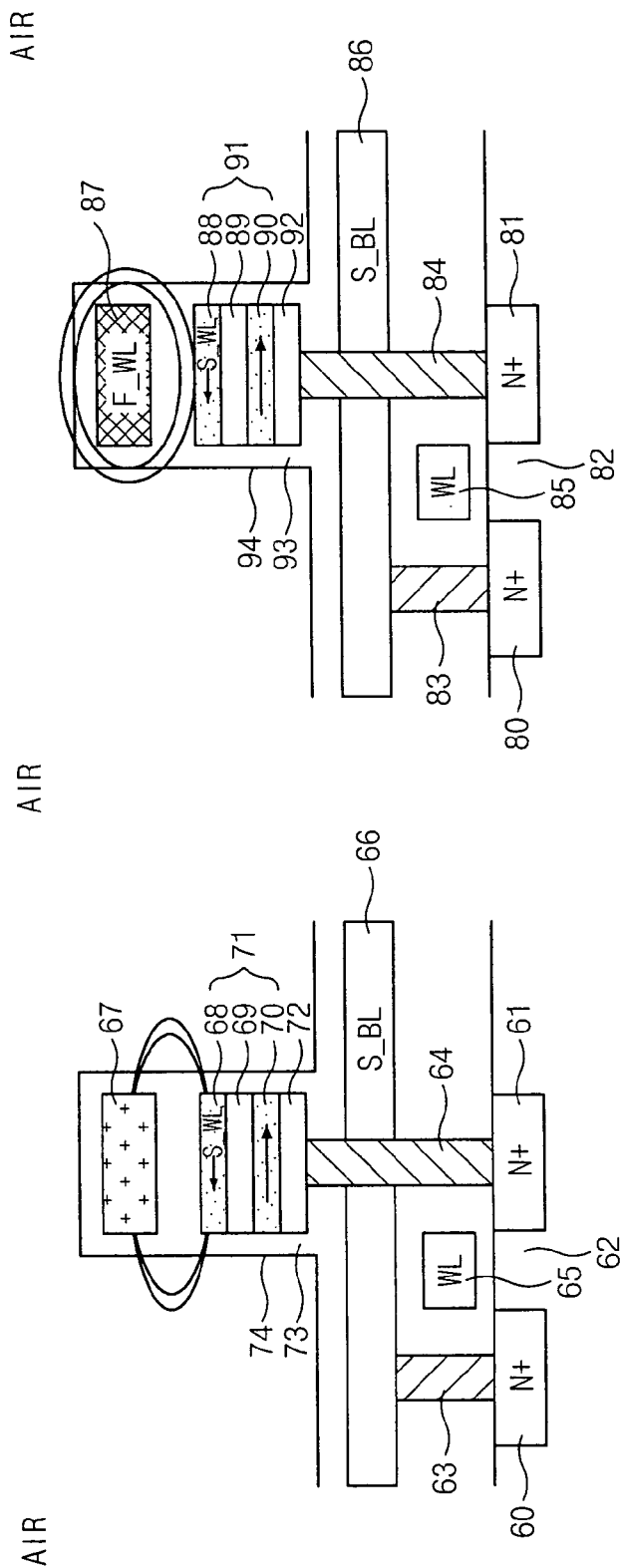
FIGS. 20a and 20b are diagrams illustrating the operational characteristics of the magnetoresistive sensor of FIG. 19.
Figure 20B:
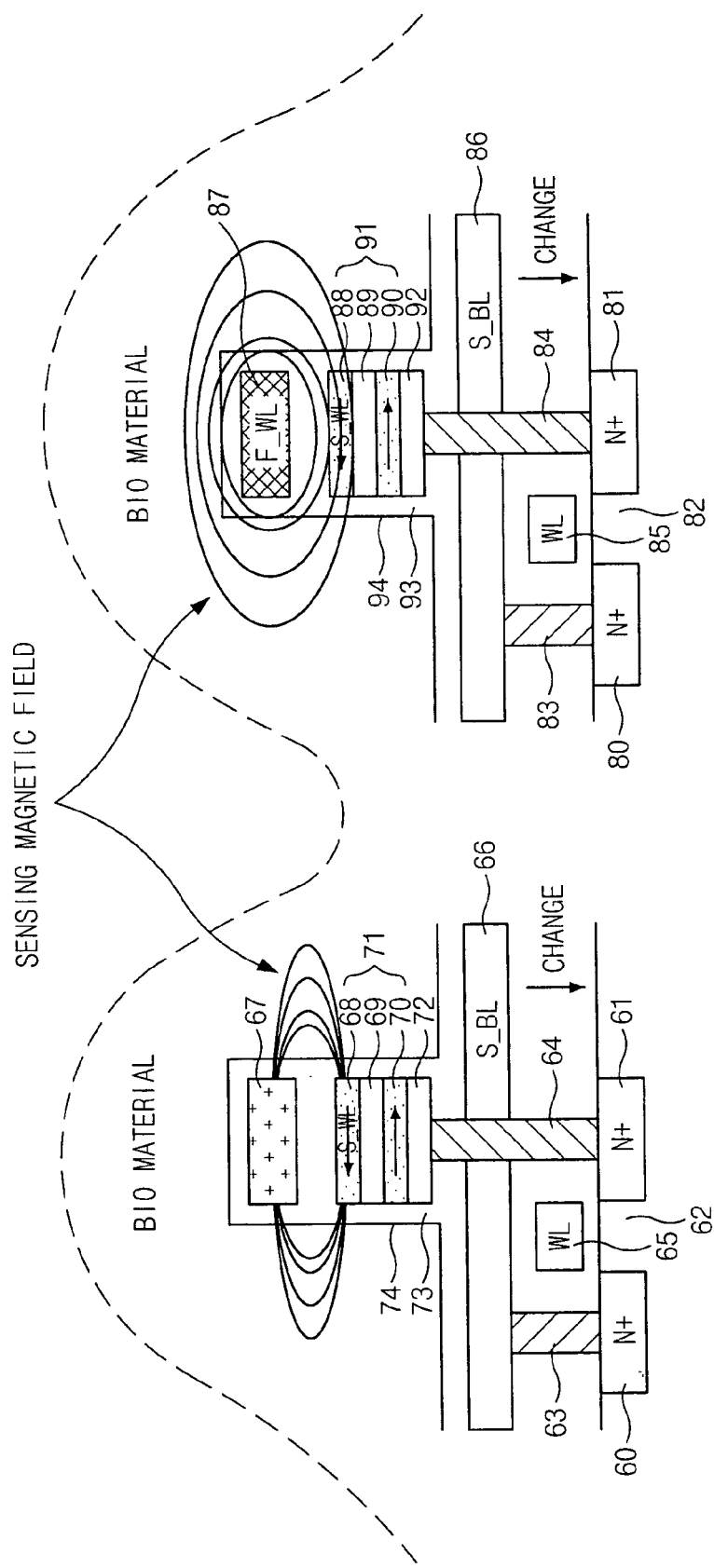

FIGS. 20a and 20b are diagrams illustrating the operational characteristics of the magnetoresistive sensor of FIG. 19.

As shown in FIG. 20a, when the adjacent magnetic material of the magnetoresistive sensor is air, the free ferromagnetic layers 68 and 88 have a small magnetic density due to air having a small magnetic susceptibility. As a result, magnetoresistance is shown to be small. However, as shown in FIG. 20b, when the adjacent magnetic material of the magnetoresistive sensor is bio-material (blood), the free ferromagnetic layers 68 and 88 have a large magnetic density due to blood having a large magnetic susceptibility. As a result, magnetoresistance is shown to be large.

Figure 21A:
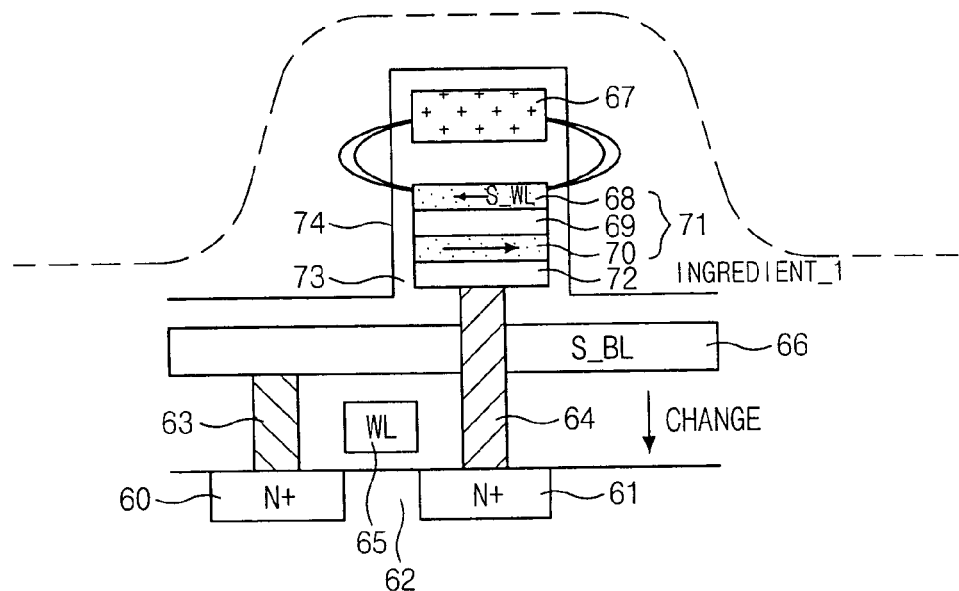
FIGS. 21a to 22b are diagrams illustrating ingredient separation depending on variations in a sense wordline voltage of the magnetoresistive sensor of FIG. 19.
Figure 21B:
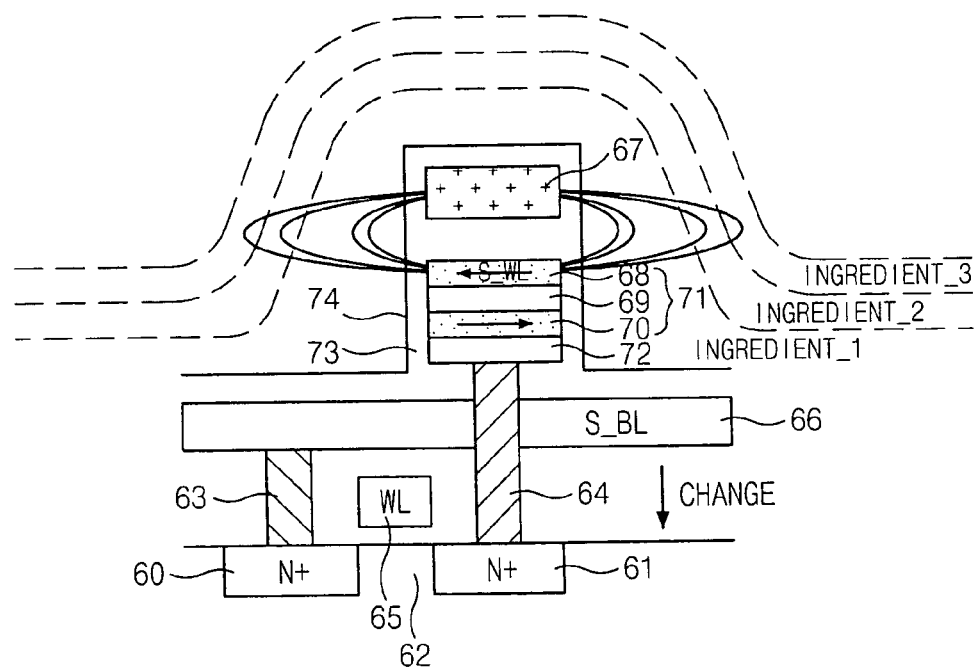

FIGS. 21a to 21b are diagrams illustrating ingredient separation depending on variations in a sense wordline S_WL voltage of the magnetoresistive sensor of FIG. 19a using magnetic materials.

When a sensing voltage is applied to a sense wordline 68, blood ingredients start to be slowly separated from a low sense wordline 68 voltage by their polarization characteristics as shown in FIG. 21a. As shown in FIG. 21b, the blood ingredients are separated with larger spectrum in a higher sense wordline 68 voltage.

Since the magnetic density of adjacent magnetic materials of the fixed ferromagnetic layer 70 and the free ferromagnetic layer 68 is differentiated depending on voltage values of the sense wordline 68, different sensing resistance values are sensed. The blood ingredient analysis means measures different sensing resistance values in the magnetoresistive sensor to analyze the blood ingredients quantitatively.

Figure 22A:
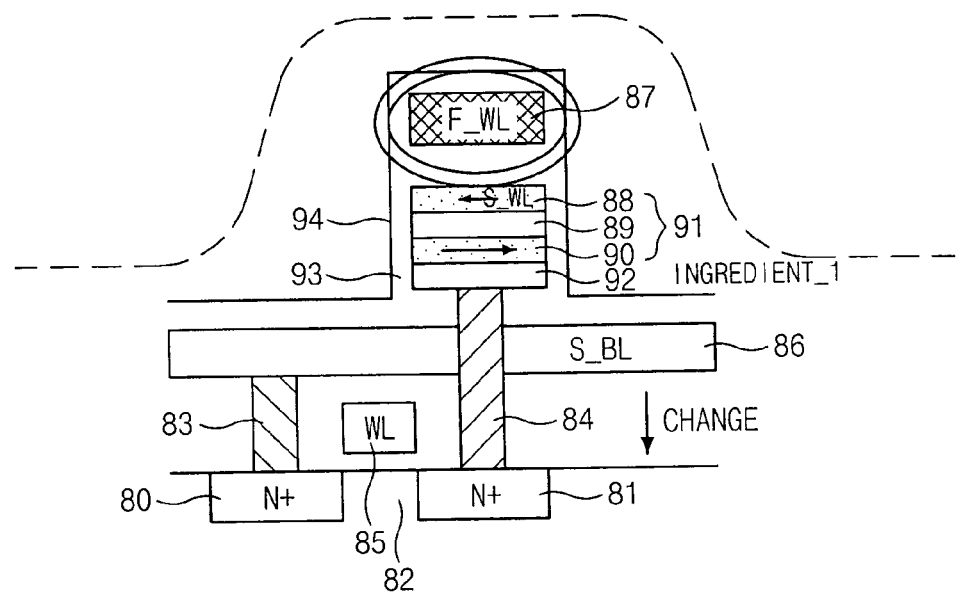
Figure 22B:
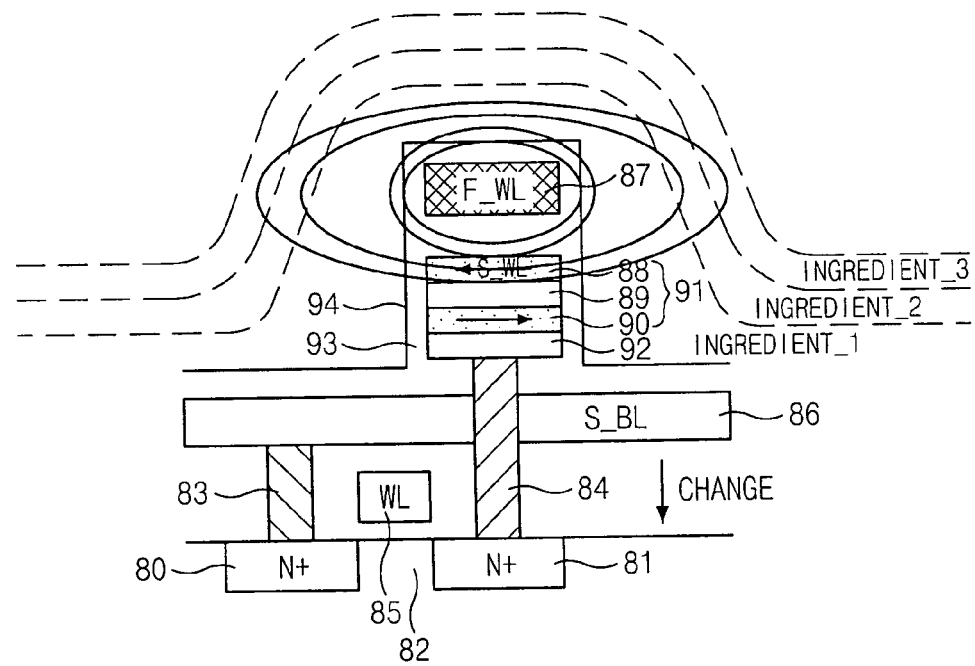

FIGS. 22a to 22b are diagrams illustrating ingredient separation depending on variations in a sense wordline S_WL (or forcing wordline) voltage of the magnetoresistive sensor of FIG. 19b using the current line.

When a sensing voltage is applied to the sense wordline 88 (or a forcing voltage is applied to the current line 87), blood ingredients start to be slowly separated from a low sense wordline 88 (or forcing wordline 87) voltage by their polarization characteristics as shown in FIG. 22a. As shown in FIG. 22b, the blood ingredients are separated with larger spectrum in a higher sense wordline 88 (or forcing wordline 87) voltage.

Since the magnetic density of adjacent magnetic materials of the fixed ferromagnetic layer 90 and the free ferromagnetic layer 88 is differentiated depending on the voltage values of the sense wordline 88 (or forcing wordline 87), different sensing resistance values are sensed. The blood ingredient analysis means measures different sensing resistance values in the magnetoresistive sensor to analyze the blood ingredients quantitatively.

Figure 23A:
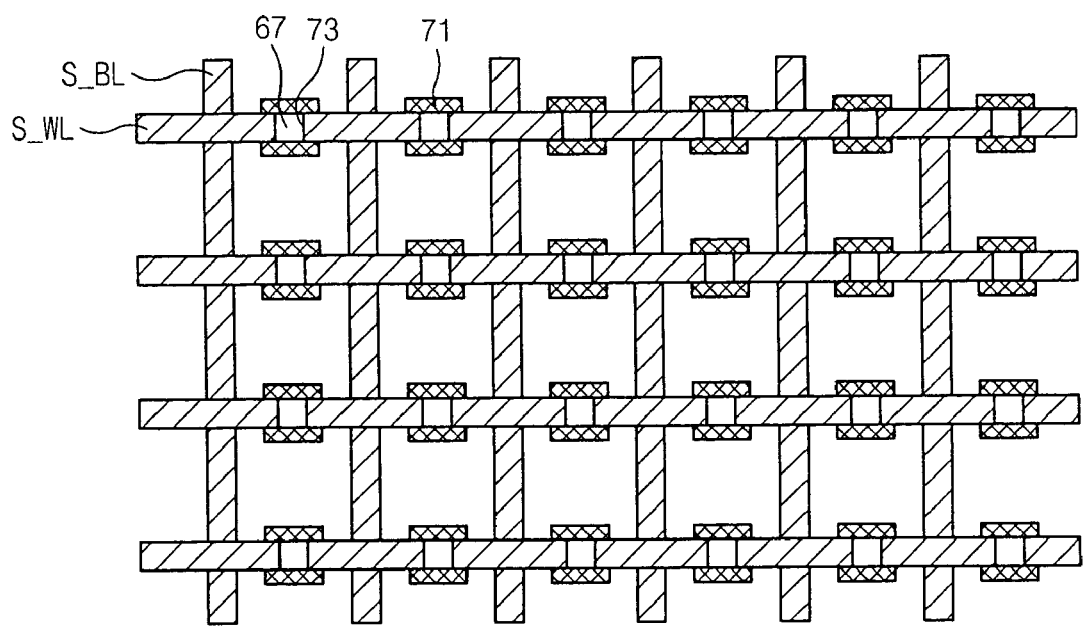
FIGS. 23a and 23b are layout diagrams illustrating the magentoresistive sensor of FIG. 19.

FIG. 23a is a layout diagram illustrating the magentoresistive sensor of FIG. 19a.

The plurality of sense wordlines S_WL formed on the MTJ devices 71 are intersecting the plurality of sense wordlines S_WL. The magnetic materials 67 are formed on portions of the sense wordlines S_WL. The insulating materials 73 such as oxide between the sense wordlines S_WL and the magnetic materials 67 isolate the sense wordline S_WL and the magnetic material 67.

Figure 23B:
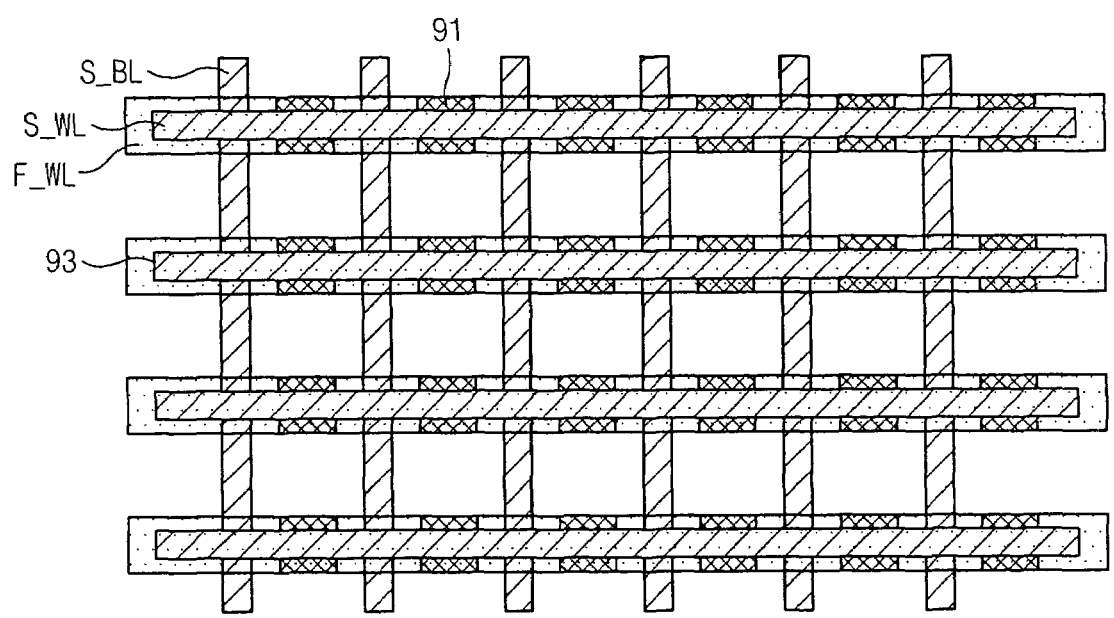

FIG. 23b is a layout diagram illustrating the magentoresistive sensor of FIG. 19b.

The plurality of sense bitlines S_BL cross the plurality of sense wordlines S_WL formed on the MTJ devices 91. The plurality of forcing wordlines F_WL are formed on the plurality of sense wordlines S_WL in parallel. Insulating materials 93 such as oxide between the sense wordlines S_WL and the forcing wordlines F_WL isolate the sense wordlines S_WL and the forcing wordlines F_WL.

Figure 24:
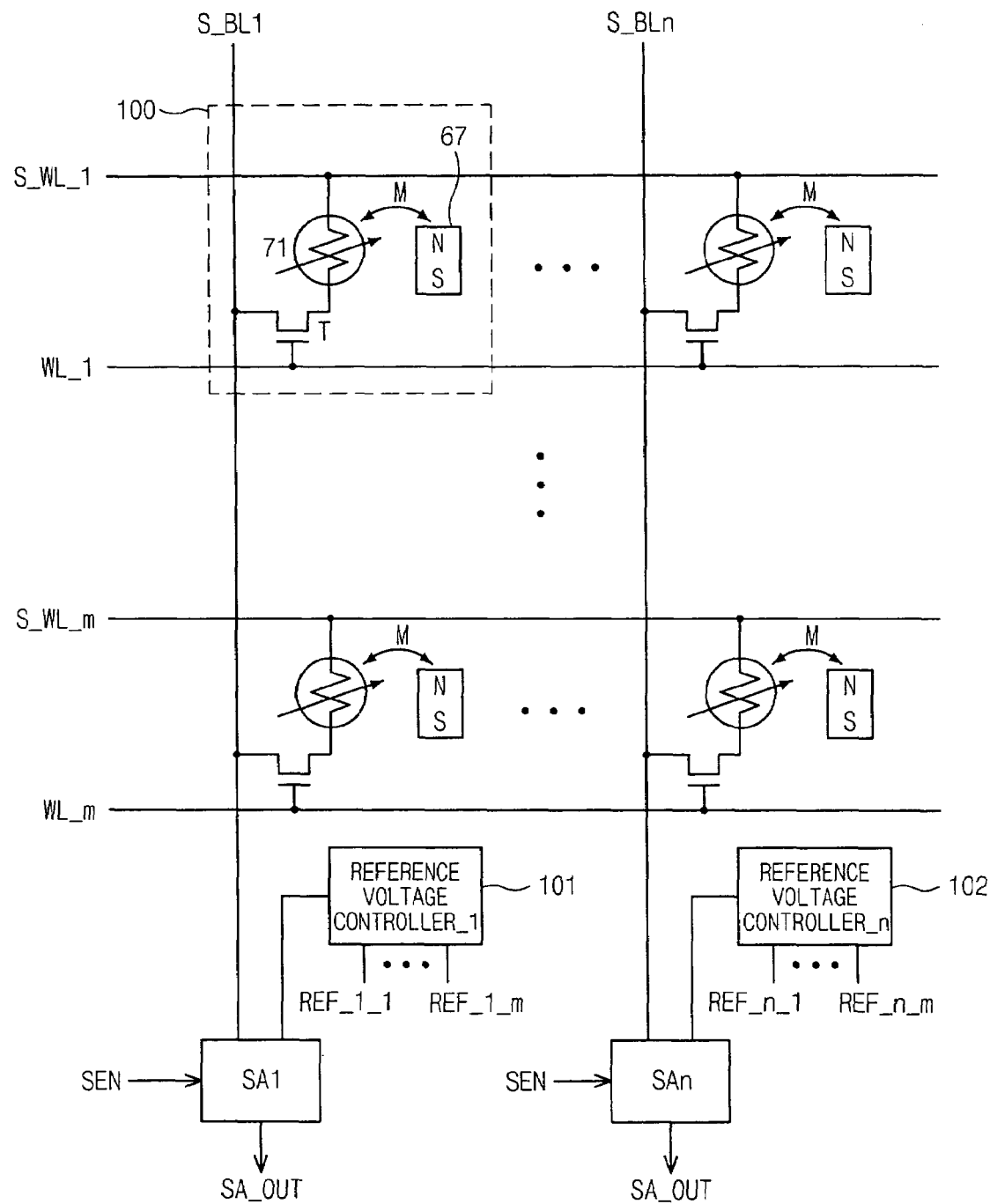
FIGS. 24 to 27 are diagrams illustrating examples of the sensing cell array using a magnetoresistive sensor according to an embodiment of the present invention.

FIG. 24 is a diagram illustrating an example of the sensing cell array using the magnetoresistive sensor of FIG. 19a.

In an embodiment, the sensing cell array using the magnetoresistive sensor comprises a plurality of wordlines WL_1~WL_m arranged parallel to a plurality of sense wordlines S_WL_1~S_WL_m in a row direction, a plurality of sense bitlines S_BL1~S_BLn arranged perpendicular to the plurality of wordlines WL_1~WL_m and the plurality of sense wordlines S_WL_1~S_WL_m in a column direction.

A plurality of magnetoresistive sensors 100 are positionedbetween the plurality of sense wordlines S_WL_1~S_WL_m and the plurality of wordlines WL_1~WL_m intersecting the plurality of sense bitlines S_BL1~S_BLn.

A magnetoresistive sensor 100 comprises a switching device T, a MTJ device 71 and a magnetic material 67. The switching device T has a drain connected to a sense bitline S_BL, a source connected to a terminal of the MTJ device 71, and a gate connected to a wordline WL. The other terminal of the MTJ device 71 is connected to the sense wordline S_WL. The MTJ device 71 forms a magnetic field M by magnetic coupling with the magnetic material 67.

The plurality of sense bitlines S_BL1~S_BLn are connected one by one to the plurality of sense amplifiers SA1~SAn. The plurality of sense amplifiers SA1~SAn comprise a plurality of reference voltage controllers 101 and 102. When a sense amplifier enable signal SEN is applied, the plurality of sense amplifiers SA1~SAn compare reference voltages REF applied from the reference voltage controllers 101 and 102 with output signals of the sense bitlines S_BL1~S_BLn to output a plurality of sense amplifier output signals SA_OUT.

The reference voltage controller 101 controls different reference voltages REF_1_1~REF_1_m to output the reference voltages into a sense amplifier SA1. The reference voltage controller 102 controls different reference voltages REF_n_1~REF_n_m to output the reference voltages into a sense amplifier SAn. Each reference voltage REF is set to have different values so that the sense amplifiers SAn may have different characteristics. In the sensing cell array using the magnetoresistive sensor, characteristics of blood ingredients are variously analyzed by different levels of the reference voltages REF.

If a different bias voltage is applied to the MTJ device 71 through the sense wordline S_WL, a magnetic field is induced by magnetic coupling with the magnetic material 67. The MTJ device 71 senses different values of magnetoresistance depending on the magnetic susceptibility of adjacent materials to output different currents. If a gate of the switching device T receives a wordline WL voltage, the switching device T is turned on. As a result, the switching device T outputs different currents sensed in the MTJ device 71 into the sense bitline S_BL.

The sense amplifier SA compares and amplifies an output signal applied from the sense bitline S_BL in response to the sense amplifier enable signal SEN with an output signal applied from the reference voltage controllers 101 and 102, and then outputs a sense amplifier output signal SA_OUT. Each row and each column of the sensing cell array using the magnetoresistive sensor obtain characteristics of different ingredients.

Figure 25:
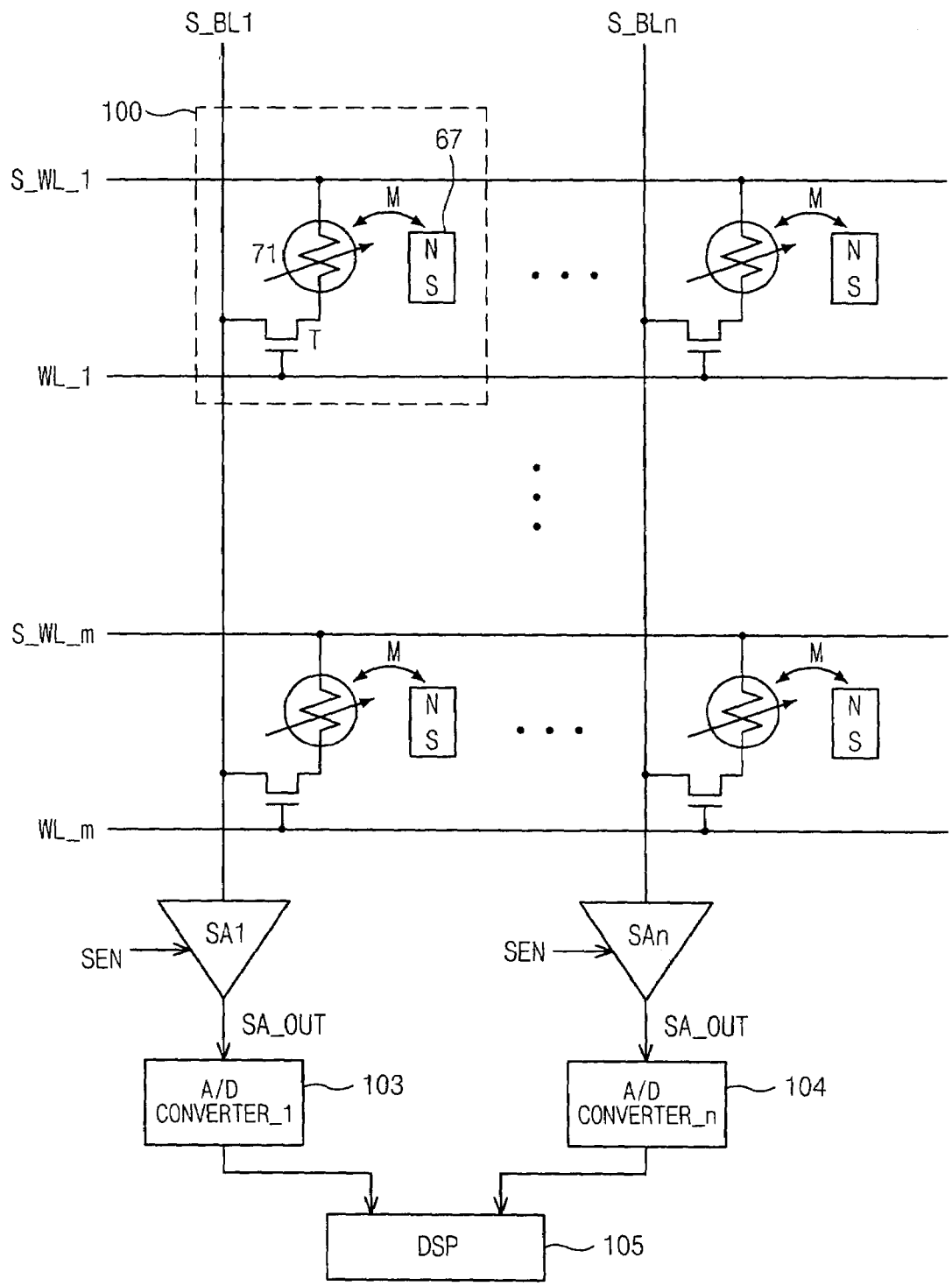

FIG. 25 is another example illustrating the sensing cell array of the magnetoresistive sensor using magnetic materials.

The sensing cell array of FIG. 25 further comprises a plurality of A/D (Analog/Digital) converters 103 and 104, and a DSP (Digital Signal Processor) 105. The AD converters 103 and 104 convert analog signals applied from each sense amplifier SA into digital signals. The DSP converts digital signals applied from each A/D converter 103 and 104 depending on digital signal processing operations. Here, the DSP 105 sets different reference voltages to enlarge the ingredient analysis range of the sensor.

Figure 26:
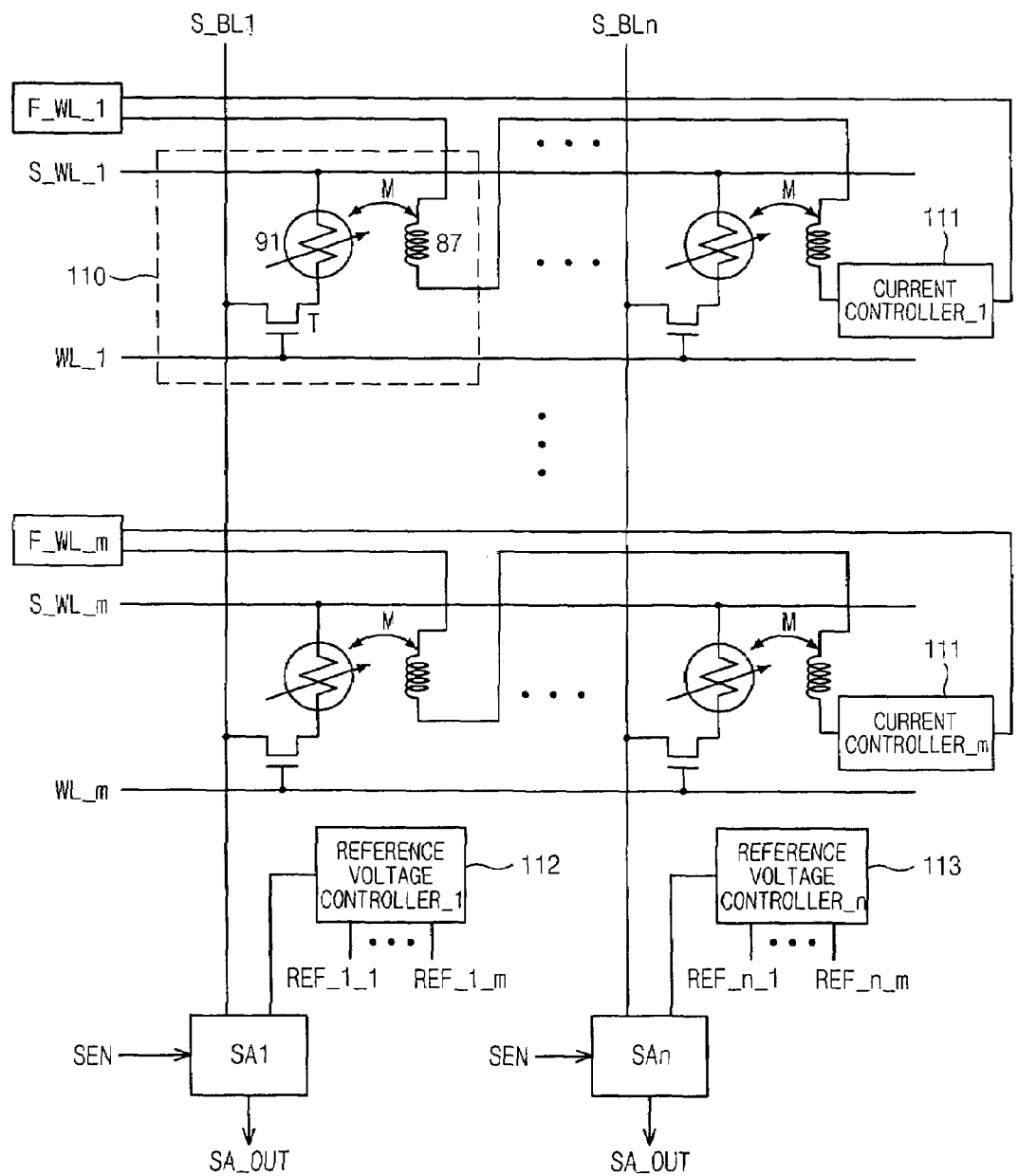

FIG. 26 is an example illustrating the sensing cell array of the magnetoresistive sensor using the current line shown in FIG. 19b.

In the sensing cell array using the magnetoresistive sensor, a plurality of wordlines WL_1~WL_m are arranged parallel to a plurality of sense wordlines S_WL_1~S_WL_m and a plurality of forcing wordlines F_WL_1~F_WL_m in a row direction. In a column direction, a plurality of sense bitlines S_BL1~S_BLn are arranged perpendicular to the plurality of wordlines WL_1~WL_m and the plurality of sense wordlines S_WL_1~S_WL_m and the plurality of forcing wordlines F_WL_1~F_WL_m.

A plurality of magnetoresistive sensors 110 are positioned between the plurality of wordlines WL_1~WL_m and the plurality of sense wordlines S_WL_1~S_WL_m intersecting the plurality of forcing wordlines F_WL_1~F_WL_m and the plurality of sense bitlines S_BL1~S_BLn.

The magentoresistive sensor 110 comprises a switching device T, a MTJ device 91 and a current line 87. The switching device T has a drain connected to the sense bitline S_BL, a source connected to a terminal of the MTJ device 91, and a gate connected to the wordline WL. The other terminal of the MTJ device 91 is connected to the sense wordline S_WL. The MTJ device 91 forms a magnetic field M by magnetic coupling with the current line 87. Here, the current line 87 is connected to the forcing wordline F_WL for supplying a forcing wordline voltage to induce a magnetic field. The current controller 111 controls current supplied to the forcing wordline F_WL.

In order to form a sourcing magnetic field around the current line 87, the amount of current in the sense bitline S_BL is changed and the amount of current in the forcing wordline F_WL is fixed. Also, the amount of current in the sense bitline S_BL is fixed, and the amount of current in the forcing wordline F_WL is changed.

The plurality of sense bitlines S_BL1~S_BLn are connected one by one to the plurality of sense amplifiers SA1~SAn. The plurality of sense amplifiers SA1~SAn comprise the plurality of reference voltage controllers 112 and 113. When a sense amplifier enable signal SEN is applied, the plurality of sense amplifiers SA1~SAn compare output signals from the sense bitlines S_BL1~S_BLn with reference voltages REF applied from the reference voltage controllers 112 and 113 to output sense amplifier output signals SA_OUT.

The reference voltage controller 112 receives the reference voltages REF_1_1~REF_1_m and sense amplifier enable signals SEN to output sense amplifier output signals SA_OUT. The reference voltage controller 113 receives reference voltages REF_n_1~REF_n_m and sense amplifier enable signals SEN to output sense amplifier output signals SA_OUT. Here, each reference voltage REF is set to have different values so that the sense amplifiers SA may have different characteristics. In the sensing cell array using the magnetoresistive sensor, characteristics of blood ingredients are variously analyzed by different levels of the reference voltages REF.

In an embodiment, if different bias voltages are applied to the MTJ device 91 through the sense wordline S_WL, and a forcing wordline voltage is applied through the current line 87, a magnetic field is induced by magnetic coupling. The MTJ device 91 senses different values of magnetoresistance depending on magnetic susceptibility of adjacent materials, and outputs different current. If a gate of the switching device T receives a wordline WL voltage, the switching device T is turned on to output different current sensed in the MTJ device 91 into the sense bitline S_BL.

The sense amplifier SA compares and amplifies output signals applied from the sense bitline S_BL in response to the sense amplifier enable signal SEN with output signals applied from the reference voltage controllers 112 and 113 to output sense amplifier output signals SA_OUT. As a result, each row and each column of the sensing cell array using the magnetoresistive sensor obtain characteristics of different ingredients.

Figure 27:
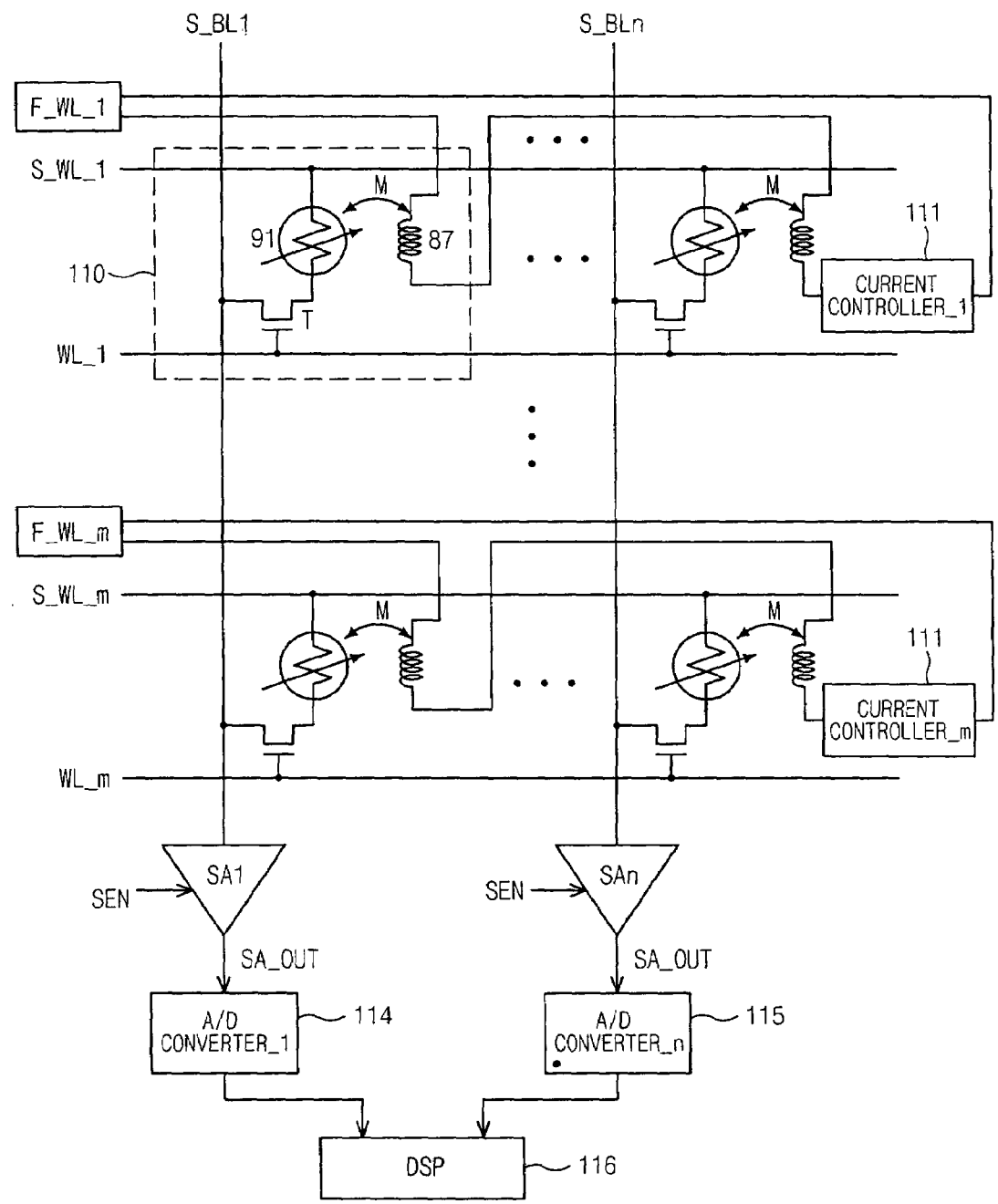

FIG. 27 is another example illustrating the sensing cell array of the magnetoresistive sensor using the current line shown in FIG. 19b.

In an embodiment, the sensing cell array of FIG. 27 further comprises a plurality of A/D (Analog/Digital) converter 114 and 115, and a DSP (Digital Signal Processor) 116. The A/D converters 114 and 115 convert analog signals applied from each sense amplifier SA into digital signals. The DSP 116 converts signals applied from each A/D converter 114 and 115 depending on digital signal processing operations. Here, the DSP 116 sets different reference voltages to enlarge the ingredient analysis range of the sensor.

Figure 28:
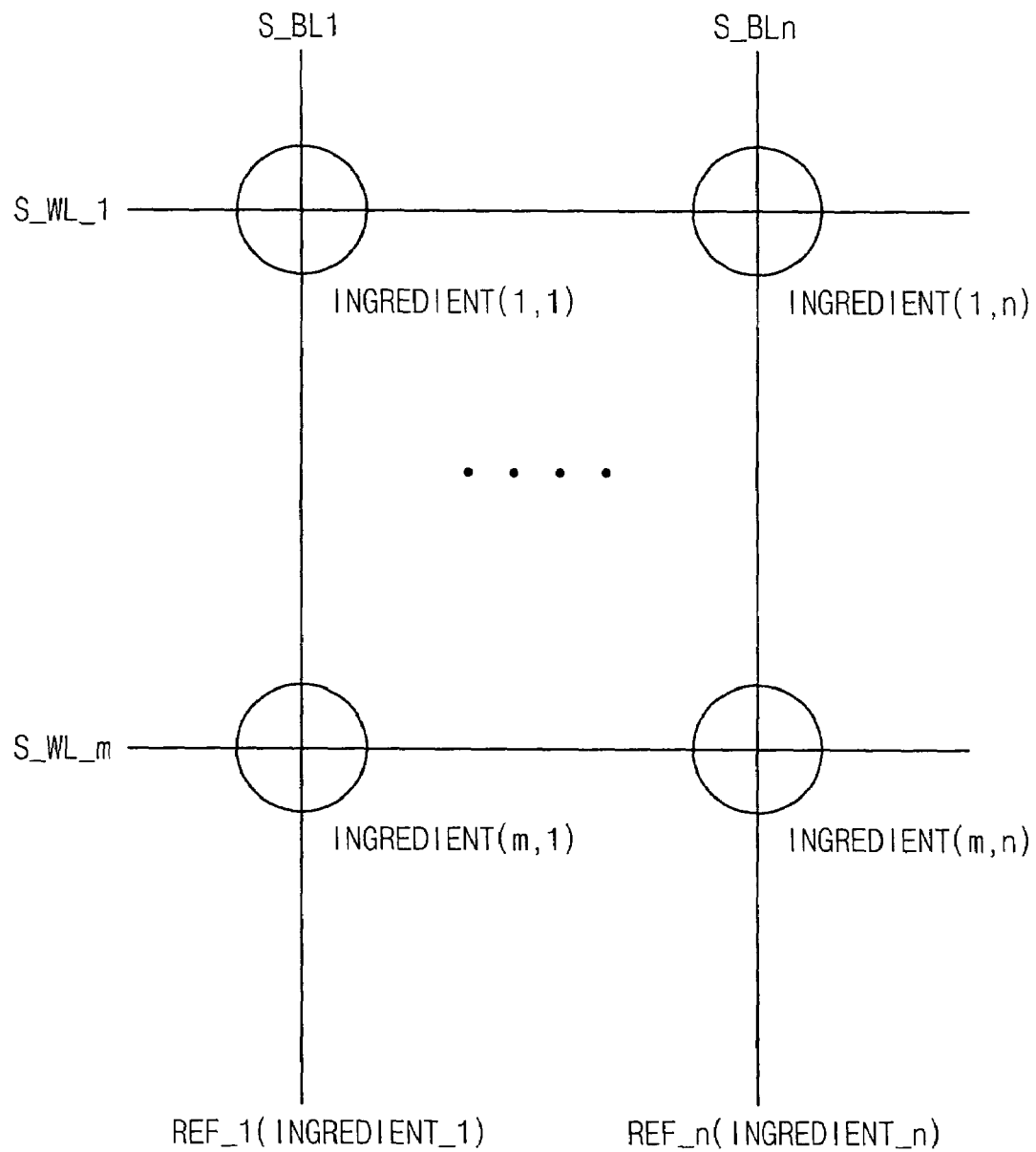
FIGS. 28 and 29 are ingredient analysis diagrams illustrating the magnetoresistive sensor according to an embodiment of the present invention.

FIG. 28 is an ingredient analysis diagram illustrating the magnetoresistive sensor using the magnetic materials depending on sensing output values.

Ingredients of adjacent materials are separated depending on bias voltages of the plurality of sense wordlines S_WL_1~S_WL_m. Ingredients of adjacent materials in the plurality of sense bitlines S_BL1~S_BLn are separated by the plurality of different reference voltages REF_1~REF_n. As a result, the sensing cell arrays of the whole magnetoresistive sensor separate and analyze different characteristics of adjacent materials.

Figure 29:
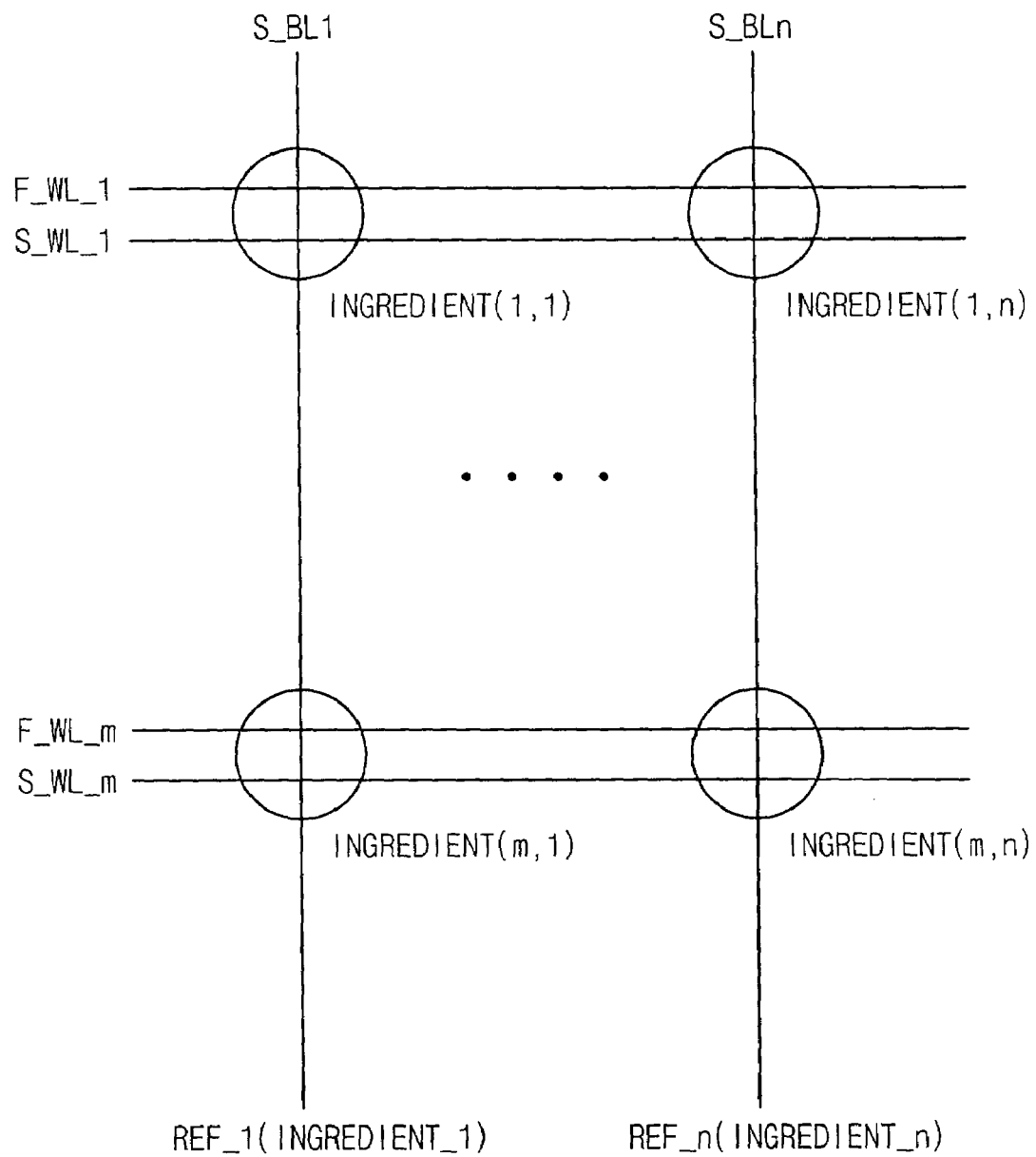

FIG. 29 is an ingredient analysis diagram illustrating the magnetoresistive sensor using the current line depending on sensing output values.

Here, ingredients of adjacent materials are separated depending on bias voltages of the plurality of sense wordlines S_WL_1~S_WL_m. Ingredients of adjacent materials are separated depending on bias voltages of the plurality of forcing wordlines F_WL_1~F_WL_m. Ingredients of adjacent materials in the plurality of sense bitlines S_BL1~S_BLn are separated by the plurality of different reference voltages REF_1~REF_n. As a result, the sensing cell arrays of the whole magnetoresistive sensor separate and analyze different characteristics of adjacent materials.

Figure 30:
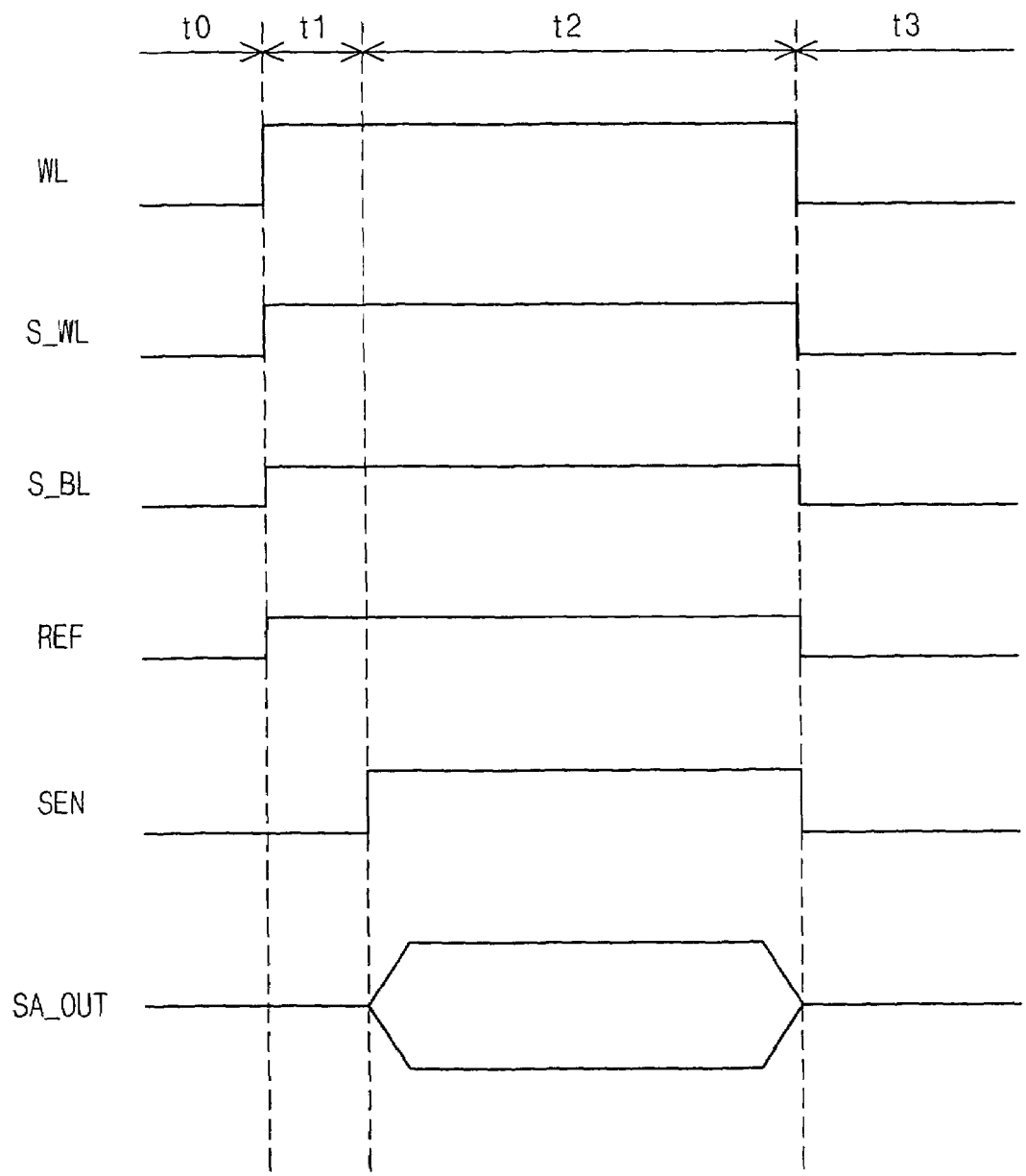
FIGS. 30 and 31 are timing diagrams illustrating the operation of the sensing cell array using the magnetoresistive sensor according to an embodiment of the present invention.

FIG. 30 is a timing diagram illustrating the read operation of the sensing cell array of the magnetoresistive sensor using magnetic materials.

When an interval t1 starts, the wordline WL, the sense wordline S_WL, the sense bitline S_BL and the reference voltage REF are activated. The different values of magnetoresistance sensed in the MTJ sensor 71 are outputted into each sense amplifier SA through the sense bitline S_BL.

In an interval t2, if the sense amplifier enable signal SEN is activated, different values of magnetoresistance sensed in the sense amplifier SA are amplified, and the sense amplifier output signal SA_OUT is outputted. As a result, the blood ingredient analysis means analyzes each sense amplifier output signal SA_OUT outputted from the sensing cell array to analyze ingredients of adjacent materials.

In an interval t3, the wordline WL, the sense wordline S_WL, the sense bitline S_BL and the reference voltage REF are inactivated. The sense amplifier enable signal SEN is disabled, and the operation stops.

Figure 31:
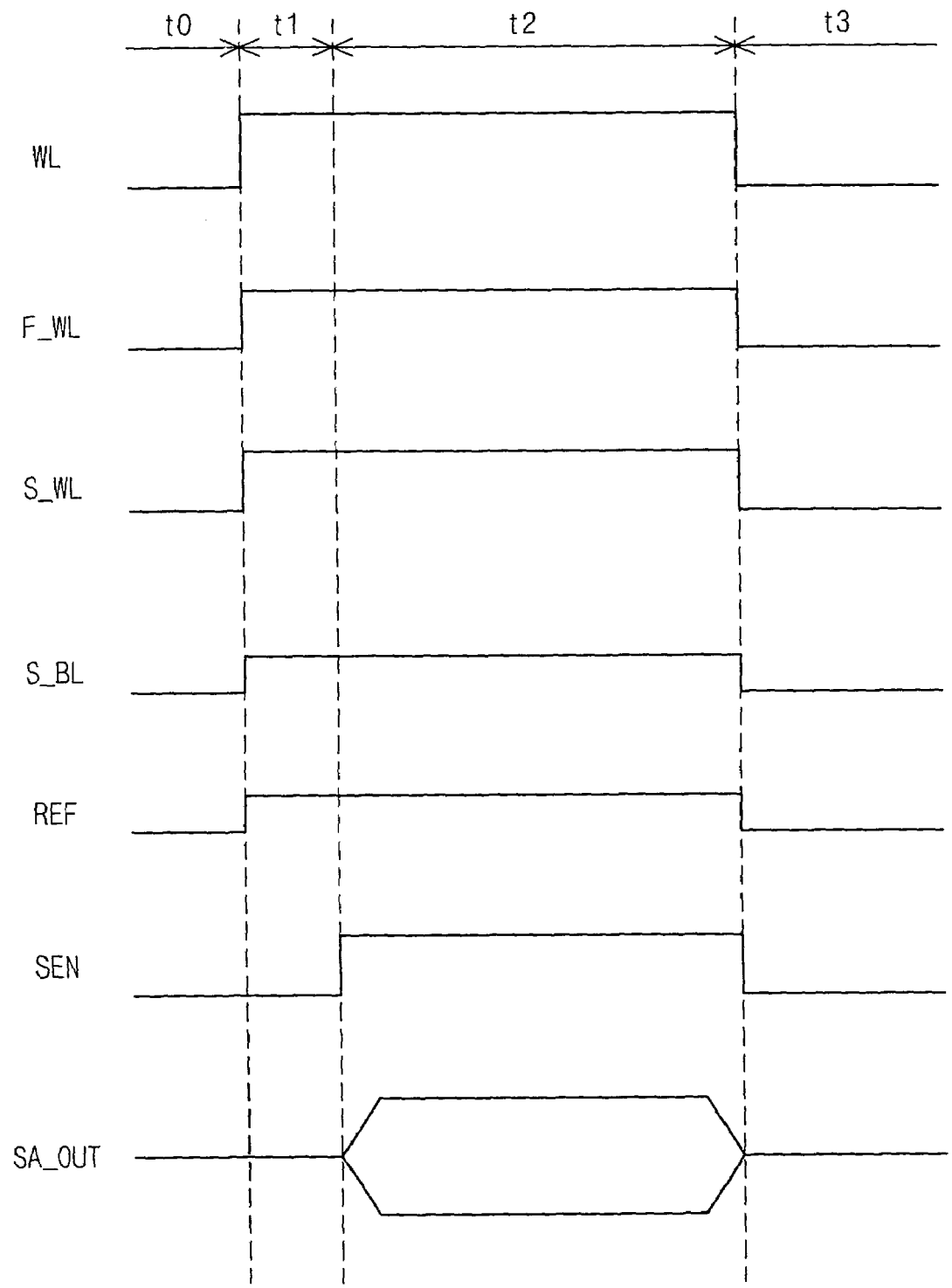

FIG. 31 is a timing diagram illustrating the read operation of the sensing cell array of the magnetoresistive sensor using the current line.

In an interval t1, the wordline WL, the forcing wordline F_WL, the sense wordline S_WL, the sense bitline S_BL and the reference voltage REF are activated. The different values of magnetoresistance sensed in the MTJ sensor 91 are outputted into each sense amplifier SA through the sense bitline S_BL.

In an interval t2, if the sense amplifier enable signal SEN is activated, different values of magnetoresistnace sensed in the sense amplifier SA are amplified, and the sense amplifier output signal SA_OUT is outputted. As a result, a blood ingredient analysis means analyzes each sense amplifier output signal SA_OUT outputted from the sensing cell array to analyze ingredients of adjacent materials.

In an interval t3, the wordline WL, the forcing wordline F_WL, thesense wordline S_WL, the sense bitline S_BL and the reference voltage REF are inactivated. Then, the sense amplifier enable signal SEN is disabled, and the operation stops.

Hereinafter, a giant magnetoresistive sensor and a sensing cell array using the same according to a third embodiment of the present invention are described referring to FIGS. 32a to 45.

Figure 32A:
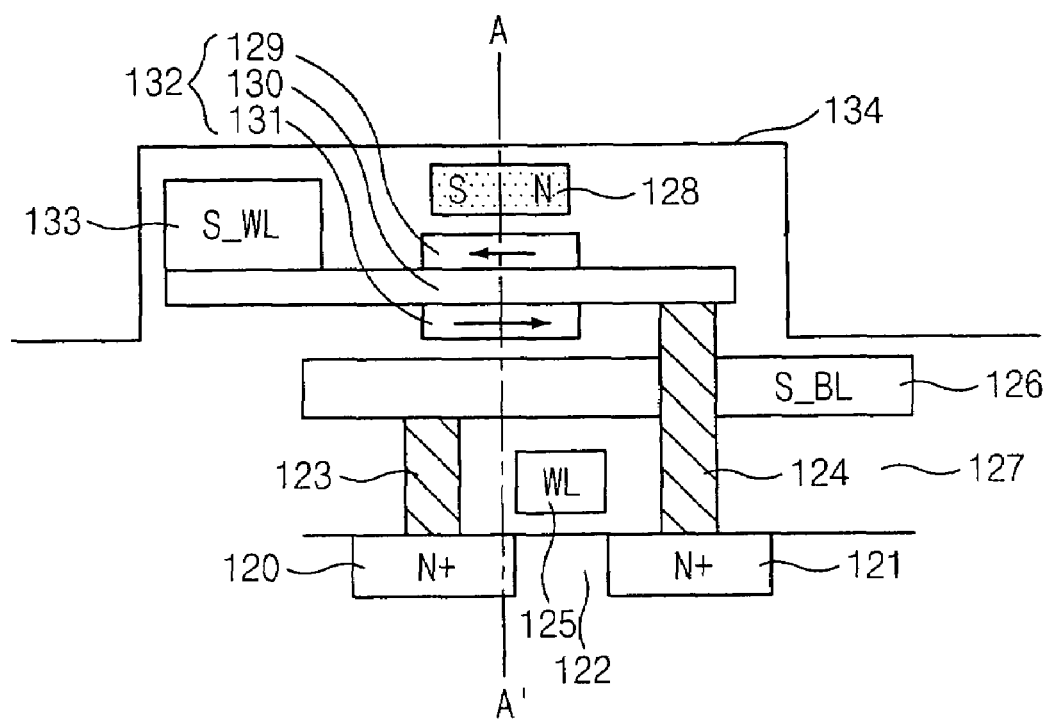
FIGS. 32a to 32c are structural diagrams illustrating a giant magnetoresistive sensor using magnetic materials according to an embodiment of the present invention.
Figure 32B:
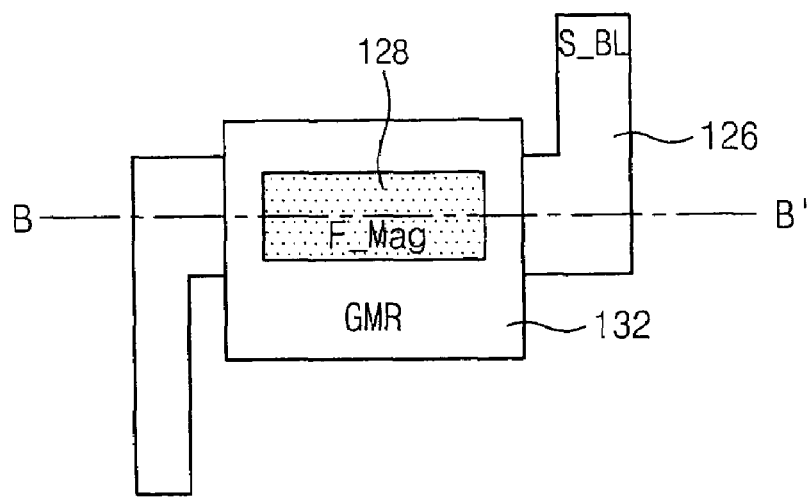
Figure 32C:
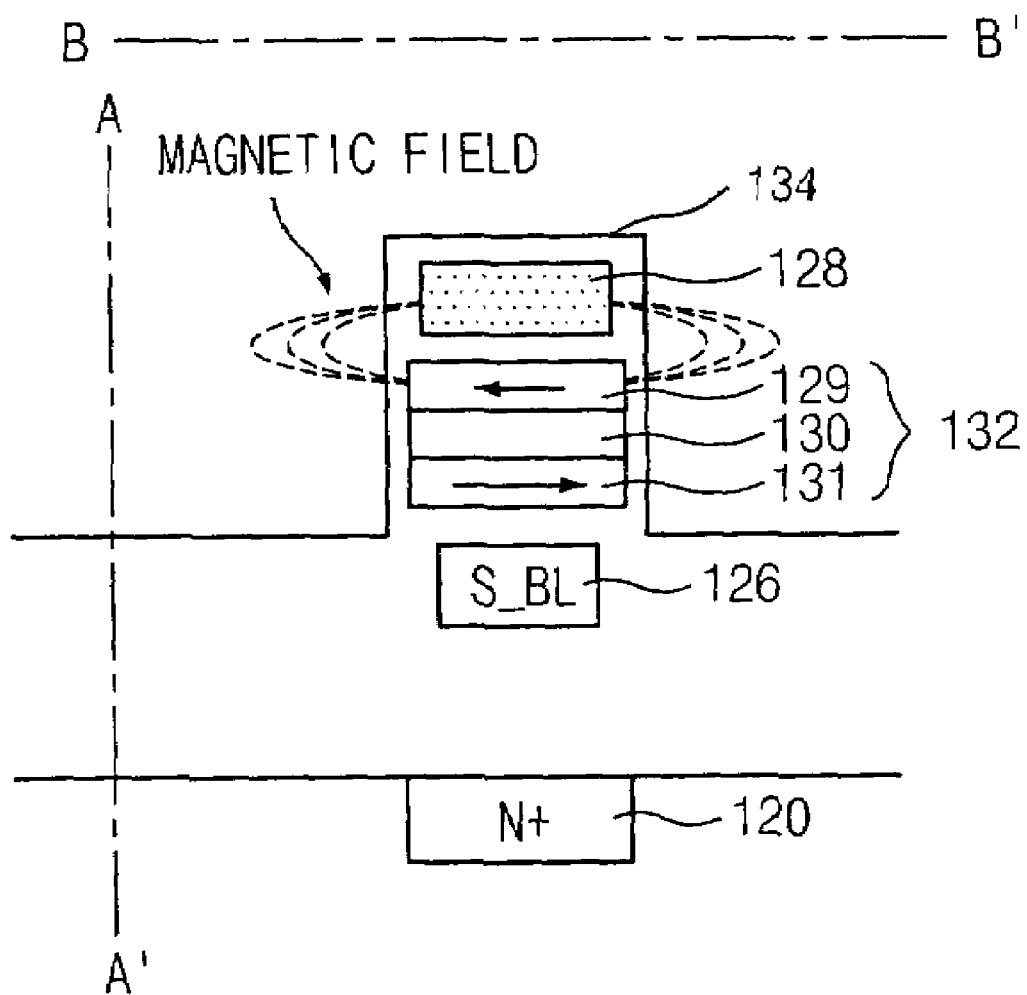

FIGS. 32a to 32c are structural diagrams illustrating a giant magnetoresistive sensor using magnetic materials according to an embodiment of the present invention.

FIG. 32a is a cross-sectional diagram illustrating a giant magnetoresistive sensor using magnetic materials.

In an embodiment, the giant magnetoresistive sensor comprises a switching device, a GMR device 132, a sense wordline 123 and a forcing magnetic material 128.

Here, the GMR device 132 comprises a free ferromagnetic layer 129, a conductive resistor 130 and a fixed ferromagnetic layer 131.

The switching device comprises a NMOS transistor. The NMOS transistor has a drain 120 connected to a sense bitline 126 through a contact line 123, a gate 122 of the switching device connected to a wordline 125, and a source 121 connected to a portion of the conductive resistor 130 through a contact line 124. A sense wordline 133 is formed on the other portion of the conductive resistor 130.

The device is insulated by an oxide protective layer 134. A barrier conductive layer 127 is formed under the sense bitline 126.

FIG. 32b is a plane view illustrating the giant magnetoresistive sensor using magnetic materials.

The GMR device 132 is formed on the sense bitline 126, and the magnetic material 128 is formed on the GMR device 132.

FIG. 32c is a cross-sectional diagram illustrating the giant magnetoresistive sensor using magnetic materials.

Referring to FIG. 32c, a magnetic field is formed by magnetic coupling a magnetic material 128 with the free ferromagnetic layer 129. The whole device is insulated by the oxide protective layer 134. As a result, the size of magnetic field induced by variation in voltage applied to the sense wordline 133 is changed.

In the giant magnetoresistive sensor, a magnetic field is induced between the free ferromagnetic layer 129 and the magnetic material 128 by the magnetic material 128 consisting of a permanent magnet. As a result, different values of magnetoresistance depending on ingredients of magnetic materials formed on the magnetic field are measured.

Figure 33A:
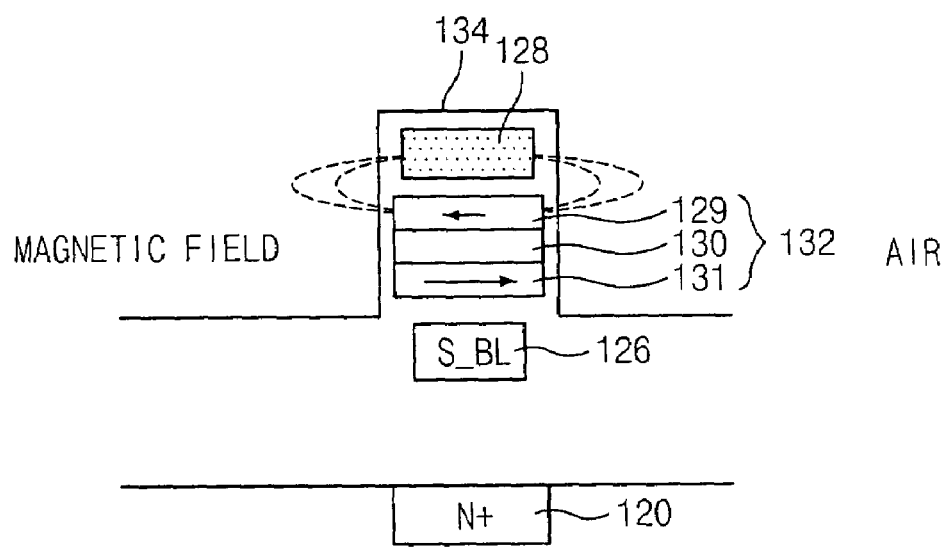
FIGS. 33a and 33b are diagrams illustrating operational characteristics of the giant magnetoresistive sensor of FIG. 32.
Figure 33B:
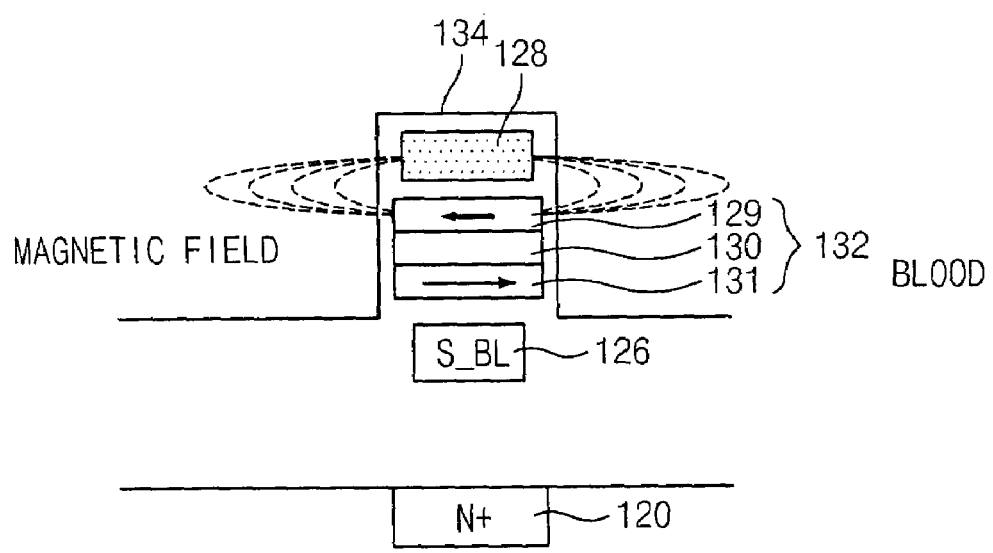

FIGS. 33a and 33b are diagrams illustrating operation characteristics of the giant magnetoresistive sensor of FIG. 32.

As shown in FIG. 33a, when the adjacent magnetic material of the magnetoresistive sensor is air, the free ferromagnetic layer 129 has a small magnetic density due to air having a small magnetic susceptibility. As a result, magnetoresistance is shown to be small. However, as shown in FIG. 33b, when the adjacent magnetic material of the magnetoresistive sensor is bio-material (blood), the free ferromagnetic layer 129 has a large magnetic density due to blood having a large magnetic susceptibility. As a result, magnetoresistance is shown to be large.

Figure 34A:
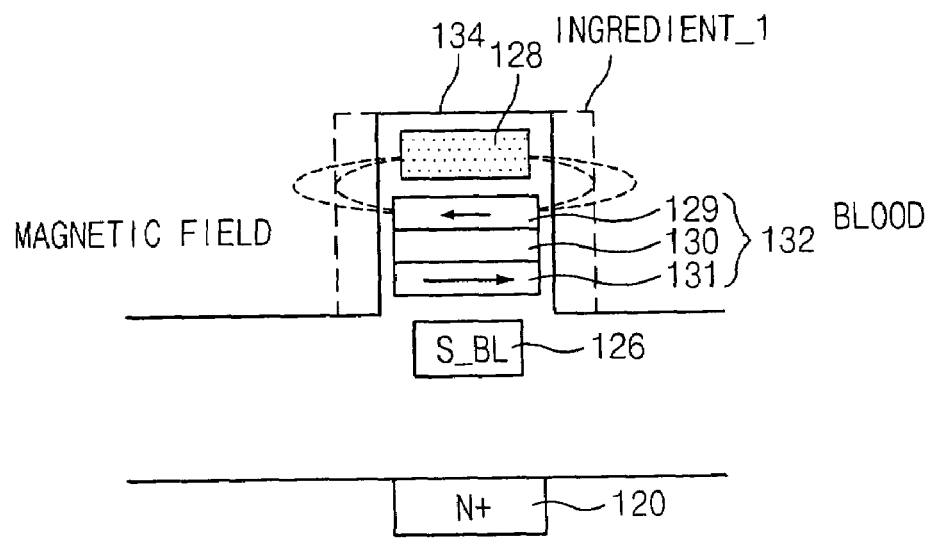
FIGS. 34a and 34b are diagrams illustrating ingredient separation depending on variations in a sense wordline voltage of the giant magnetoresistive sensor of FIG. 32.
Figure 34B:
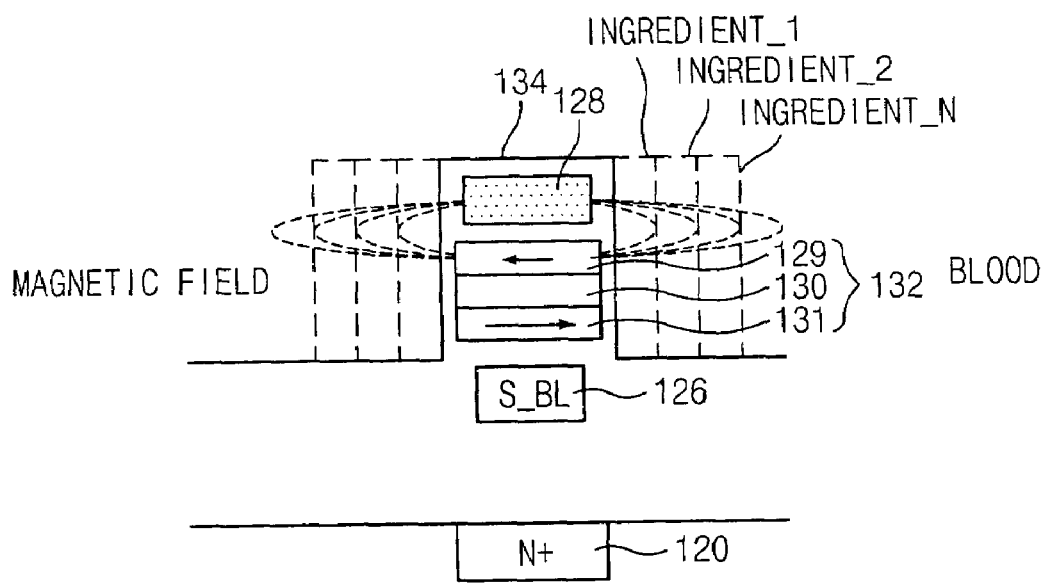

FIGS. 34a and 34b are diagrams illustrating ingredient separation depending on variation in a sense wordline voltage of the giant magnetoresistive sensor of FIG. 32.

When a sensing voltage is applied to a sense wordline 133, blood ingredients start to be slowly separated from a low sense wordline 133 voltage by their polarization characteristics as shown in FIG. 34a. As shown in FIG. 34b, the blood ingredients are separated with larger spectrum in a higher sense wordline 133 voltage.

In a magnetic field formed by magnetic coupling the free ferromagnetic layer 129 with the magnetic material 128, different magnetoresistive values are sensed since the magnetic flux density of adjacent magnetic materials is differentiated. The blood ingredient analysis means measures different sensing resistance values in the giant magnetoresistive sensor to analyze the blood ingredients quantitatively.

Figure 35A:
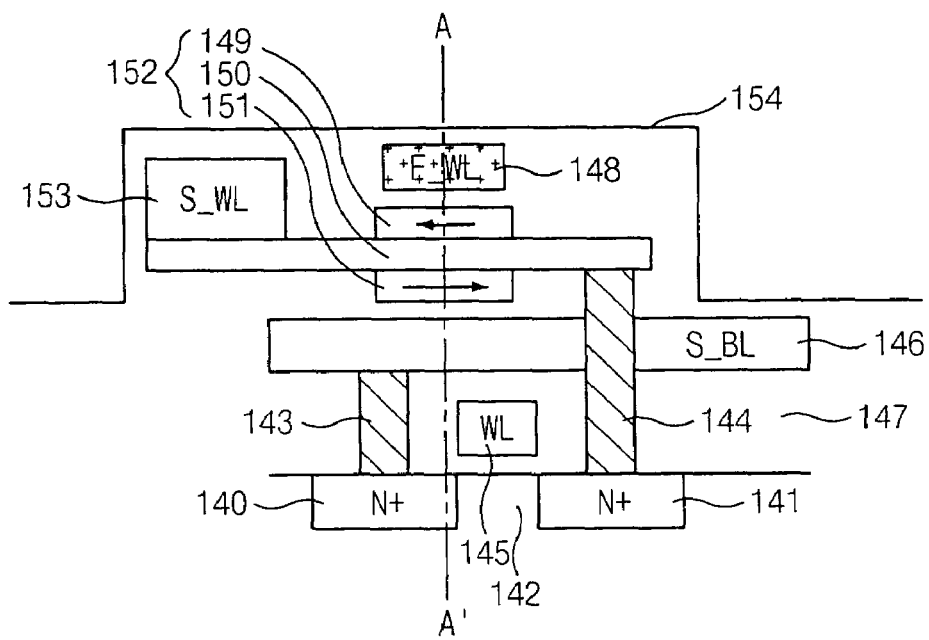
FIGS. 35a and 35b are diagrams illustrating a giant magnetoresistive sensor using a forcing wordline according to an embodiment of the present invention.
Figure 35B:
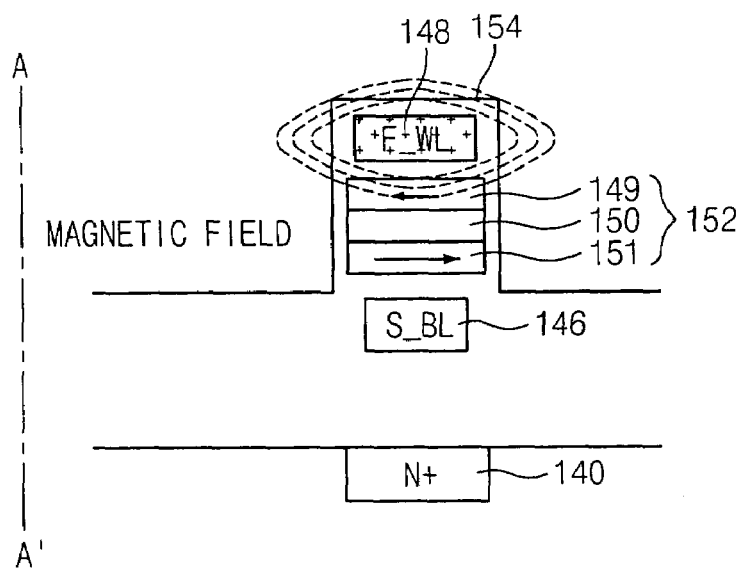

FIGS. 35a and 35b are diagrams illustrating a giant magnetoresistive sensor using a forcing wordline according to an embodiment of the present invention.

In an embodiment, the giant magnetoresistive sensor comprises a switching device, a GMR device 152, a sense wordline 153 and a forcing wordline 148.

The GMR device 152 comprises a free ferromagnetic layer 149, a conductive resistor 150 and a fixed ferromagnetic layer 151.

The switching device comprises a NMOS transistor. The NMOS transistor has a drain 140 connected to a sense bitline 146 through a contact line 143, a gate 142 connected to a wordline 145, and a source 141 connected to one portion of a conductive resistor 150 through a contact line 144. A sense wordline 153 is formed on the other portion of the conductive resistor 150.

The whole device is insulated by an oxide protective layer 154. A barrier conductive layer 147 is formed under a sense bitline 146.

FIG. 35b is a cross-sectional diagram illustrating the giant magnetoresistive sensor using the forcing wordline.

Referring to FIG. 35b, a magnetic field is formed around the forcing wordline 148 by magnetic coupling the free ferromagnetic layer 149 with the forcing wordline 148 of the GMR device 152. The whole device is insulated by an oxide protective layer 154. As a result, the size of magnetic field induced around the forcing wordline 148 by the magnitude of the current applied to the forcing wordline 148 is changed.

In the giant magnetoresistive sensor, a magnetic field is induced around the forcing wordline 148 by magnetic coupling the free ferromagnetic layer 149 with the forcing wordline 148 consisting of current source. As a result, different magnetoresistive values depending on ingredients of magnetic materials formed on the magnetic field are measured.

Figure 36A:
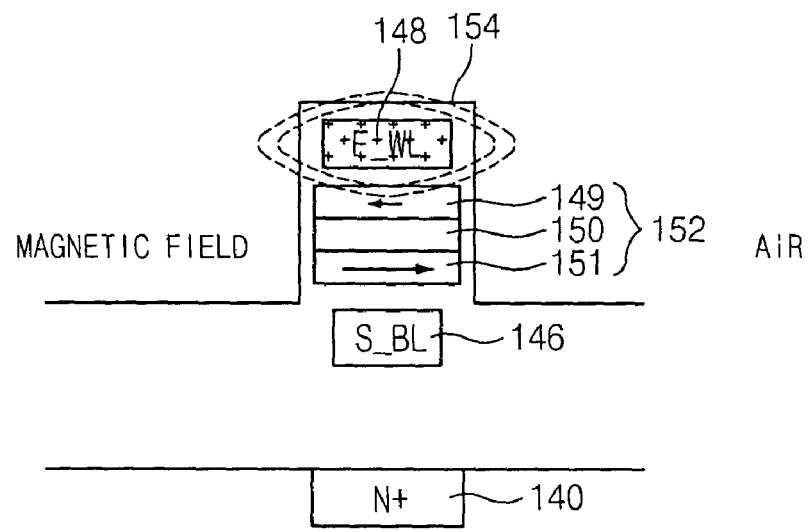
FIGS. 36a and 36b are diagrams illustrating operation characteristics of the giant magnetoresistive sensor of FIG. 35.
Figure 36B:
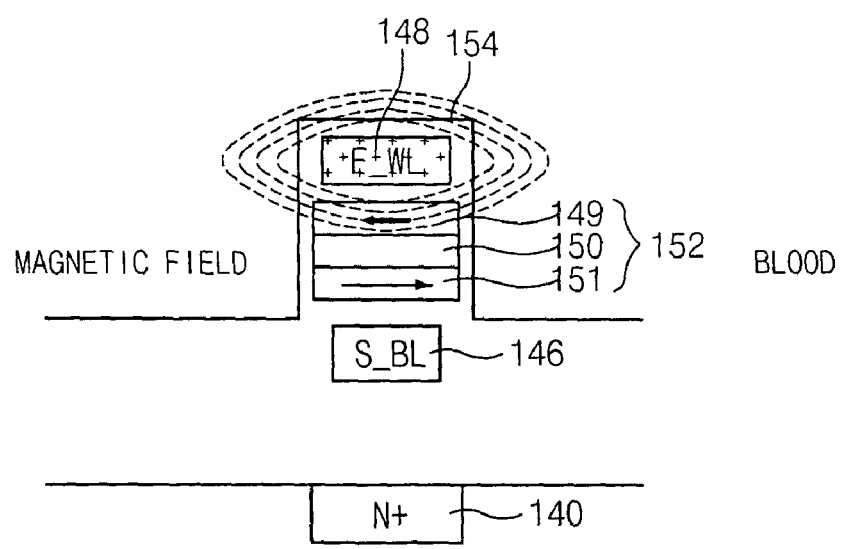

FIGS. 36a and 36b are diagrams illustrating operation characteristics of the giant magnetoresistive sensor of FIG. 35.

As shown in FIG. 36a, when the adjacent magnetic material of the giant magnetoresistive sensor is air, the free ferromagnetic layer 149 has a small magnetic density due to air having a small magnetic susceptibility. As a result, magnetoresistance is shown to be small. However, as shown in FIG. 36b, when the adjacent magnetic material of the magnetization pair detection sensor is bio material (blood), the free ferromagnetic layer 149 has a large magnetic density due to blood having a large magnetic susceptibility. As a result, magnetoresistance is shown to be large.

Figure 37A:
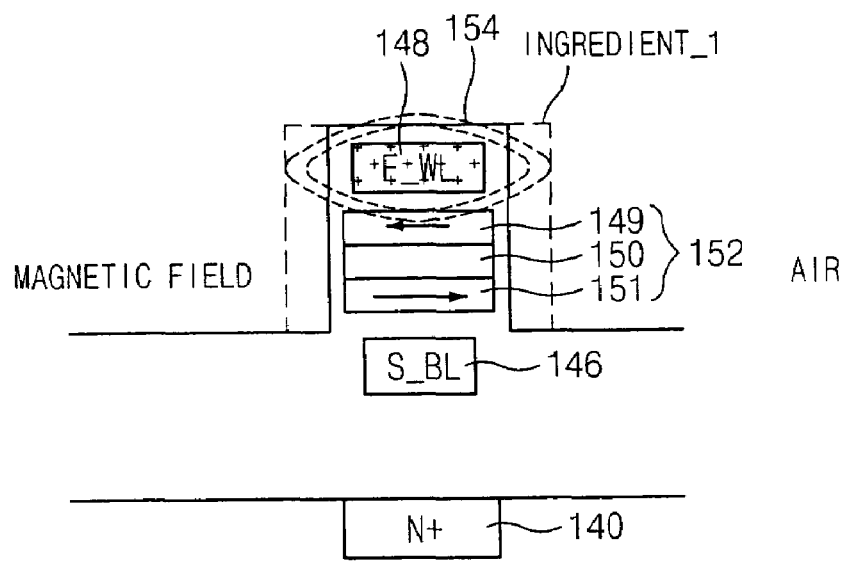
FIGS. 37a and 37b are diagrams illustrating ingredient separation depending on variations in a forcing wordline voltage of the giant magnetoresistive sensor of FIG. 35.
Figure 37B:
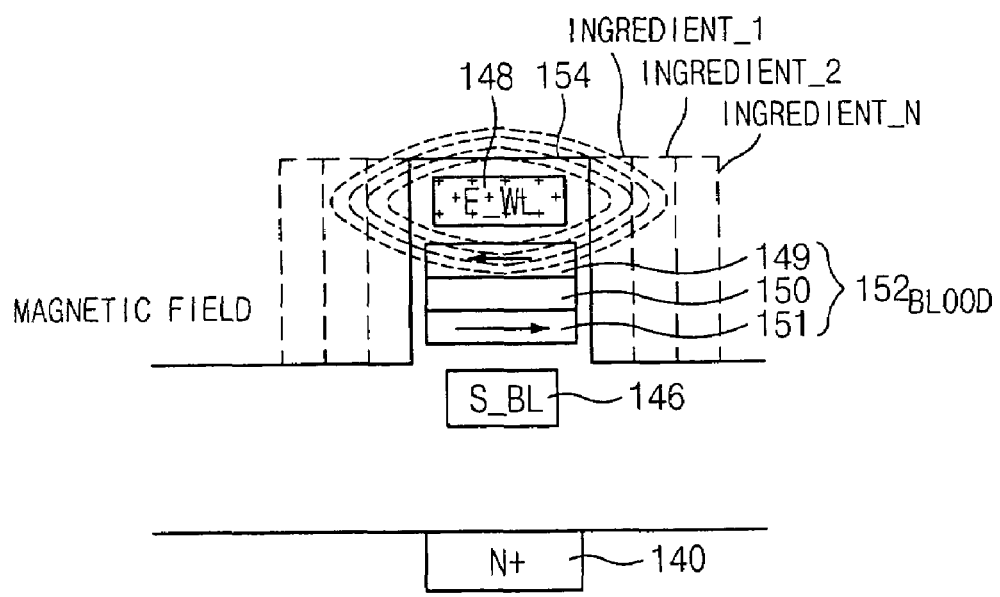

FIGS. 37a and 37b are diagrams illustrating ingredient separation depending on variations in a forcing wordline F_WL voltage of the giant magnetoresistive sensor of FIG. 35 using a forcing wordline F_WL.

When a sensing voltage is applied to a forcing wordline 148, blood ingredients start to be slowly separated from a low forcing wordline 148 voltage by their polarization characteristics as shown in FIG. 37a. As shown in FIG. 37b, the blood ingredients are separated with larger spectrum in a higher forcing wordline 148 voltage.

As a result, in a magnetic field formed by magnetic coupling the free ferromagnetic layer 149 with the forcing wordline 148, different values of magnetoresistance are sensed depending on the magnetization density of adjacent magnetic materials differentiated by voltage values of the forcing wordline 148. The blood ingredient analysis means measures different sensing resistance values in the giant magnetoresistive sensor to analyze the blood ingredients quantitatively.

Figure 38:
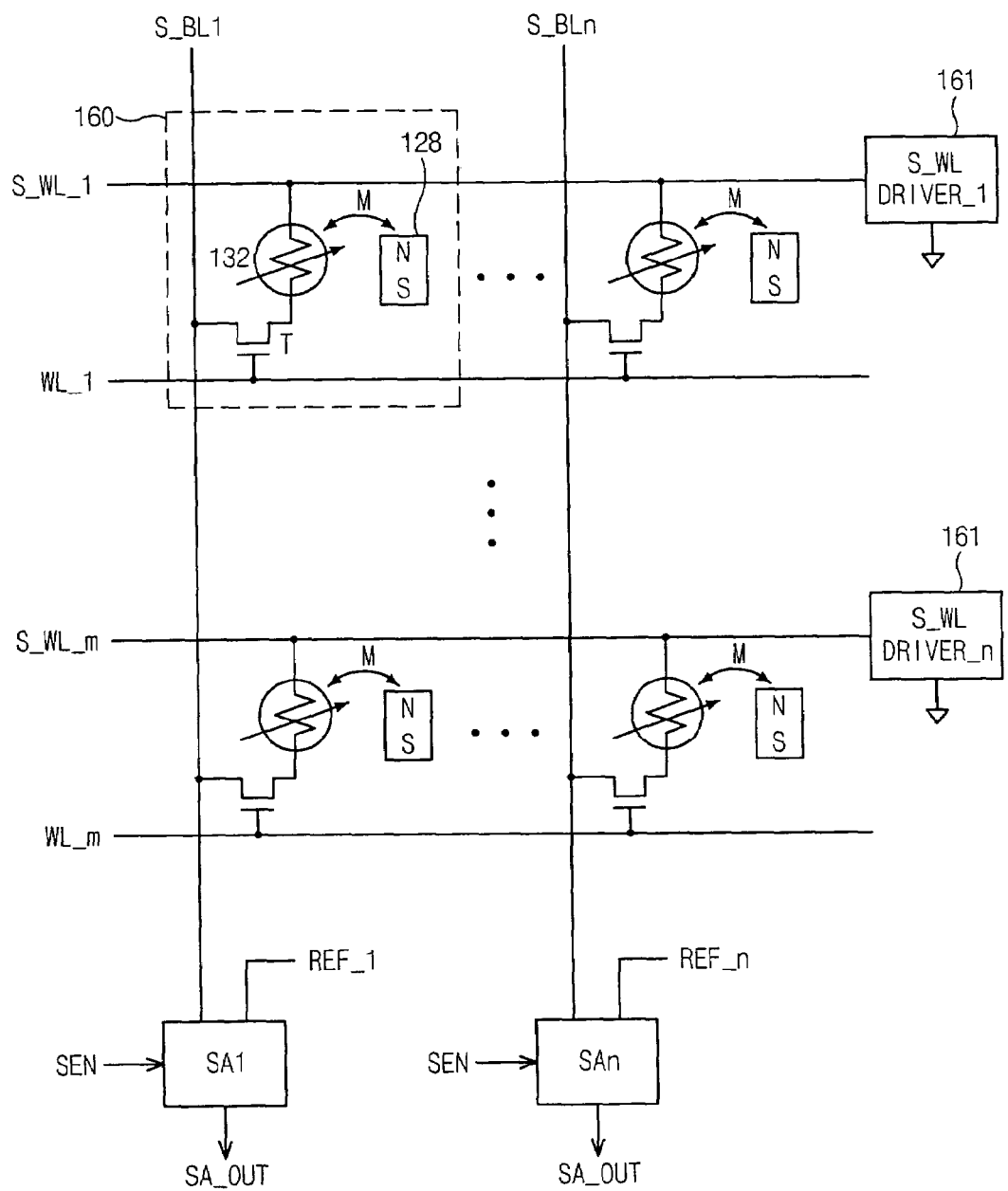
FIGS. 38 and 39 are diagrams illustrating a sensing cell array using a giant magnetoresistive sensor according to an embodiment of the present invention.
Figure 39:
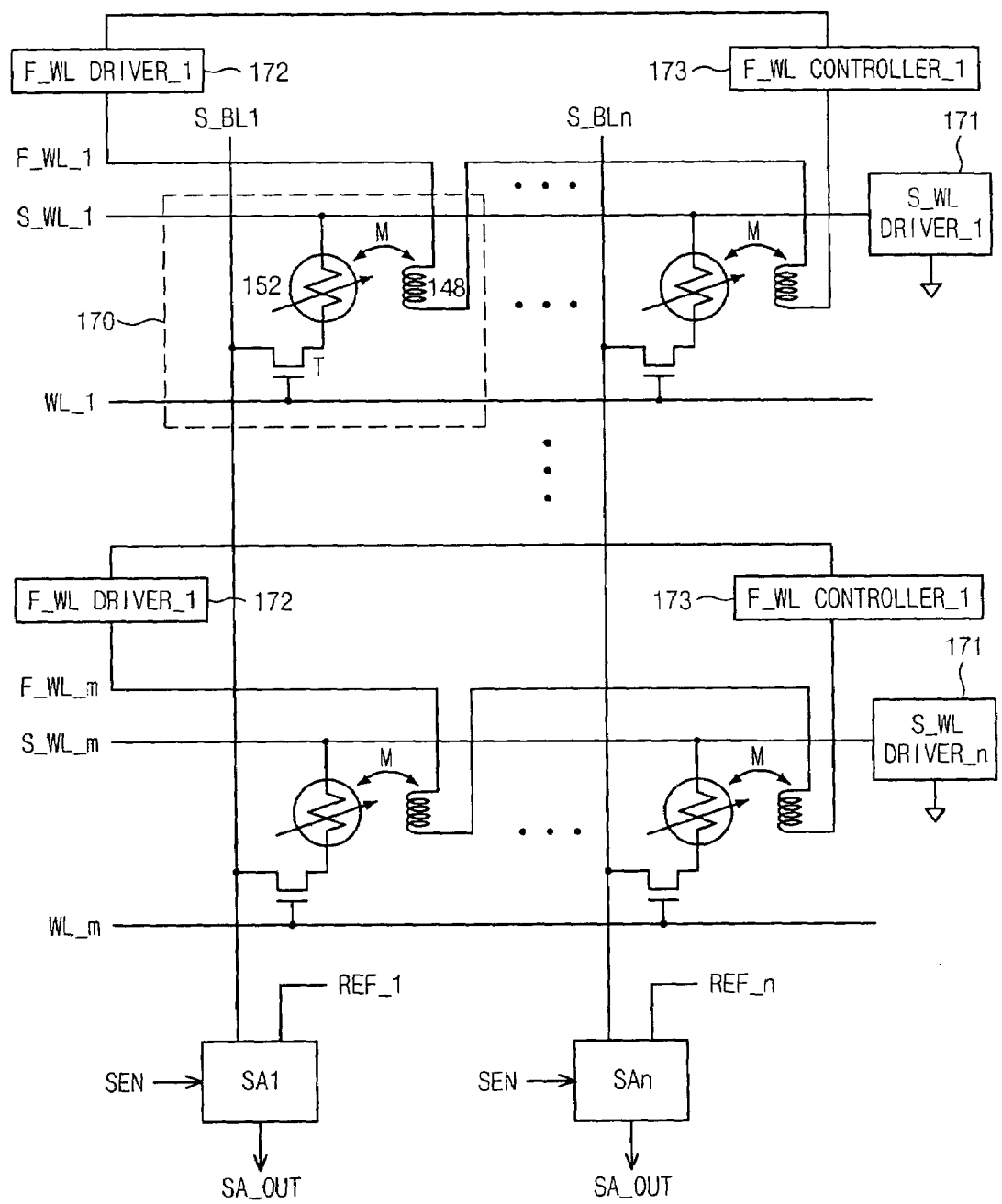

FIGS. 38 and 39 are diagrams illustrating a sensing cell array using a giant magnetoresistive sensor according to an embodiment of the present invention.

In the sensing cell array using the giant magnetoresistive sensor, a plurality of wordlines WL_1~WL_m are arranged parallel to a plurality of sense wordlines S_WL_1~S_WL_m in a row direction. In a column direction, a plurality of sense bitlines S_BL1~S_BLn are arranged perpendicular to the plurality of wordlines WL_1~WL_m and the plurality of sense wordlines S_WL_1~S_WL_m.

The plurality of sense wordlines S_WL_1~S_WL_m comprise a plurality of sense wordline S_WL drivers 161 one by one. The plurality of sense wordlines S_WL drivers 161 apply different bias voltages to the plurality of sense wordlines S_WL, correspondingly.

A plurality of giant magnetoresistive sensors 160 are positioned between the plurality of wordlines WL_1~WL_m, the plurality of sense wordlines S_WL_1~S_WL_m and the plurality of sense bitlines S_BL1~S_BLn.

A magnetoresistive sensor 160 comprises a switching device T, a GMR device 132 and a magnetic material 128.

The switching device T has a drain connected to the sense bitline S_BL, a source connected to a terminal of the GMR device 132, and a gate connected to a wordline WL. The other terminal of the GMR device 132 is connected to a sense wordline S_WL. The GMR device 132 forms a magnetic field M by magnetic coupling with the magnetic material 128.

The plurality of sense bitlines S_BL1~S_BLn are connected one by one to the plurality of sense amplifiers SA1~SAn. When a sense amplifier enable signal SEN is applied, the plurality of sense amplifiers SA1~SAn compare and amplify output signals from the sense bitlines S_BL1~S_BLn with reference voltages REF to output sense amplifier output signals SA_OUT.

Each reference voltage REF is set to have different values so that the sense amplifiers may have different characteristics. In the sensing cell array using the magnetoresistive sensor, characteristics of blood ingredients are variously analyzed by the reference voltages REF having different levels.

In the sensing cell array, when different bias voltages are applied to the GMR device 132 through the sense wordline S_WL, a magnetic field is induced by magnetic coupling with the magnetic material 128. The GMR device 132 senses different values of magnetoresistance depending on magnetic susceptibility of adjacent materials to output different currents. If a gate of the switching device T receives a wordline WL voltage, the switching device T is turned on to output the different currents sensed in the GMR device 132 into the sense bitline S_BL.

The sense amplifiers SA compare and amplify the reference voltages REF with output signals applied from the sense bitlines S_BL in response to the sense amplifier enable signals SEN to output the sense amplifier output signals SA_OUT. As a result, each row and each column of the sensing cell array using the magnetoresistive sensor obtain characteristics of different ingredients.

FIG. 39 is a diagram illustrating a sensing cell array of a giant magnetoresistive sensor using a forcing wordline according to an embodiment of the present invention.

In the sensing cell array using the magnetoresistive sensor, a plurality of wordlines WL_1~WL_m are arranged parallel to a plurality of sense wordlines S_WL_1~S_WL_m and a plurality of forcing wordlines F_WL_1~F_WL_m in a row direction. In a column direction, a plurality of sense bitlines S_BL1~S_BLn are arranged perpendicular to the plurality of wordlines WL_1~WL_m, the plurality of sense wordlines S_WL_1~S_WL_m and the plurality of forcing wordlines F_WL_1~F_WL_m.

The plurality of sense wordlines S_WL_1~S_WL_m comprises a plurality of sense wordline S_WL drivers 171. The plurality of sense wordline S_WL drivers 171 apply different bias voltages to the plurality of sense wordlines S_WL.

A plurality of giant magnetoresistive sensors 170 are positionedbetween the plurality of wordlines WL_1~WL_m, the plurality of sense wordlines S_WL_1~S_WL_m, the plurality of forcing wordlines F_WL_1~F_WL_m and the plurality of sense bitlines S_BL1~S_BLn.

A giant magnetoresistive sensor 170 comprises a switching device T, a GMR device 152 and a forcing wordline 148.

The switching device T has a drain connected to the sense bitline S_BL, a source connected to a terminal of the GMR device 152, and a gate connected to a wordline WL. The other terminal of the GMR device 152 is connected to the sense wordline S_WL. The GMR device 152 forms a magnetic field M by magnetic coupling with the forcing wordline 148.

The forcing wordline 148 is connected to a forcing wordline F_WL controller 173 configured to control current of the forcing wordline F_WL driver 172 and the forcing wordline 148 for supplying forcing wordline voltages to induce a magnetic field.

In order to form a magnetic field around the forcing wordline 148, the amount of current in the sense bitline S_BL is changed, and the amount of current in the forcing wordline F_WL is fixed. Also, the amount of current in the sense bitline S_BL is fixed, and the amount of current in the forcing wordline F_WL is changed.

The plurality of sense bitline S_BL1~S_BLn are connected one by one to the plurality of sense amplifiers SA1~SAn. When a sense amplifier enable signal SEN is applied, the plurality of sense amplifiers SA1~SAn compare and amplify reference voltages REF with output signals from the sense bitline S_BL1~S_BLn to output sense amplifier output signals SA_OUT. Each reference voltage REF is set to have different values so that the sense amplifiers SA may have different characteristics.

That is, in the sensing cell array using the giant magnetoresistive sensor, characteristics of blood ingredients are variously analyzed by the reference voltages REF having different levels.

In an embodiment, a magnetic field is induced by magnetic coupling if different bias voltages are applied to the GMR device 152 through the sense wordline S_WL and forcing wordline voltages are applied through the forcing wordline 148. The GMR device 152 senses different values of magnetoresistance depending on magnetic susceptibility of adjacent materials to output different current. If a gate of the switching device T receives a wordline WL voltage, the switching device T is turned on to output different current sensed in the GMR device 152 into the sense bitlines S_BL.

The sense amplifiers SA compare and amplify reference voltages REF with output signals applied from the sense bitlines S_BL in response to the sense amplifier enable signals SEN. As a result, each row and each column of the sensing cell array using the giant magnetoresistive sensor obtain characteristics of different ingredients.

Figure 40:
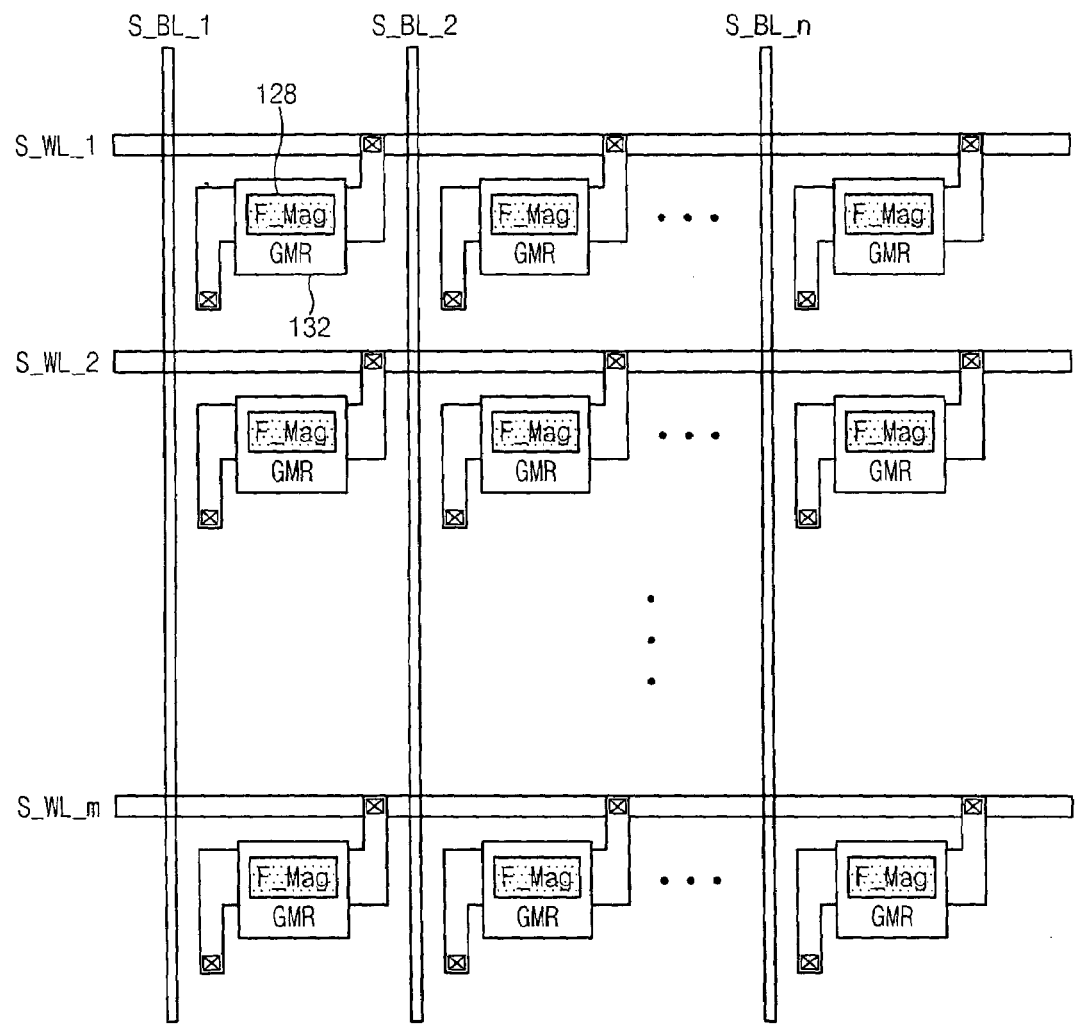
FIGS. 40 and 41 are layout diagrams illustrating a sensing cell array using a giant magnetoresistive sensor according to an embodiment of the present invention.

FIG. 40 is a layout diagram illustrating a sensing cell array of a giant magnetoresistive sensor using a magnetic material according to an embodiment of the present invention.

A plurality of sense bitlines S_BL intersect a plurality of sense wordlines S_WL. The magnetic material 128 is formed on the GMR device 132.

Figure 41:
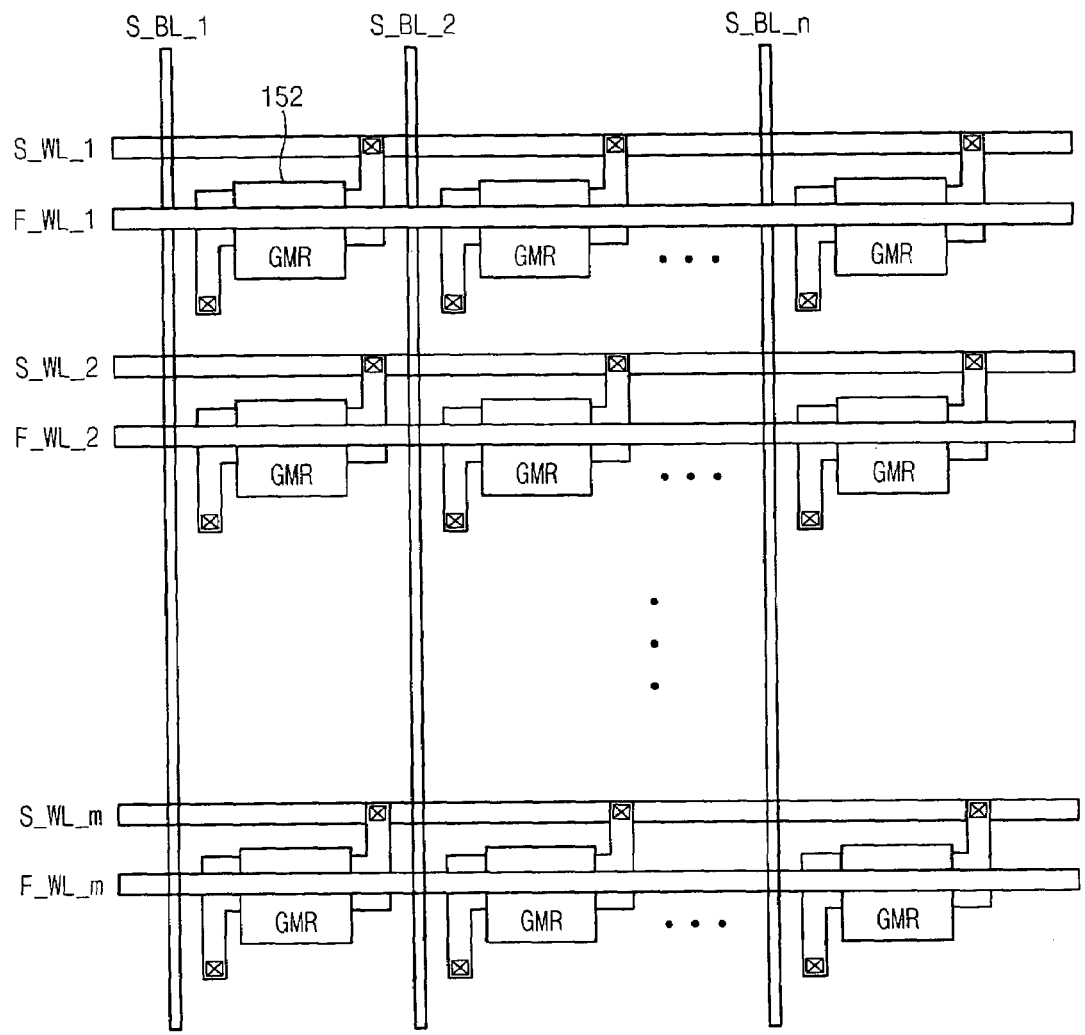

FIG. 41 is a layout diagram illustrating a sensing cell array using a forcing wordline according to an embodiment of the present invention.

The plurality of sense bitlines S_BL intersect the plurality of sense wordlines S_WL and the plurality of forcing wordlines F_WL. On the plurality of GMR devices 152, the plurality of forcing wordlines F_WL are arranged parallel to the plurality of sense wordlines S_WL.

Figure 42:
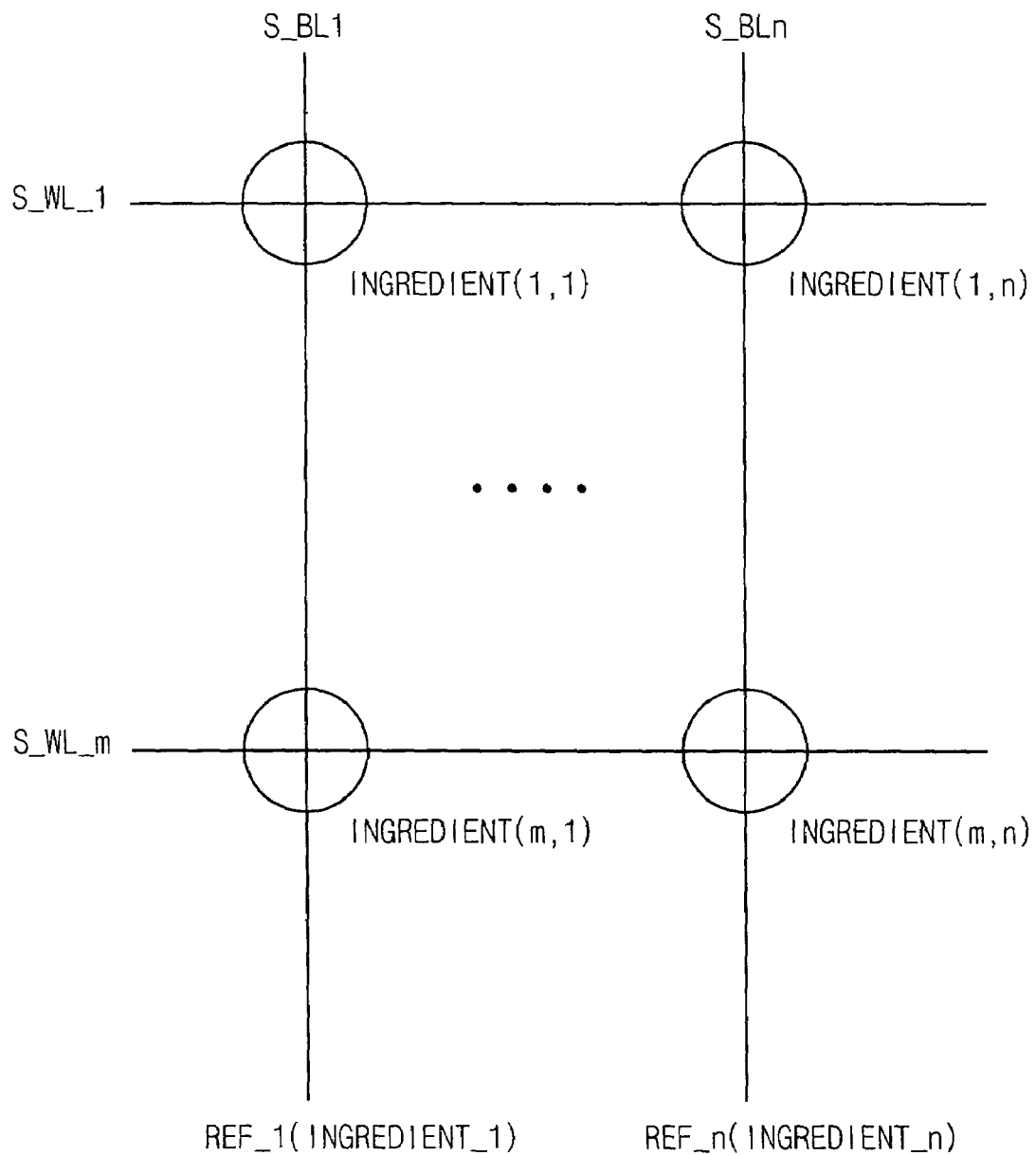
FIGS. 42 and 43 are ingredient analysis diagrams illustrating a sensing cell array using a giant magnetoresistive sensor according to an embodiment of the present invention.

FIG. 42 is an ingredient analysis diagram illustrating a sensing cell array of a giant magnetoresistive sensor using magnetic materials according to an embodiment of the present invention.

Ingredients of adjacent materials are separated by bias voltages of the plurality of sense wordlines S_WL_1~S_WL_m. Ingredients of adjacent materials in the plurality of sense bitlines S_BL1S_BLn are separated by the plurality of different reference voltages REF_1~REF_n. As a result, different characteristics of adjacent materials may be analyzed in the sensing cell array of the whole giant magnetoresistive sensor.

Figure 43:
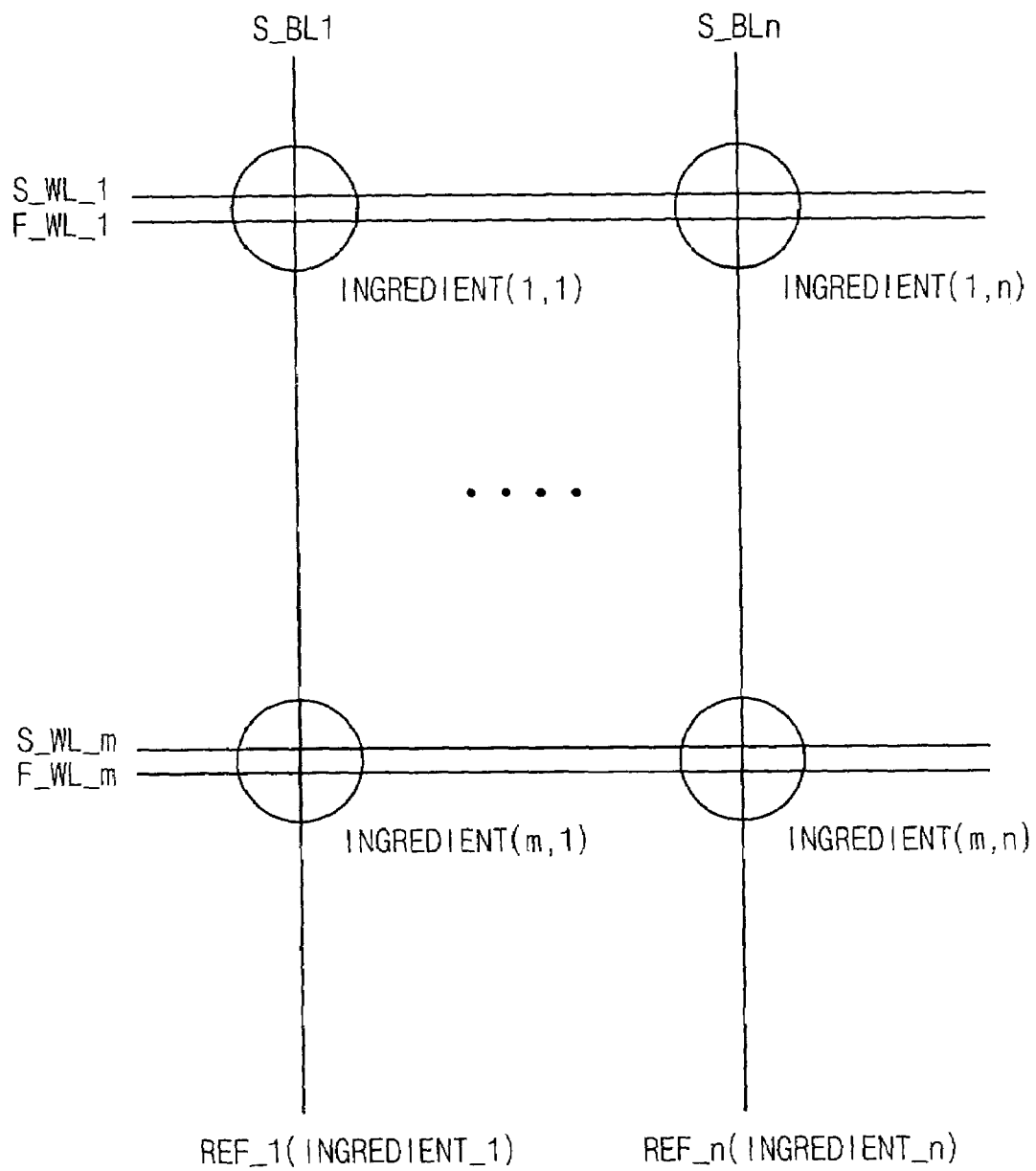

FIG. 43 is an ingredient analysis diagram illustrating a sensing cell array of a giant magnetoresistive sensor using a forcing wordline according to an embodiment of the present invention.

Ingredients of adjacent materials are separated by bias voltages of the plurality of sense wordlines S_WL_1~S_WL_m. Ingredients of adjacent materials in the plurality of forcing wordlines F_WL_1~F_WL_m are separated by forcing wordline F_WL voltages regulated by the F_WL driver 172. Ingredients of adjacent materials in the plurality of sense bitlines S_BL1~S_BLn are separated by the plurality of different reference voltages REF_1~REF_n. As a result, different characteristics of adjacent materials may be analyzed in the sensing cell array of the whole giant magnetoresistive sensor.

Figure 44:
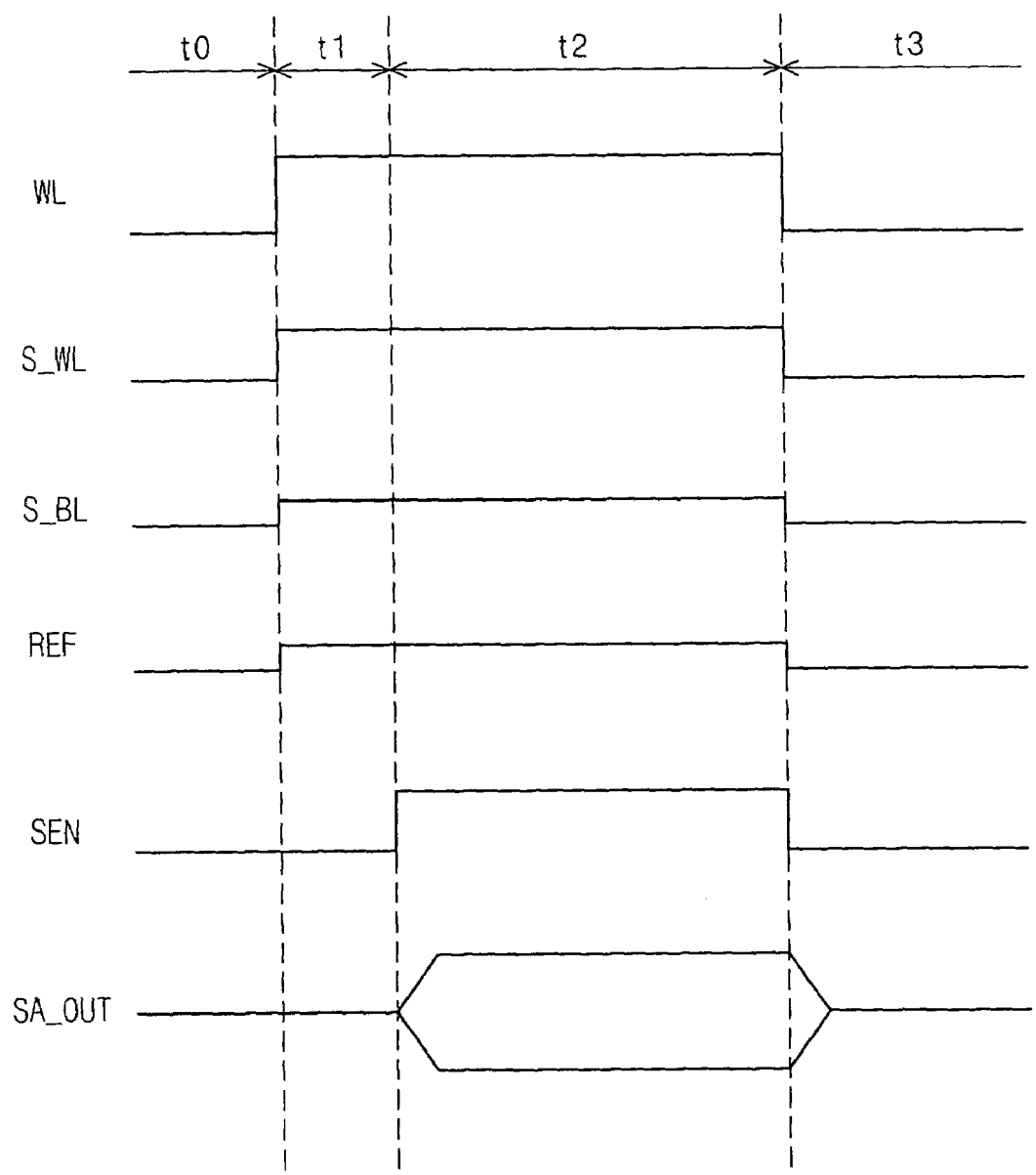
FIGS. 44 and 45 are timing diagrams illustrating a sensing cell array using a giant magnetoresistive sensor according to an embodiment of the present invention.

FIG. 44 is a timing diagram illustrating a read operation of a sensing cell array using a giant magnetoresistive sensor according to an embodiment of the present invention.

When an interval t1 starts, the wordline WL, the sense wordline S_WL, the sense bitline S_BL and the reference voltage REF are activated. The different values of magnetoresistance sensed in the GMR sensor 132 are outputted into each sense amplifier SA through the sense bitlines S_BL.

In an interval t2, if the sense amplifier enable signal SEN is activated, different values of magnetoresistance sensed in the sense amplifiers SA are amplified, and sense amplifier output signals SA_OUT are outputted. As a result, the blood ingredient analysis means analyzes the sense amplifier output signals SA_OUT from the sensing cell array to analyze ingredients of adjacent materials.

In an interval t3, the wordline WL, the sense wordline S_WL, the sense bitline S_BL and the reference voltage REF are inactivated. The sense amplifier enable signal SEN is disabled, and the operation stops.

Figure 45:
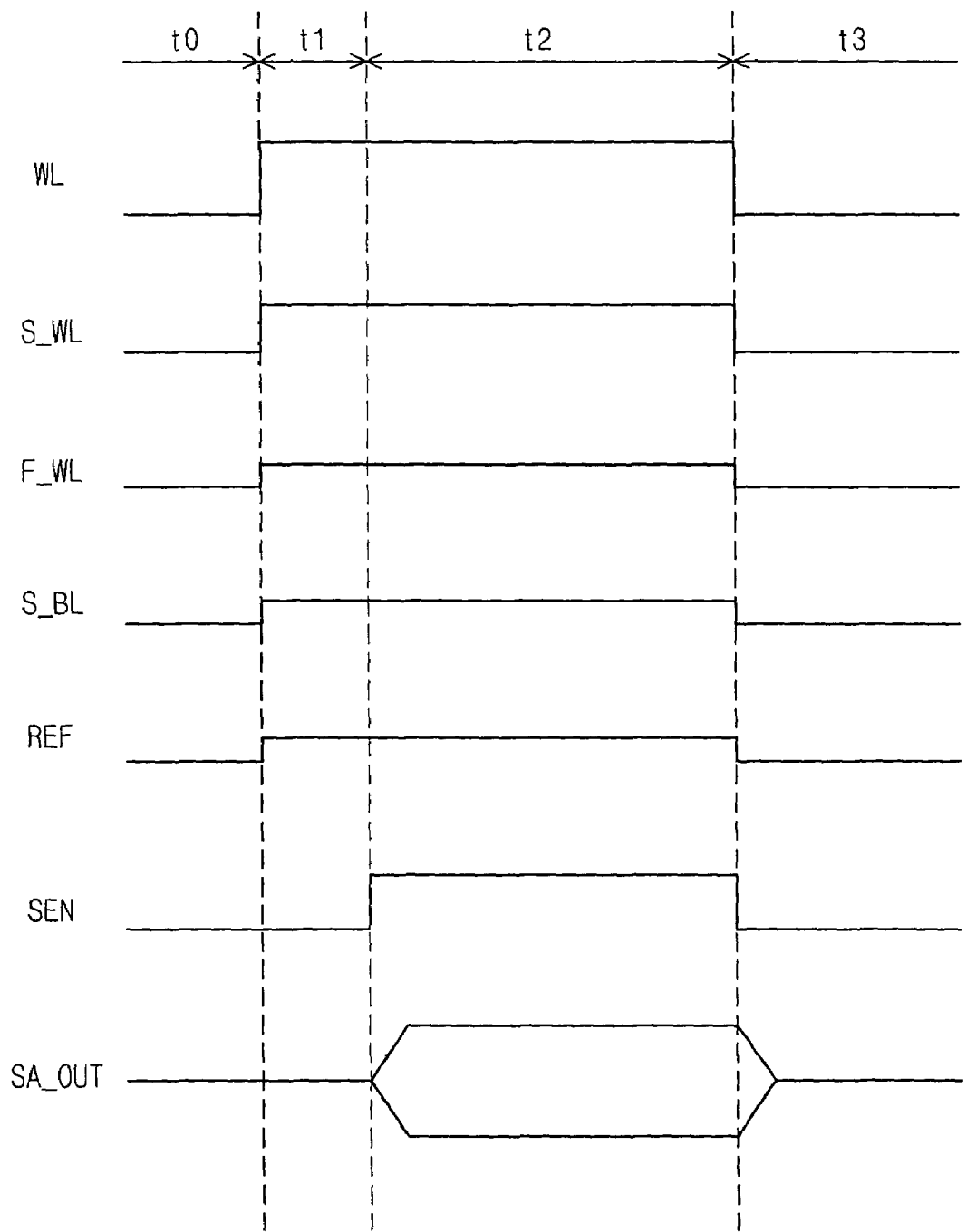

FIG. 45 is a timing diagram illustrating a read operation of a sensing cell array of a giant magnetoresistive sensor using a forcing wordline.

In an interval t1, the wordline WL, the forcing wordline F_WL, the sense wordline S_WL, the sense bitline S_BL and the reference voltage REF are activated. The different values of magnetoresistance sensed in the GMR sensor 152 are outputted into the sense amplifiers SA through the sense bitlines S_BL.

In an interval t2, if the sense amplifier enable signal SEN is activated, different values of magnetoresistance sensed in the sense amplifiers SA are amplified, and sense amplifier output signals SA_OUT are outputted. As a result, the blood ingredient analysis means analyzes the sense amplifier output signals SA_OUT from the sensing cell array to analyze ingredients of adjacent materials.

In an interval t3, the wordline WL, the forcing wordline F_WL, the sense wordline S_WL, the sense bitline S_BL and the reference voltage REF are inactivated. The sense amplifier enable signal SEN is disabled, and the operation stops.

Hereinafter, a giant magnetoresistive sensor and a sensing cell array using the same according to a fourth embodiment of the present invention are described referring to FIGS. 46a to 55.

Figure 46A:
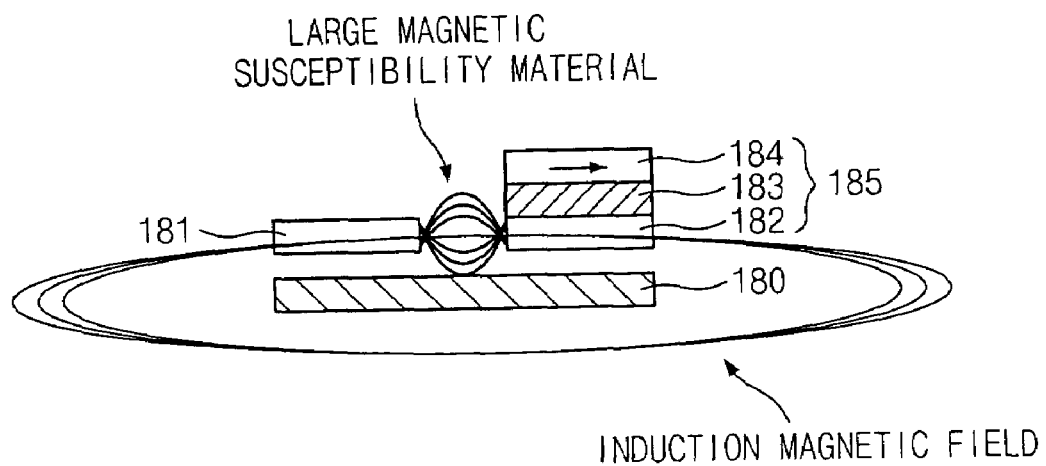
FIGS. 46a and 46b are structural diagrams illustrating a magnetization hole detection sensor.
Figure 46B:
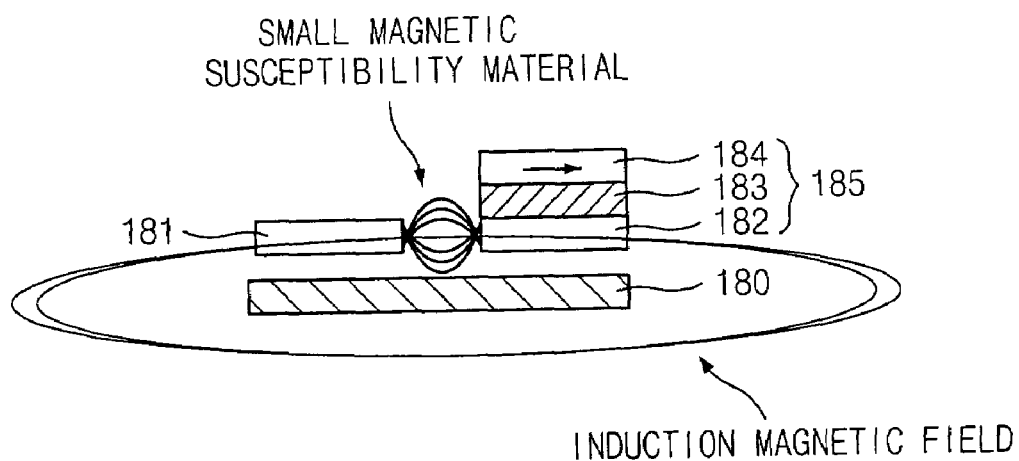

FIGS. 46a and 46b are structural diagrams illustrating a magnetization hole detection sensor according to an embodiment of the present invention.

In an embodiment, the magnetization hole detection sensor comprises a current line 180, a free ferromagnetic layer 181, and a MTJ (GMR) device 185. The current line 180 receives current to form an induction magnetic field. The free ferromagnetic layer 181 is formed on a portion of the current line 180. The MTJ (or GMR) device 185 is formed on the other portion of the current line 180.

Here, the MTJ device 185 comprises a free ferromagnetic layer 182, a tunnel junction layer 183 and a fixed ferromagnetic layer 184. When a predetermined current is applied to the current line 180, an induction magnetic field is formed around the current line 180 through the free ferromagnetic layers 181 and 182 and adjacent materials therebetween.

As shown in FIG. 46a, when there are materials having high magnetic susceptibility between the two free ferromagnetic layers 181 and 182, the free ferromagnetic layers 181 and 182 have a high magnetic flux density. As a result, the size of induction magnetic field is shown to be large. On the other hand, as shown in FIG. 46b, when there are materials having low magnetic susceptibility between the two free ferromagnetic layers 181 and 182, the free ferromagnetic layers 181 and 182 have a low magnetic flux density. As a result, the size of the induction magnetic field is shown to be small.

Accordingly, in a magnetic line of the free ferromagnetic layer 182 of the MTJ (or GMR) device 185, variation values of magnetoresistance are obtained by using magnetic susceptibility of intermediate adjacent materials differentiated depending on ingredients of adjacent materials.

Figure 47A:
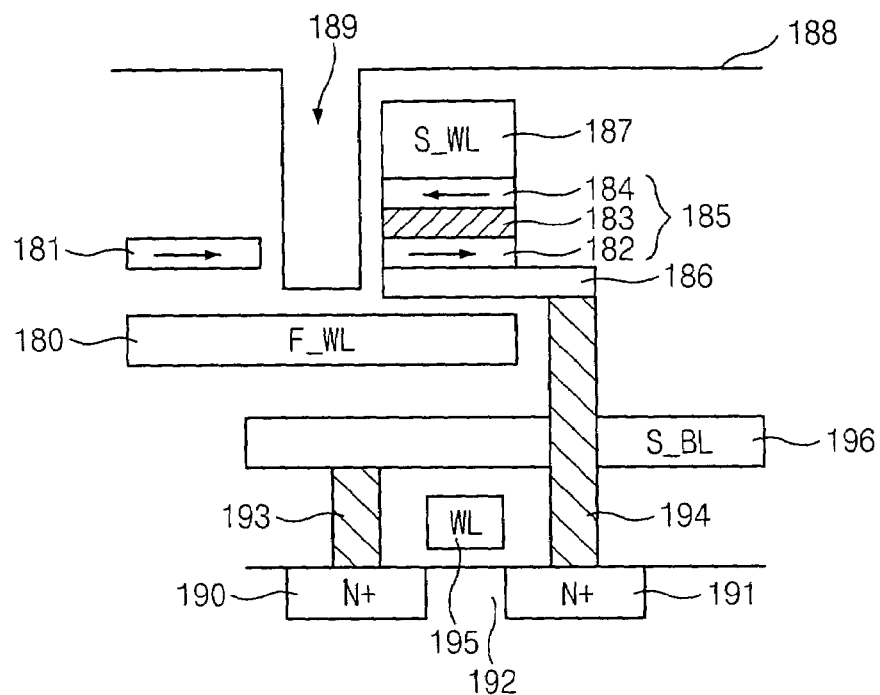
FIGS. 47a and 47b are cross-sectional and planar view diagrams illustrating a magnetization hole detection sensor according to an embodiment of the present invention.
Figure 47B:
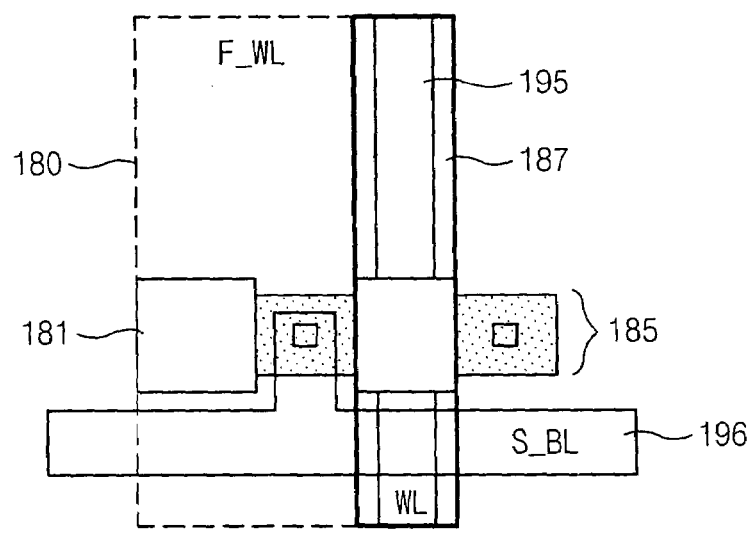

FIGS. 47a and 47b are cross-sectional and planar view diagrams illustrating a magnetization hole detection sensor using a MTJ device according to an embodiment of the present invention.

In an embodiment, the magnetization hole detection sensor comprises a switching device, a current line 180, a free ferromagnetic layer 181 and a MTJ device 185. The current line 180 receives a forcing wordline current to induce a magnetic field to a free ferromagnetic layer 182 of the MTJ device 185. Here, the MTJ device 185 comprises a free ferromagnetic layer 182, a tunnel junction layer 183 and a fixed ferromagnetic layer 184. A barrier conductive layer 186 is formed under the free ferromagnetic layer 182.

A sense wordline 187 is formed on the fixed ferromagnetic layer 184 of the MTJ device 185. The whole device is isolated by an oxide protective layer 189. A sensing hole 189 having a predetermined size is formed between the free ferromagnetic layer 181 and the MTJ device 185. Ingredients of adjacent materials are exposed in the sensing hole 189.

The switching device T comprises a NMOS transistor. The NMOS transistor has a drain 190 connected to a sense bitline 196 through a contact line 193, a gate 192 connected to a wordline 195, and a source 191 connected to the barrier conductive layer 186 formed under the MTJ device 185 through a contact hole 194.

Figure 48:
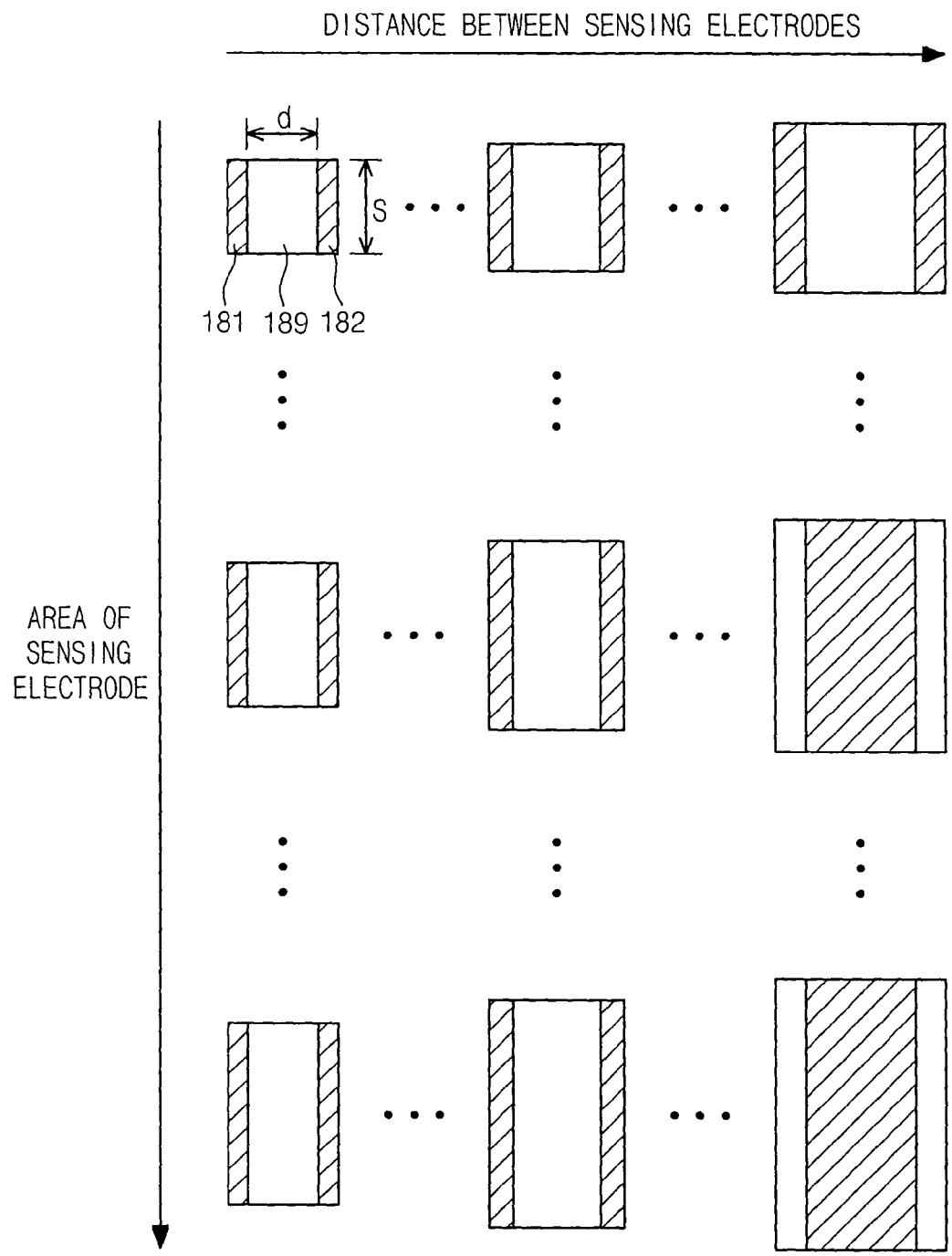
FIG. 48 is a diagram illustrating a sensing hole type of a magnetization hole detection sensor according to an embodiment of the present invention.

FIG. 48 is a diagram illustrating a sensing hole 189 type of a magnetization hole detection sensor according to an embodiment of the present invention.

In an embodiment, a horizontal direction is set as variables depending on the distance d between the free ferromagnetic layers 181 and 182, and a vertical direction is set as variables depending on the area S of the free ferromagnetic layers 181 and 182. As a result, the sizes of ingredients of adjacent materials may be separated depending on the distance d between the free ferromagnetic layers 181 and 182, and the amounts of ingredients corresponding to the sizes of adjacent materials may be analyzed quantitatively depending on the area S between the free ferromagnetic layers 181 and 182.

Figure 49A:
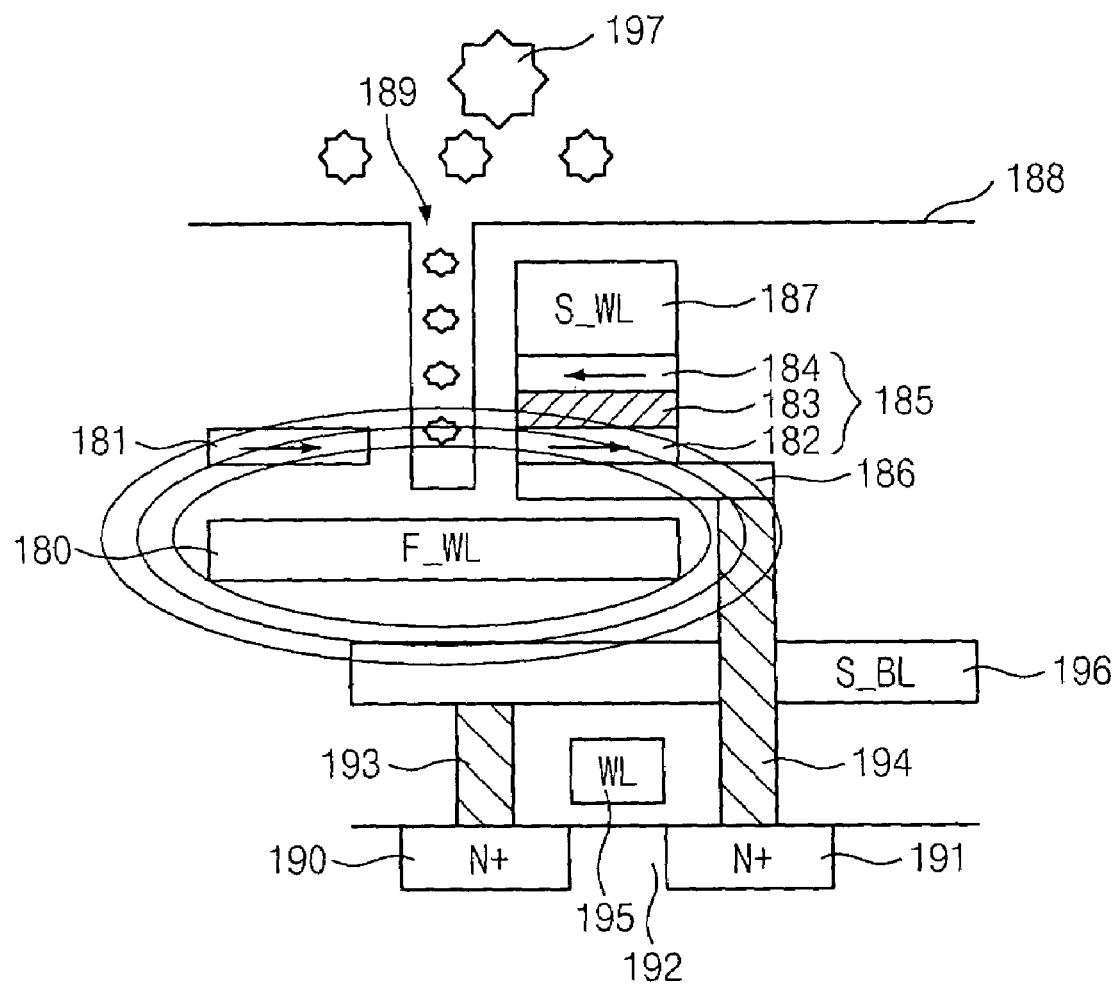
FIGS. 49a and 49b are diagrams illustrating the variation in magnetic susceptibility depending on sizes of sensing holes of a magnetization hole detection sensor using a MTJ device according to an embodiment of the present invention.
Figure 49B:
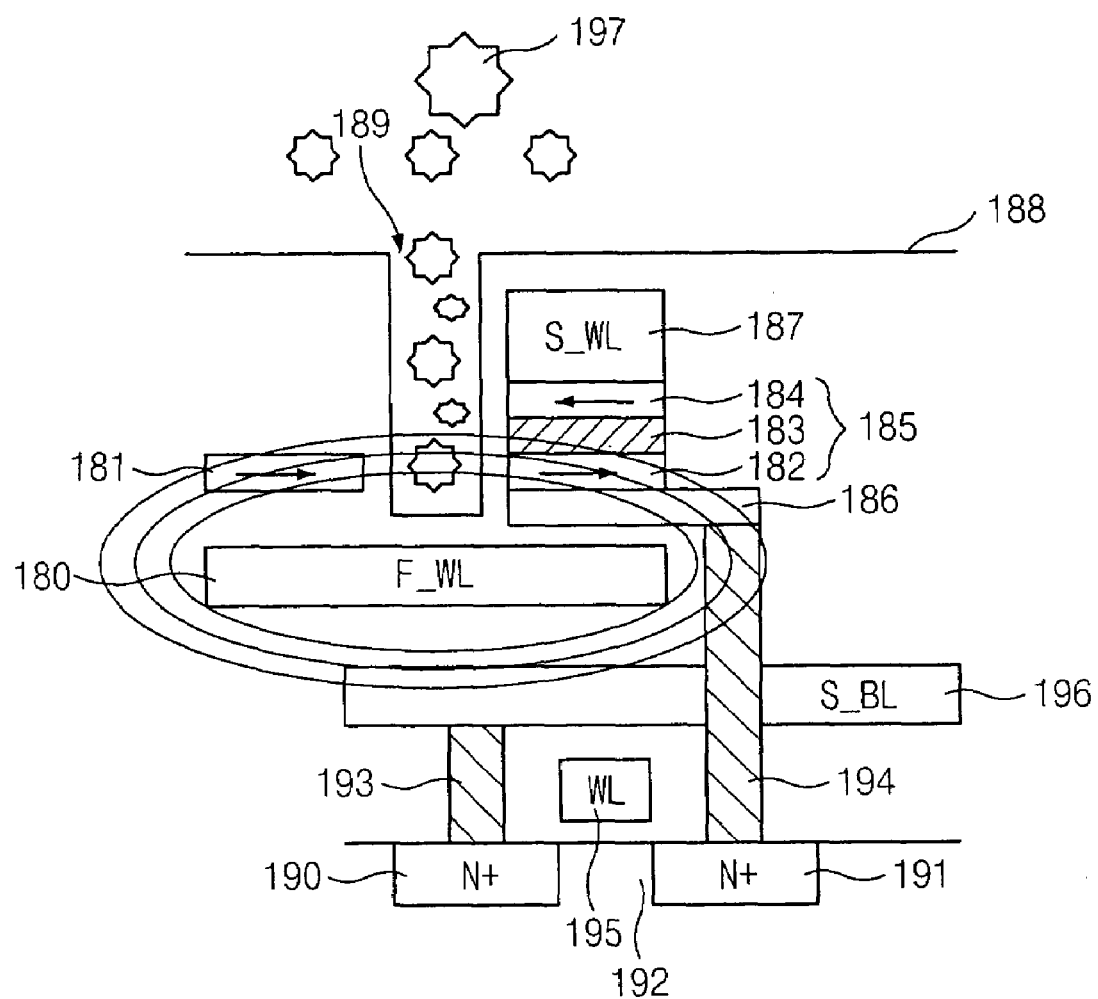

FIGS. 49a and 49b are diagrams illustrating the variation in magnetic susceptibility depending on sizes of sensing holes 189 of the magnetization hole detection sensor using the MTJ device 185 according to an embodiment of the present invention.

As shown in FIG. 49a, when the distance between the free ferromagnetic layers 181 and 182 is short, the size of the sensing hole 189 becomes smaller. Ingredients of adjacent materials having a size larger than the sensing hole 189 cannot penetrate into the sensing hole 189. As a result, ingredients of the adjacent materials 197 having the small size may be sensed by sensing the magnetization constant u of the adjacent materials 197 exposed in the sensing hole 189.

As shown in FIG. 49b, when the distance between the free ferromagnetic layers 181 and 182 is long, the size of the sensing hole 189 becomes larger. Ingredients of adjacent materials having a size smaller than the sensing hole 189 can penetrate into the sensing hole 189. As a result, ingredients of the adjacent materials 197 having the large size may be sensed by sensing the magnetization constant u of the adjacent materials 197 exposed in the sensing hole 189.

Figure 50A:
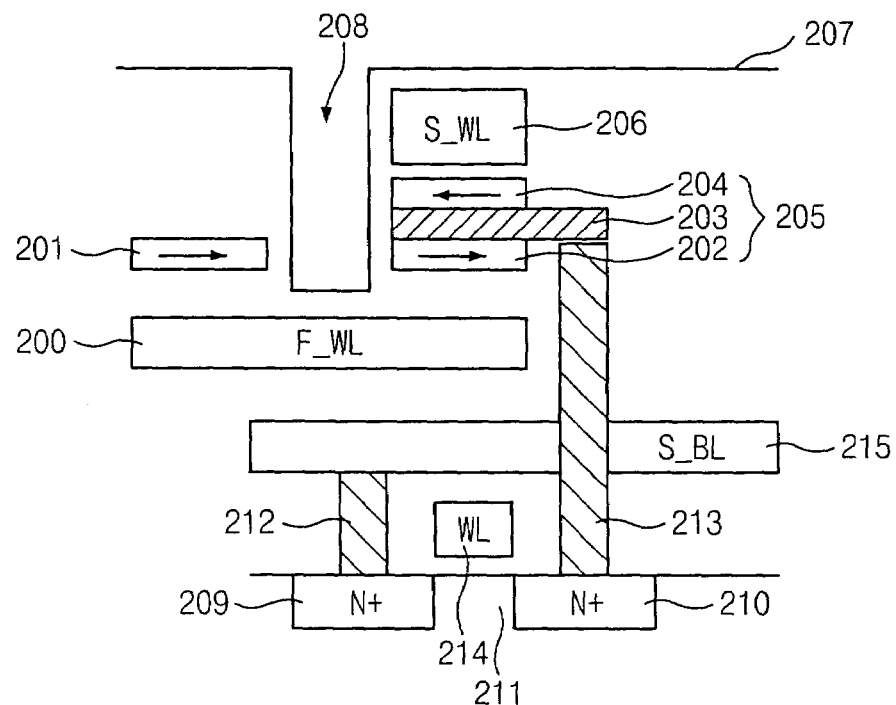
FIGS. 50a and 50b are structural diagrams illustrating a magnetization hole detection sensor using a GMR device according to an embodiment of the present invention.
Figure 50B:
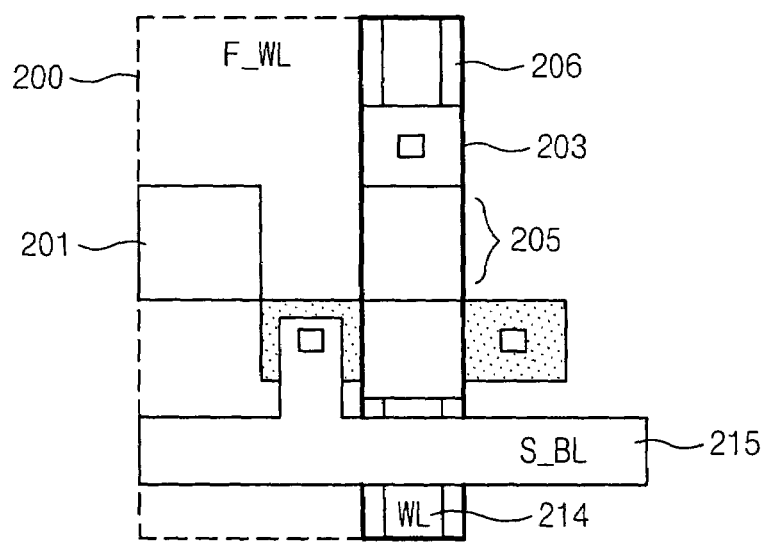

FIGS. 50a and 50b are structural diagrams illustrating a magnetization hole detection sensor using a GMR device according to an embodiment of the present invention.

In an embodiment, the magnetization hole detection sensor comprises a switching device, a current line 200, a free ferromagnetic layer 201 and a GMR device 205. The current line 200 receives forcing wordline current to induce a magnetic field to a free ferromagnetic layer 202. Here, the GMR device 205 comprises a free ferromagnetic layer 202, a sensing conductive layer 203 and a fixed ferromagnetic layer 204.

A sense wordline 206 is formed on the fixed ferromagnetic layer 204 of the GMR device 205. The whole device is insulated by an oxide protective layer 207. A sensing hole 208 having a predetermined size is formed between the free ferromagnetic layer 201 and the GMR device 205. Ingredients of adjacent materials to be sensed are exposed in the sensing hole 208.

The switching device comprises a NMOS transistor. The NMOS transistor has a drain 209 connected to a sense bitline 215 through a contact line 212, a gate 211 connected to a wordline 214, and a source 210 connected to the sensing conductive layer 203 of the GMR device 205 through a contact line 213.

Figure 51A:
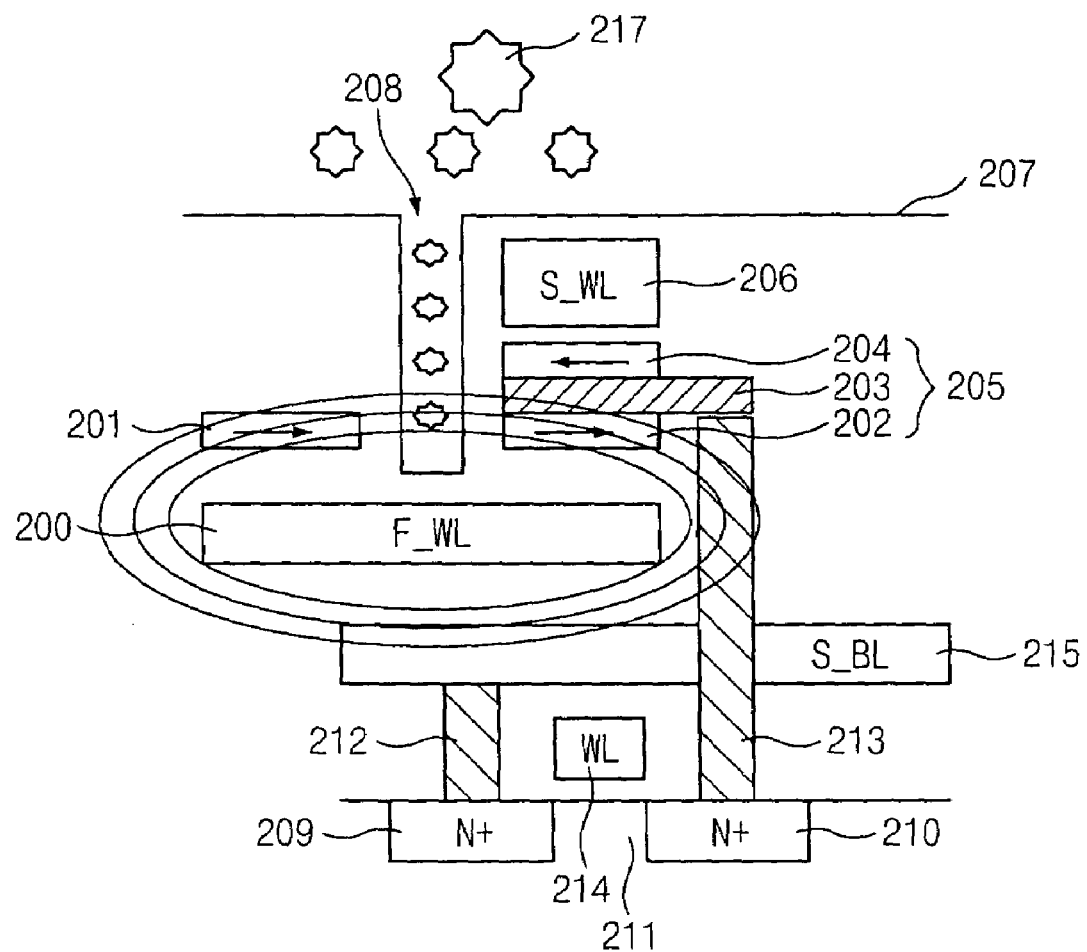
FIGS. 51a and 51b are diagrams illustrating variations in magnetic susceptibility depending on the size of a sensing hole of the magnetization hole detection sensor of FIG. 50.
Figure 51B:
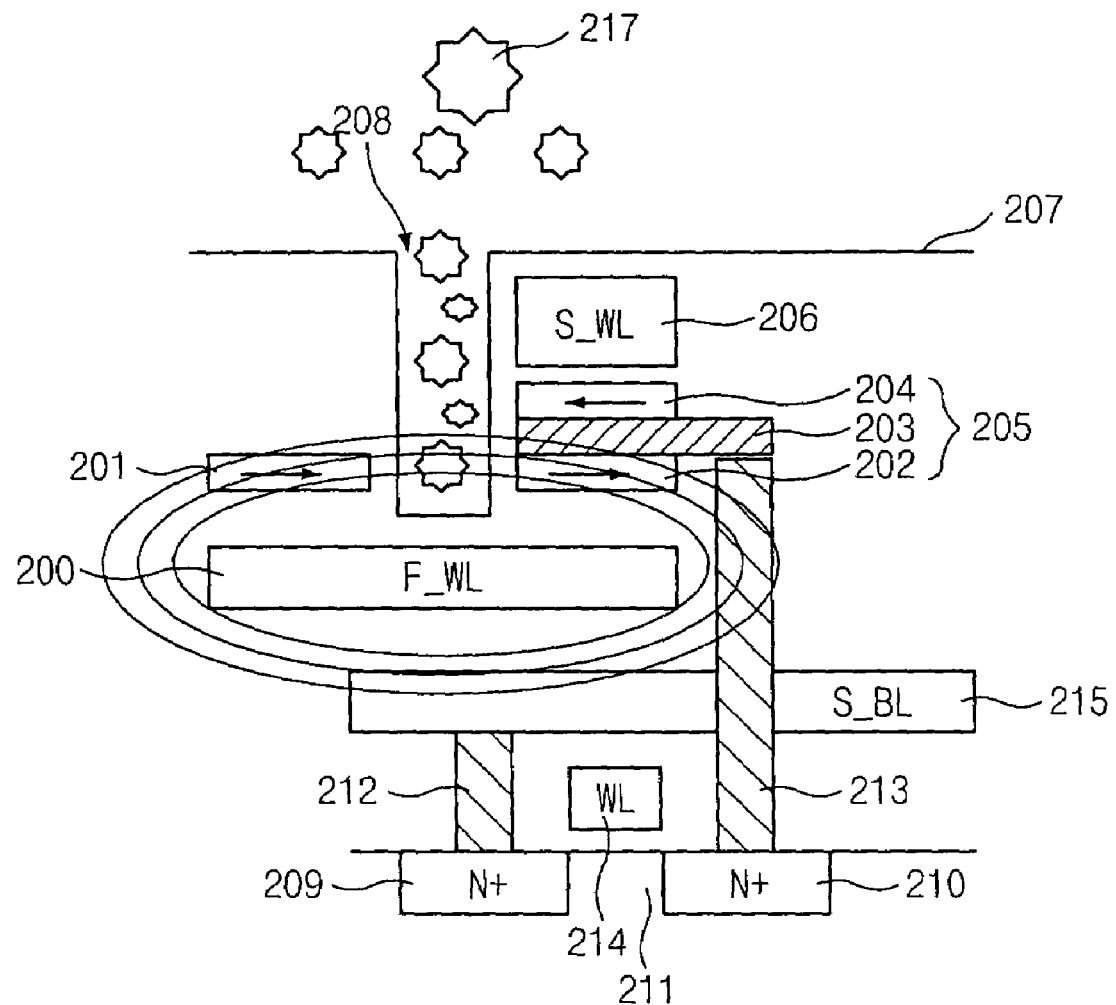

FIGS. 51a and 51b are diagrams illustrating variations in magnetic susceptibility depending on the size of a sensing hole of the magnetization hole detection sensor using the GMR device 205 of FIG. 50.

As shown in FIG. 51a, when the distance between the free ferromagnetic layers 201 and 202 is short, the size of the sensing hole 208 becomes smaller. Ingredients of adjacent materials having a size larger than the sensing hole 208 cannot penetrate into the sensing hole 208. As a result, ingredients of the adjacent materials 217 having the small size may be sensed by sensing the magnetization constant u of the adjacent materials 217 exposed in the sensing hole 208.

As shown in FIG. 51b, when the distance between the free ferromagnetic layers 201 and 202 is long, the size of the sensing hole 208 becomes larger. Ingredients of adjacent materials having a size smaller than the sensing hole 208 can penetrate into the sensing hole 208. As a result, ingredients of the adjacent materials 217 having the large size may be sensed by sensing the magnetization constant u of the adjacent materials 217 exposed in the sensing hole 208.

Figure 52:
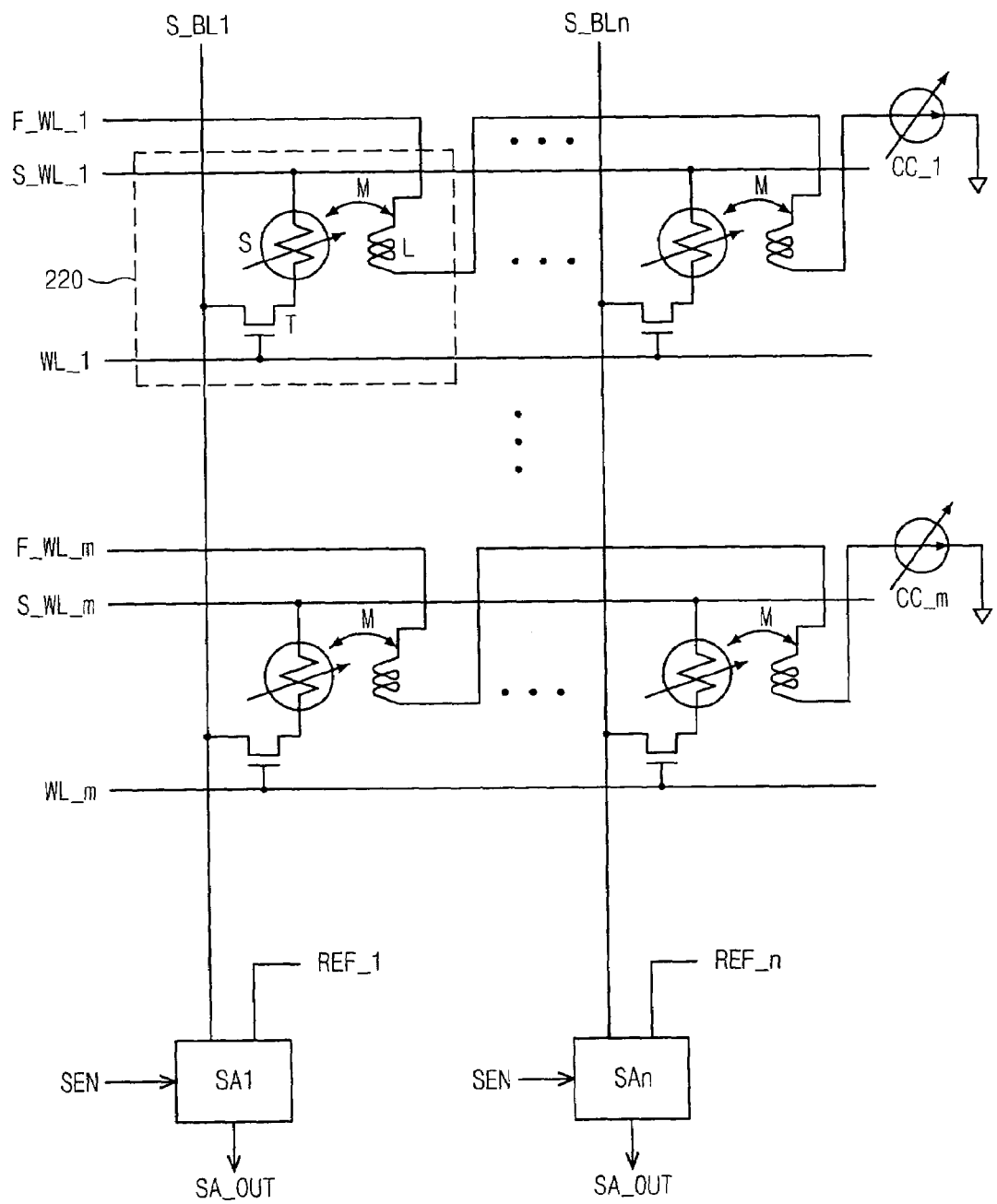
FIGS. 52 and 53 are diagrams illustrating examples of a sensing cell array using a magnetization hole detection sensor according to an embodiment of the present invention.

FIG. 52 is a diagram illustrating an example of a sensing cell array using a magnetization hole detection sensor according to an embodiment of the present invention.

In the sensing cell array using a magnetization hole detection sensor, a plurality of wordlines WL_1~WL_m are arranged parallel to a plurality of forcing wordlines F_WL_1~F_WL_m and a plurality of sense wordlines S_WL_1~S_WL_m in a row direction. In a column direction, a plurality of sense bitlines S_BL1~S_BLn are arranged perpendicular to a plurality of forcing wordlines F_WL_1~F_WL_m, the plurality of sense wordlines S_WL_1~S_WL_m and the plurality of wordlines WL_1~WL_m.

A plurality of magnetization hole detection sensors 220 are positionedbetween the plurality of forcing wordlines F_WL_1F_WL_m, the plurality of sense wordlines S_WL_1~S_WL_m, the plurality of wordlines WL_1~WL_m and the plurality of sense bitlines S_BL1~S_BLn.

A magnetization hole detection sensor 220 comprises a switching device T, a sensor S and a current line L for inducing a magnetic field. Here, the sensor S may be a MTJ or GMR device.

The switching device T has a drain connected to the sense bitline S_BL, a source connected to a terminal of the sensor S, and a gate connected to a wordline WL. The other terminal of the sensor S is connected to the sense wordline S_WL.

The current line L has a terminal connected to the forcing wordline F_WL, and the other terminal connected to a plurality of current regulators CC_1~CC_m, respectively. The plurality of current regulators CC connected between the current line L and a ground voltage terminal apply current for generating an induction magnetic field to the current lines L.

The plurality of sense bitlines S_BL1~S_BLn are connected one by one to a plurality of sense amplifiers SA1~SAn. The plurality of sense amplifiers SA1~SAn receive a plurality of reference voltages REF_1~REF_n and a plurality of sense amplifier enable signals SEN to output sense amplifier output signals SA_OUT. Here, each of the plurality of reference voltages REF_1~REF_n has different reference voltage values. That is, in the sensing cell array using the magnetization hole detection sensor, characteristics of blood ingredients are variously analyzed by the reference voltages REF having different levels.

If the wordline WL is enabled, the switching device T is turned on. As a result, different current values are outputted into the sense bitlines S_BL depending on the magnetic flux density sensed in the sensor S.

The sense amplifiers SA amplify current applied from the sense bitlines S_BL depending on the sense amplifier enable signals SEN to output sense amplifier output signals SA_OUT. As a result, each row and each column of the sensing cell array using the magnetization hole detection sensor obtain characteristics of different ingredients.

Figure 53:
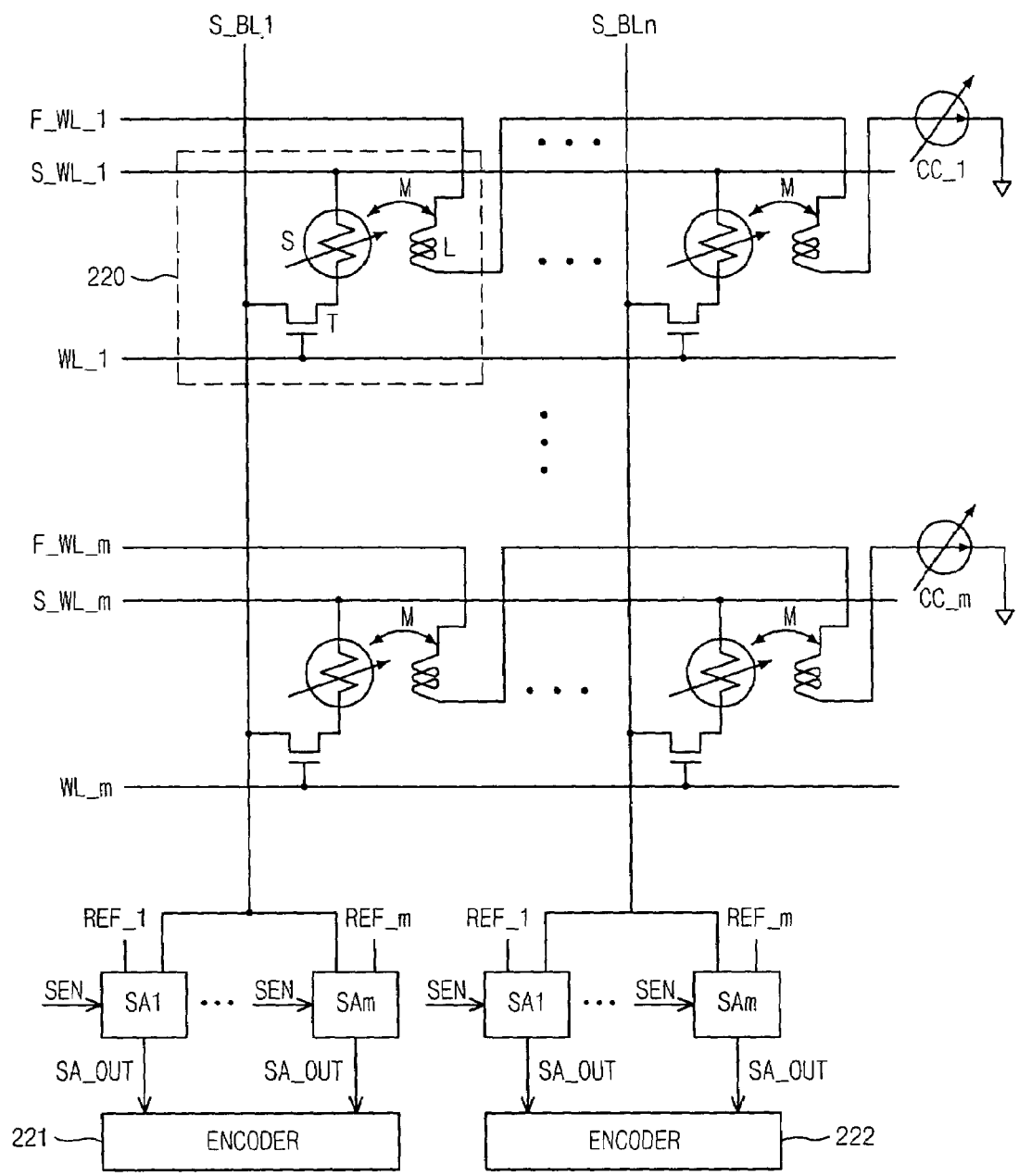

FIG. 53 is a diagram illustrating another example illustrating a sensing cell array using a magnetization hole detection sensor.

In the sensing cell array of FIG. 53, a sense bitline S_BL is connected to a plurality of sense amplifiers SA1~SAm. A sense bitline S_BL is connected to the plurality of sense amplifiers SA1~SAm which receive a plurality of different reference voltages REF_1~REF_m, correspondingly.

The plurality of sense amplifier output signals SA_OUT from the plurality of sense amplifiers SA1~SAm are outputted into encoders 221 and 222, and encoded for analysis of ingredients of adjacent materials therein.

Figure 54:
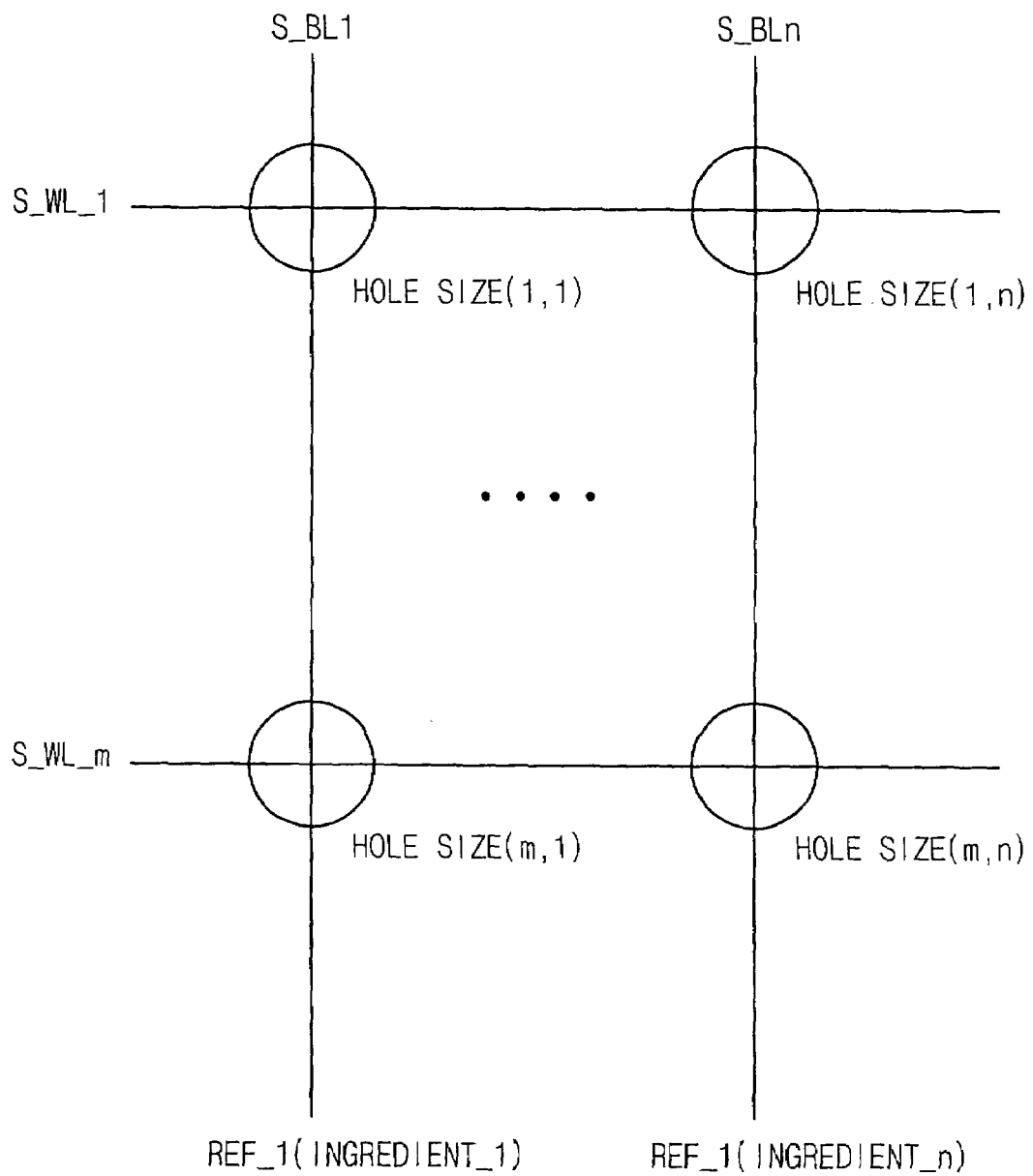
FIG. 54 is an ingredient analysis diagram illustrating a magnetization hole detection sensor according to an embodiment of the present invention.

FIG. 54 is an ingredient analysis diagram illustrating the magnetization hole detection sensor depending on sensing output values of the sensing cell array.

Sensing holes 189 and 208 are positionedbetween the plurality of sense wordlines S_WL and the plurality of sense bitlines S_BL. Ingredients of adjacent materials are separated depending on comparison of output values of the sense bitlines S_BL and the different reference voltages REF. As a result, in the sensing cell array using the magnetization hole detection sensor, different characteristics of adjacent materials may be separated and analyzed.

Figure 55:
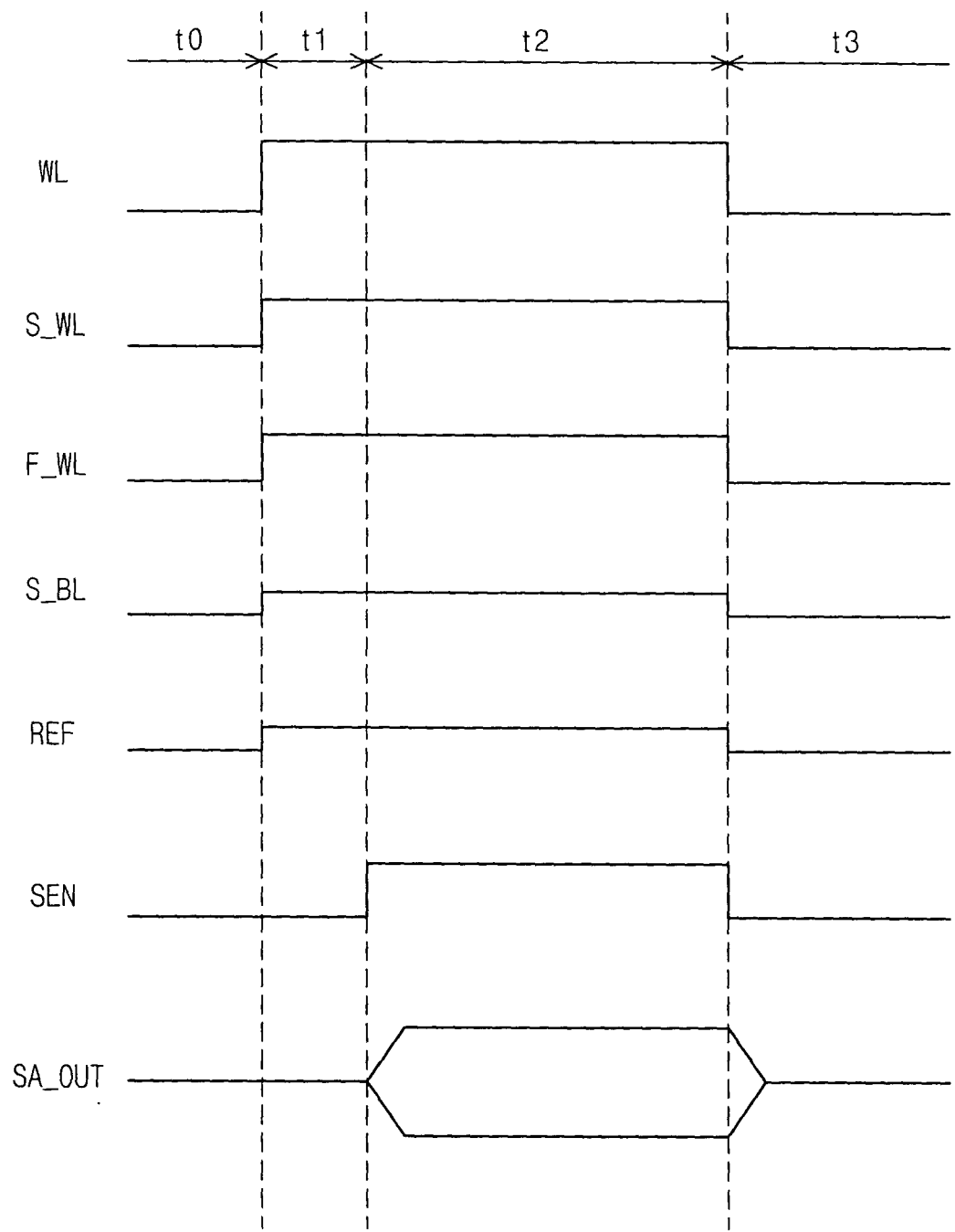
FIG. 55 is a timing diagram illustrating a read operation of the sensing cell array using the magnetization hole detection sensor according to an embodiment of the present invention.

FIG. 55 is a timing diagram illustrating a read operation of the sensing cell array using the magnetization hole detection sensor according to an embodiment of the present invention.

In an interval t1, the wordline WL, the sense wordline S_WL, the forcing wordline F_WL, the sense bitline S_BL and the reference voltage REF are activated. Then, different output values sensed in the sensor S are outputted into each sense amplifier SA through the sense bitline S_BL.

In an interval t2, if the sense amplifier enable signals SEN are activated, different output values sensed in the sense amplifiers SA and the reference voltages REF are compared and amplified, and the sense amplifier output signals SA_OUT are outputted. As a result, the blood ingredient analysis means analyzes each sense amplifier output signal SA_OUT from the sensing cell array to analyze ingredients of adjacent materials.

In an interval t3, the wordline WL, the sense wordline S_WL, the forcing wordline F_WL, the sense bitline S_BL and the reference voltage REF are inactivated. The sense amplifier enable signal SEN is disabled, and the operation stops.

Hereinafter, a dielectric constant sensor and a sensing cell array using the same according to a fifth embodiment of the present invention are described referring to FIGS. 56 to 64.

Figure 56:
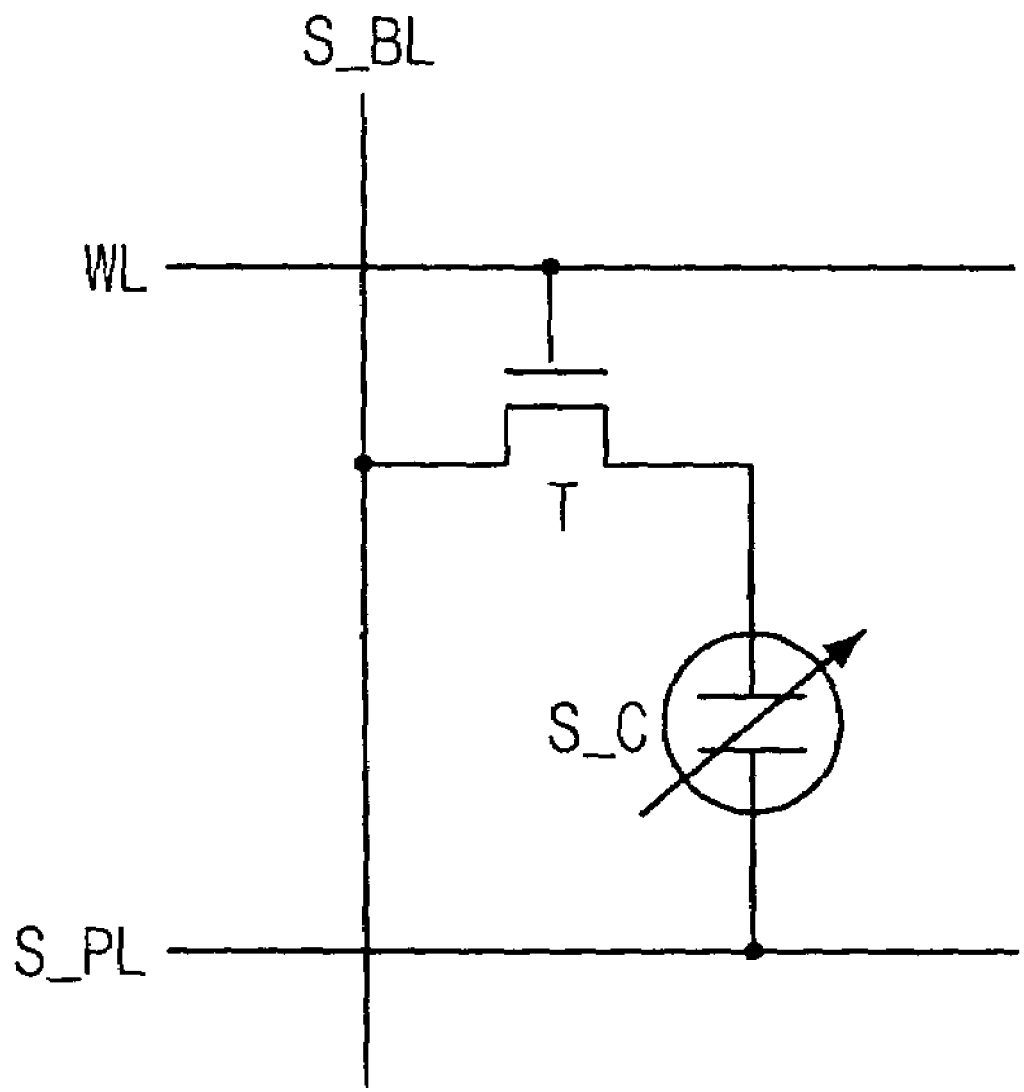
FIG. 56 is a diagram illustrating a dielectric constant sensor according to an embodiment of the present invention.

FIG. 56 is a diagram illustrating a dielectric constant sensor according to an embodiment of the present invention.

In an embodiment, the dielectric constant sensor comprises a switching device T and a sensing capacitor S_C.

The switching device T comprises a NMOS transistor. The NMOS transistor has a drain connected to a sensing bitline S_BL, a gate connected to a wordline WL, and a source connected to a second electrode of the sensing capacitor S_C. A first electrode of the sensing capacitor S_C is connected to a sensing plate line S_PL. As a result, different sensing voltages of the sensing bitline S_BL are detected depending on the capacitance of the sensing capacitor S_C.

Figure 57A:
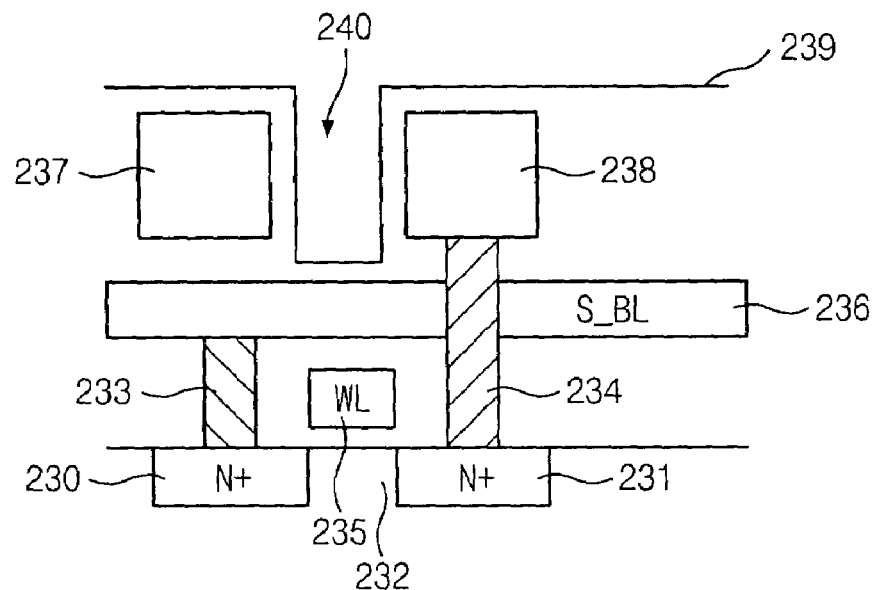
FIGS. 57a and 57b are cross-sectional and planar view diagrams illustrating the dielectric constant sensor according to an embodiment of the present invention.
Figure 57B:
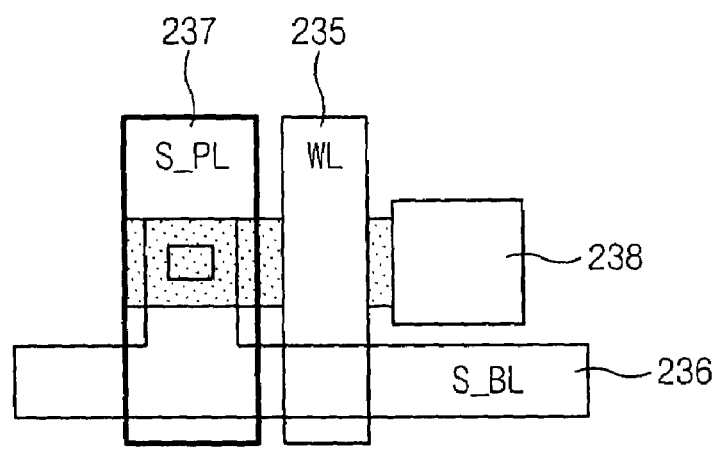

FIGS. 57a and 57b are cross-sectional and planar view diagrams illustrating the dielectric constant sensor according to an embodiment of the present invention.

In an embodiment, a NMOS transistor has a drain 230 connected to a sensing bitline 236 through a contact line 233, a gate 232 connected to a wordline 235, and a source 231 connected to a second electrode 238 of a sensing capacitor. A first electrode 237 of the sensing capacitor is connected to a sensing plate line S_PL. A sensing hole 240 is formed between the first electrode 237 and the second electrode 238 of the sensing capacitor. The sensing hole 240 corresponds to the distance between the two electrodes and the area of the sensing electrode. Also, the whole device is insulated by an oxide protective layer 239.

In the dielectric constant sensor, the sensing hole 240 is formed depending on the distance between the first electrode 237 and the second electrode 238 and the area of the sensing electrode. Ingredients of adjacent materials to be sensed are exposed in the sensing hole 240.

Figure 58:
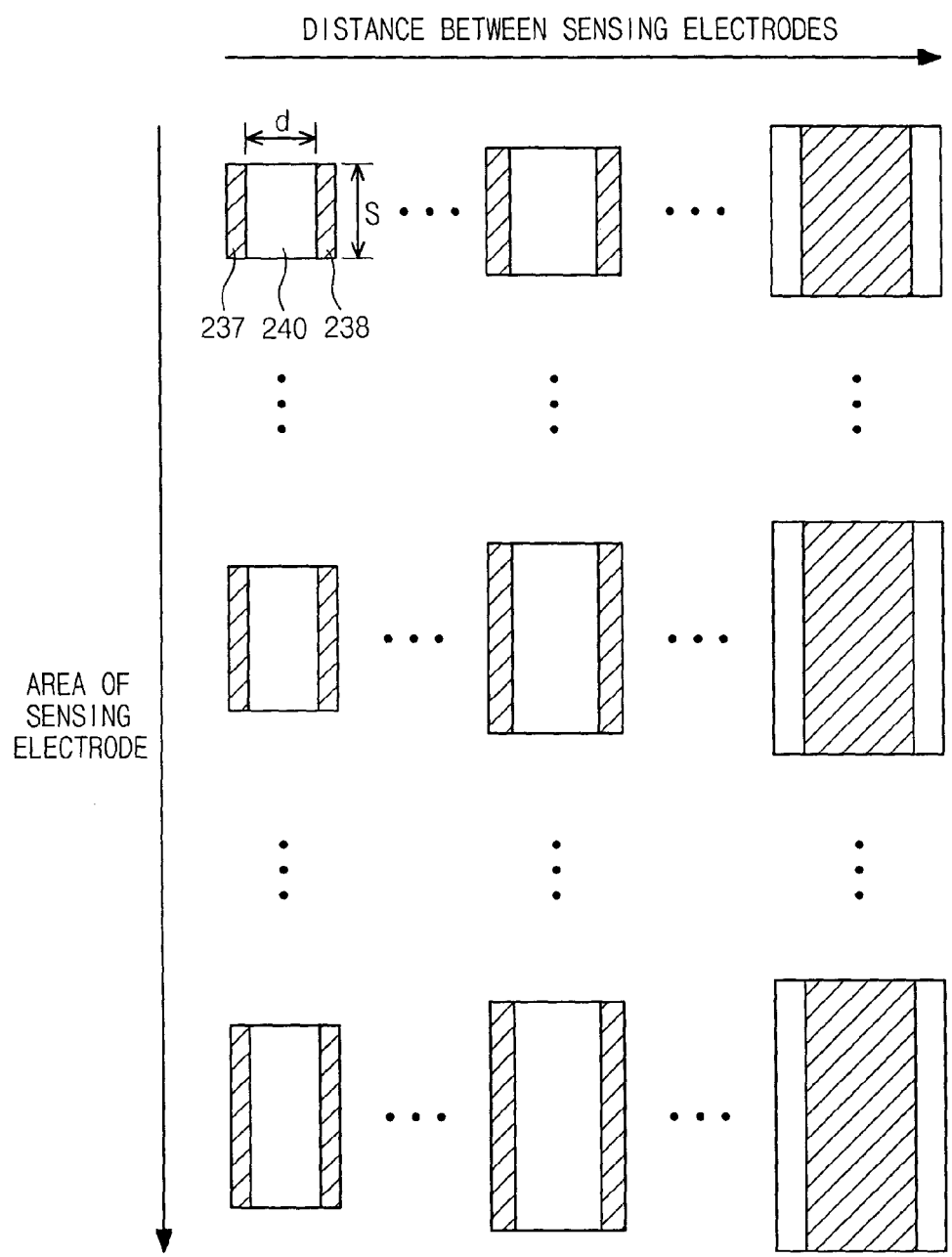
FIG. 58 is a diagram illustrating sensing hole types of the dielectric constant sensor according to an embodiment of the present invention.

FIG. 58 is a diagram illustrating sensing hole 240 types of the dielectric constant sensor according to an embodiment of the present invention.

In an embodiment, a horizontal direction is set as variables depending on the distance d between the free ferromagnetic layers 237 and 238, and a vertical direction is set as variables depending on the area S of the free ferromagnetic layers 237 and 238. As a result, the sizes of ingredients of adjacent materials may be separated depending on the distance between the free ferromagnetic layers 237 and 238, and the amounts of ingredients corresponding to the sizes of adjacent materials may be analyzed quantitatively depending on the area S between the free ferromagnetic layers 237 and 238.

Figure 59A:
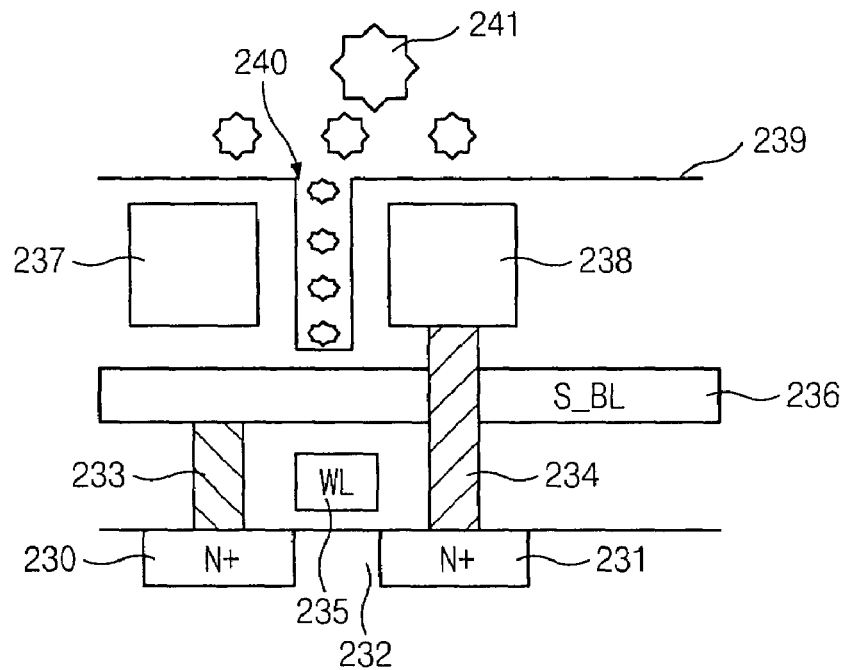
FIGS. 59a and 59b are diagrams illustrating a variation in dielectric constant depending on the sizes of sensing holes of the dielectric constant sensor according to an embodiment of the present invention.
Figure 59B:
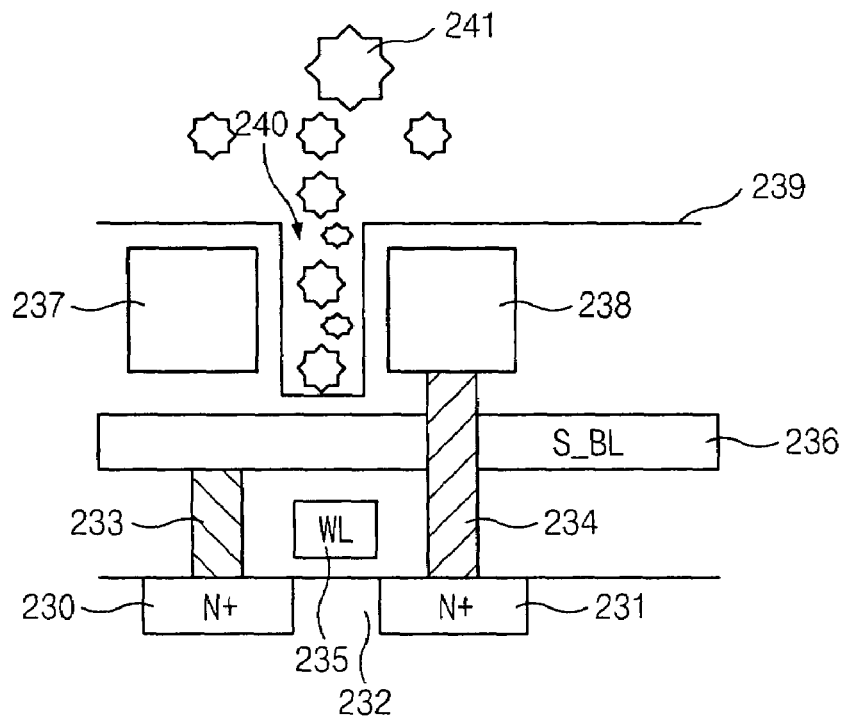

FIGS. 59a and 59b are diagrams illustrating variations in dielectric constant depending on the sizes of the sensing holes of the dielectric constant sensor according to an embodiment of the present invention.

As shown in FIG. 59a, when the distance between the free ferromagnetic layers 237 and 238 is short, the size of the sensing hole 240 becomes smaller. Ingredients of adjacent materials having a size larger than the sensing hole 240 cannot penetrate into the sensing hole 240. As a result, ingredients of the adjacent materials 241 having the small size may be sensed by sensing the dielectric constant $\in$ of the adjacent materials exposed in the sensing hole 240.

As shown in FIG. 59b, when the distance between the free ferromagnetic layers 237 and 238 is long, the size of the sensing hole 240 becomes larger. Ingredients of adjacent materials 241 having a size smaller than the sensing hole 240 can penetrate into the sensing hole 240. As a result, ingredients of the adjacent materials having a large size may be sensed by sensing the dielectric constant $\in$ of the adjacent materials 241 exposed in the sensing hole 240.

Figure 60:
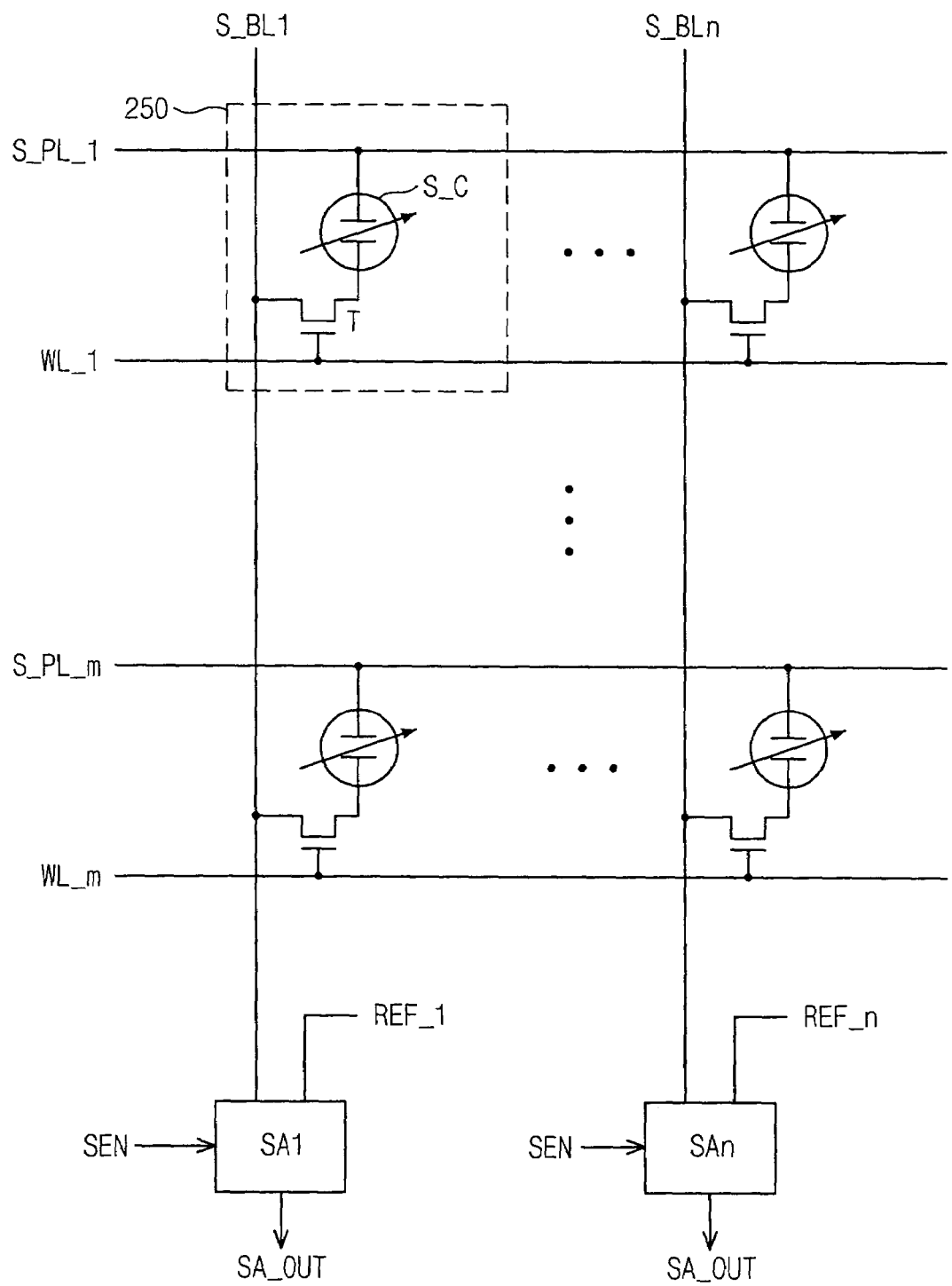
FIGS. 60 and 61 are diagrams illustrating a sensing cell array using the dielectric constant sensor according to an embodiment of the present invention.

FIG. 60 is a diagram illustrating an example of a sensing cell array using the dielectric constant sensor according to an embodiment of the present invention.

In a sensing cell array using a dielectric constant sensor, a plurality of wordlines WL_1~WL_m are arranged parallel to a plurality of sensing platelines S_PL_1~S_PL_m in a row direction. In a column direction, a plurality of sensing bitlines S_BL1~S_BLn are arranged perpendicular to the plurality of wordlines WL_1~WL_m and the plurality of sensing platelines S_PL_1~S_PL_m.

A plurality of dielectric constant sensors 250 are positionedbetween the plurality of wordlines WL_1~WL_m, the plurality of sensing platelines S_PL_1~S_PL_M, and the plurality of sensing bitlines S_BL1~S_BLn.

A dielectric constant sensor 250 comprises a switching device T and a sensing capacitor S_C. The switching device T has a drain connected to the sensing bitline S_BL, a source connected to a second electrode of the sensing capacitor S_C, and a gate connected to a wordline WL. A first electrode of the sensing capacitor S_C is connected to the sensing plateline S_PL.

The plurality of sensing bitlines S_BL1~S_BLn are connected one by one to a plurality of sense amplifiers SA1~SAn. The plurality of sense amplifiers SA1~SAn receive a plurality of reference voltages REF_1~REF_n and a plurality of sense amplifier enable signals SEN to output a plurality of sense amplifier output signals SA_OUT. Here, each of the plurality of reference voltages REF_1~REF_n has different reference voltage values.

Each column of the sensing cell array using the dielectric constant sensor allows blood ingredients to be separated and analyzed variously by the reference voltages REF_1~REF_n having different levels.

If the wordline WL is enabled, the switching device T is turned on to output voltages sensed depending on the capacitance of the sensing capacitor S_C into the sensing bitlines S_BL.

The sense amplifiers SA amplify sensing voltages applied from the sense bitlines S_BL in response to the sense amplifier enable signals SEN. The sense amplifiers SA output different sense amplifier output signals SA_OUT in response to different reference voltages REF. As a result, each row and each column of the sensing cell array using the dielectric constant sensor obtain characteristics of different ingredients.

Figure 61:
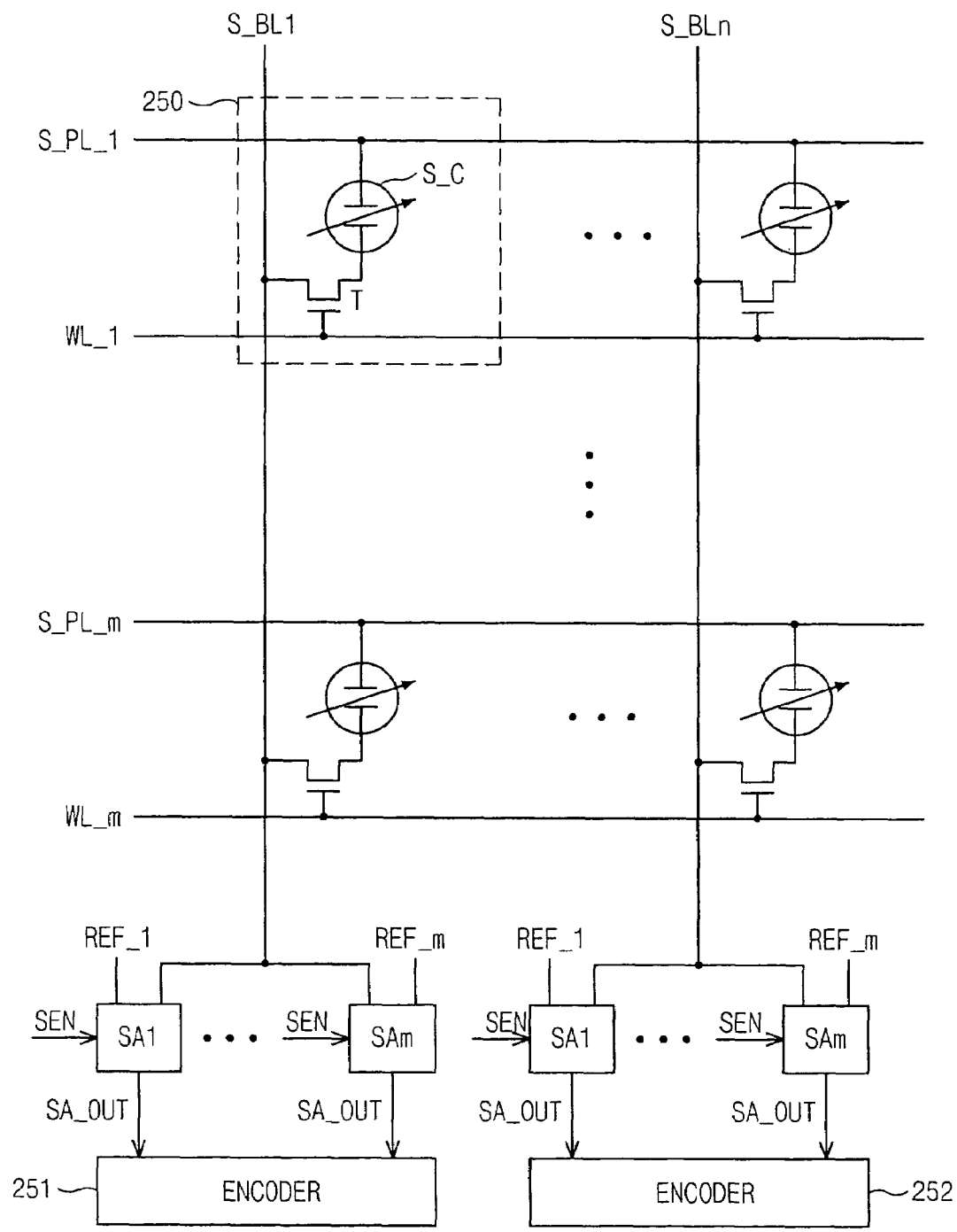

FIG. 61 is a diagram illustrating another example of a sensing cell array using the dielectric constant sensor according to an embodiment of the present invention.

In the sensing cell array of FIG. 61, a sensing bitline S_BL is connected to a plurality of sense amplifiers SA1~SAm. Each of the sense amplifiers SA1~SAm receives a plurality of different reference voltages REF_1~REF_m, correspondingly.

The plurality of sense amplifier output signals SA_OUT from the plurality of sense amplifiers SA1~SAm are outputted into encoders 221 and 222, and encoded for analysis of ingredients of adjacent materials therein.

Figure 62:
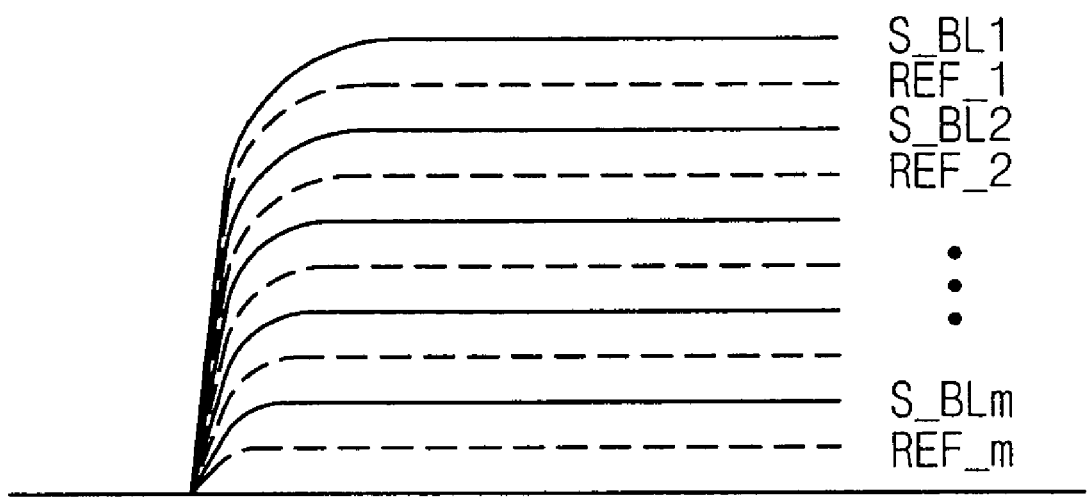
FIG. 62 is a diagram illustrating the relationship between a sensing bitline and a reference voltage according to an embodiment of the present invention.

FIG. 62 is a diagram illustrating the relationship between a sensing bitline S_BL and a reference voltage REF according to an embodiment of the present invention.

A plurality of sensing bitlines S_BL1~S_BLm output a plurality of sensing voltage levels sensed in a sensing capacitor S_C sensed through a switching transistor T. A plurality of sense amplifiers SA compare the plurality of sensing voltage levels applied from the plurality of sensing bitlines S_BL1~S_BLm with a plurality of different reference voltages REF_1~REF_m to decide which reference voltage levels REF_1~REF_m correspond to sensed ingredients of adjacent materials.

Figure 63:
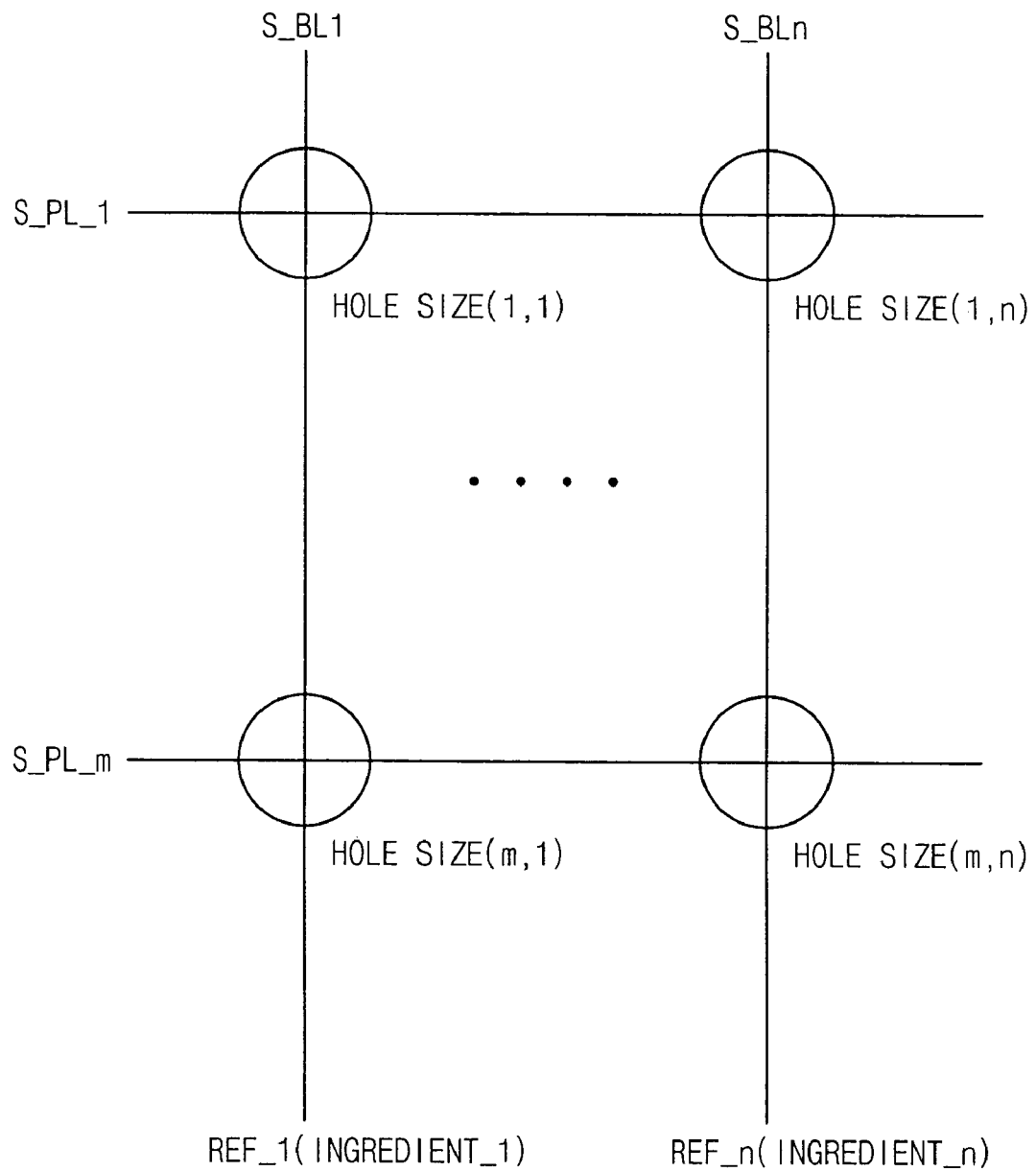
FIG. 63 is an ingredient analysis diagram illustrating the dielectric constant sensor according to an embodiment of the present invention.

FIG. 63 is an ingredient analysis diagram illustrating the dielectric constant sensor according to an embodiment of the present invention.

A plurality of sensing holes 240 are positioned between the plurality of sensing plateline S_PL and the plurality of sensing bitlines S_BL. Ingredients of adjacent materials are separated depending on comparison of output values of the sensing bitlines S_BL and the different reference voltages REF. As a result, in the sensing cell array using the dielectric constant sensor, different characteristics of adjacent materials may be separated and analyzed.

Figure 64:
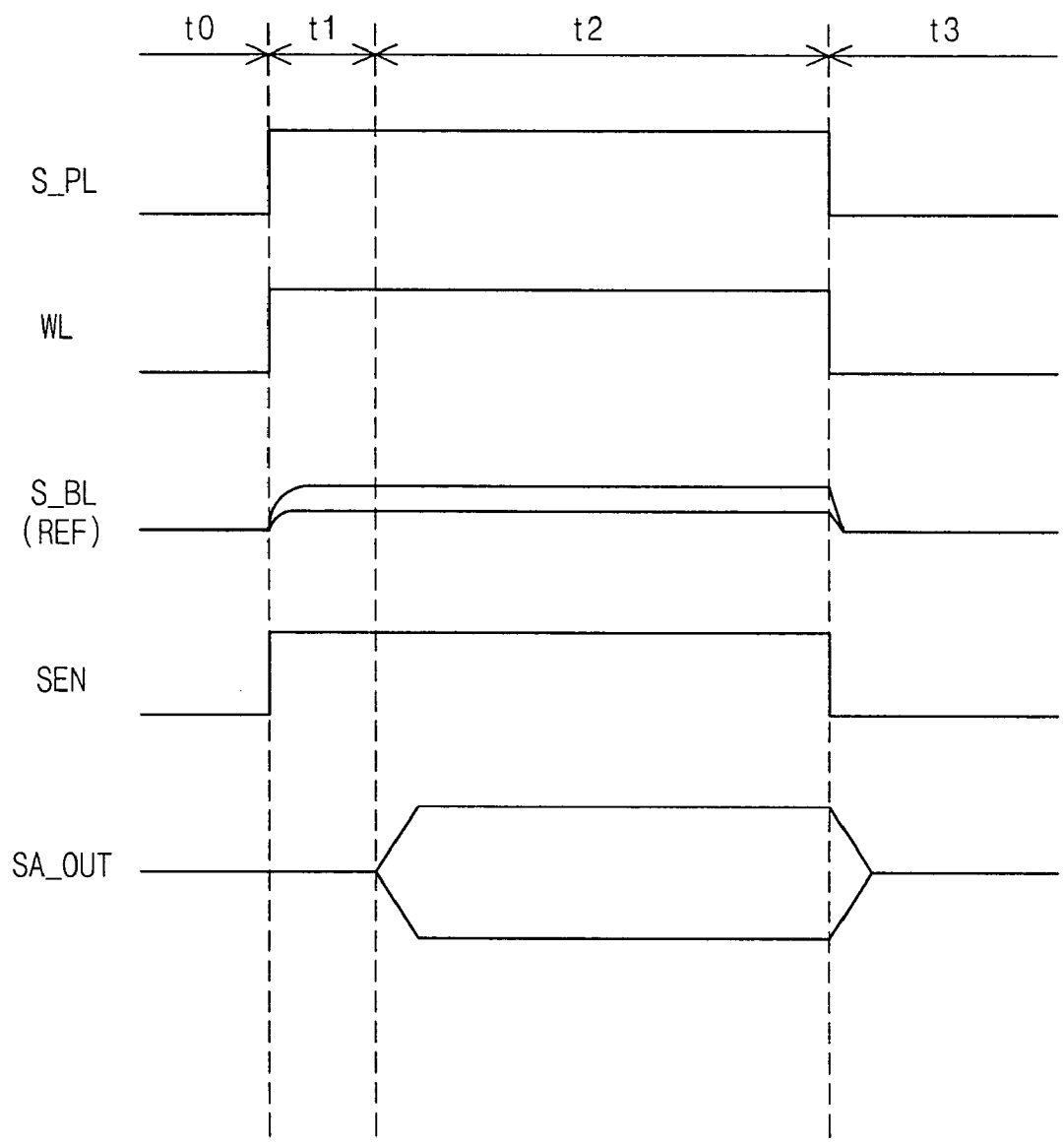
FIG. 64 is a timing diagram illustrating the read operation of the sensing cell array using the dielectric constant sensor according to an embodiment of the present invention.

FIG. 64 is a timing diagram illustrating the read operation of the sensing cell array using the dielectric constant sensor according to an embodiment of the present invention.

In an interval t1, the wordline WL, the sensing plateline S_PL, the sensing bitline S_BL and the reference voltage REF are activated. The different sensing voltage values sensed in the sensing capacitor S_C are outputted into each sense amplifier SA through the sensing bitlines S_BL. Thereafter, the sense amplifiers SA compare and amplify the reference voltages REF with sensing voltage values inputted through the sensing bitlines S_BL.

In an interval t2, if the sense amplifier enable signal SEN is activated, the different sensing voltage values sensed in the sense amplifiers SA are amplified, and then the sense amplifier output signals SA_OUT are outputted.

The blood ingredient analysis means analyzes each sense amplifier output signal SA_OUT from the sensing cell array to analyze ingredients of adjacent materials.

In an interval t3, the wordline WL, the sensing plateline S_PL, the sensing bitline S_BL and the reference voltage REF are inactivated. The sense amplifier enable signal SEN is disabled, and the operation stops.

As discussed earlier, in an embodiment of sensing cell arrays, various ingredients of adjacent materials may be simultaneously analyzed within a short time. That is, ingredients of adjacent materials may be analyzed at a time level of nano-seconds using biosensors, compound ingredient analysis sensors and skin recognizing sensors.

Additionally, since a chip size of the sensing cell array is small, samples for test can be reduced.

While the present invention is susceptible to various modifications and alternative forms, specific embodiments have been shown by way of example in the drawings and described in detail herein. However, it should be understood that the invention is not limited to the particular forms disclosed. Rather, the invention covers all modifications, equivalents, and alternatives falling within the spirit and scope of the invention as defined in the appended claims.

What is claimed is:

1. A biosensor, comprising:
a MTJ (Magnetic Tunnel Junction) device comprising a free ferromagnetic layer, a tunnel junction layer and a fixed ferromagnetic layer;
a switching device, formed under the fixed ferromagnetic layer of the MTJ device, for outputting current sensed in the MTJ device into a sense bitline; and
a sense wordline, formed on the free ferromagnetic layer, for applying different bias voltages to the MTJ device,
wherein when a magnetic field of the fixed ferromagnetic layer is transmitted into the free ferromagnetic layer, the current outputted from the switching device varies according to a magnetic flux density depending on adjacent materials.

2. The biosensor according to claim 1, further comprising a barrier conductive layer under the fixed ferromagnetic layer of the MTJ device.

3. The biosensor according to claim 2, wherein the switching device comprises:
a drain connected to the sense bitline;
a source connected to the barrier conductive layer; and
a gate connected to a wordline.

4. The biosensor according to claim 1, further comprising an oxide protective layer, formed on the MTJ device, the switching device and the sense wordline.

5. A biosensor comprising:
a MTJ device comprising a free ferromagnetic layer to receive a sense wordline voltage, a tunnel junction layer and a fixed ferromagnetic layer;
a ferromagnetic material, formed on the free ferromagnetic layer, for forming a magnetic field depending on magnetic coupling with the free ferromagnetic layer; and
a switching device, formed under the fixed ferromagnetic layer of the MTJ device, for outputting current sensed in the MTJ device into a sense bitline,
wherein the current outputted from the switching device varies according to magnetoresistive values depending on adjacent materials.

6. The biosensor according to claim 5, further comprising a barrier conductive layer formed under the fixed ferromagnetic layer of the MTJ device.

7. The biosensor according to claim 6, wherein the switching device comprises:
a drain connected to the sense bitline;
a source connected to the barrier conductive layer; and
a gate connected to a wordline.

8. The biosensor according to claim 5, further comprising an oxide protective layer formed on the MTJ device, the switching device and the magnetic material.

9. The biosensor according to claim 5, further comprising an insulating material, formed between the MTJ device and the magnetic material.

10. A biosensor comprising:
a MTJ device comprising a free ferromagnetic layer to receive a sense wordline voltage, a tunnel junction layer and a fixed ferromagnetic layer;
a current line, formed on the free ferromagnetic layer, for receiving a forcing wordline voltage and forming a magnetic field depending on magnetic coupling with the free ferromagnetic layer; and
a switching device, formed under the fixed ferromagnetic layer of the MTJ device, outputting current sensed in the MTJ device into a sense bitline,
wherein the current outputted from the switching device varies according to magnetoresistive values depending on adjacent materials.

11. The biosensor according to claim 10, further comprising a barrier conductive layer formed under the fixed ferromagnetic layer of the MTJ cell.

12. The biosensor according to claim 11, wherein the switching device comprises:
a drain connected to the sense bitline;
a source connected to the barrier conductive layer; and
a gate connected to a wordline.

13. The biosensor according to claim 10, further comprising an oxide protective layer, formed on the MTJ device, the switching device and the current line.

14. The biosensor according to claim 10, further comprising an insulating material, formed between the MTJ device and the current line.

* * * * *